US011133092B2

(12) United States Patent
Haws et al.

(10) Patent No.: US 11,133,092 B2
(45) Date of Patent: Sep. 28, 2021

(54) SYSTEM AND METHODS FOR ANIMAL DENTAL CHARTING

(71) Applicant: ANIMAL DENTAL CHART INC., Erin (CA)

(72) Inventors: Ian James Haws, Erin (CA); Gary Edwin Campbell, Kelowna (CA)

(73) Assignee: ANIMAL DENTAL CHART INC., Erin (CA)

( * ) Notice: Subject to any disclaimer, the term of this patent is extended or adjusted under 35 U.S.C. 154(b) by 132 days.

(21) Appl. No.: 16/225,560

(22) Filed: Dec. 19, 2018

(65) Prior Publication Data
US 2019/0244693 A1    Aug. 8, 2019

Related U.S. Application Data

(60) Provisional application No. 62/627,471, filed on Feb. 7, 2018.

(51) Int. Cl.
*G16H 10/60*    (2018.01)
*A61B 5/00*    (2006.01)
(Continued)

(52) U.S. Cl.
CPC ........... *G16H 10/60* (2018.01); *A61B 5/4547* (2013.01); *A61B 5/7435* (2013.01); *G16H 15/00* (2018.01);
(Continued)

(58) Field of Classification Search
None
See application file for complete search history.

(56) References Cited

U.S. PATENT DOCUMENTS

| 7,343,305 B2 | 3/2008 | Benn |
| 7,474,932 B2 | 1/2009 | Geng |

(Continued)

FOREIGN PATENT DOCUMENTS

WO    WO-02091279 A2 *  11/2002  ............. G16H 30/40

OTHER PUBLICATIONS

OpenDental.com/manual/chart.html (captured using Wayback Machine, author unknown) (Year: 2015).*

(Continued)

*Primary Examiner* — Rachelle L Reichert
(74) *Attorney, Agent, or Firm* — Norton Rose Fulbright Canada LLP

(57) ABSTRACT

A dental charting system and method of generating a dental chart are provided. The dental charting system comprises a display unit, an input unit and an output unit. The display unit is configured to display a quadrant view of a set of teeth. The quadrant view comprises a quadrant subset of the set of teeth, and at least one of a diagnosis field and a procedure field for each tooth in the quadrant subset. Each tooth in the quadrant subset displayed having a crown, a root and an outline. The input unit is configured to receive an input for at least one of the diagnosis field and the procedure field for at least one tooth in the quadrant set of teeth. The output unit is configured to generate a dental chart displaying the set of teeth. Each tooth in the set of teeth displayed in a color associated with the received input for at least one of the diagnosis field and the procedure field. The method comprises displaying a quadrant view of a set of teeth, receiving an input for at least one of the diagnosis field and the procedure field for at least one tooth in the quadrant set of teeth, and generating a dental chart displaying the set of teeth.

21 Claims, 62 Drawing Sheets

(51) Int. Cl.
  *G16H 15/00* (2018.01)
  *A61D 5/00* (2006.01)
(52) U.S. Cl.
  CPC .......... *A61B 5/743* (2013.01); *A61B 2503/40* (2013.01); *A61D 5/00* (2013.01)

(56) References Cited

U.S. PATENT DOCUMENTS

| | | | |
|---|---|---|---|
| D589,524 S | 3/2009 | Orellana | |
| 7,756,727 B1 | 7/2010 | Greenspan | |
| 7,916,900 B2 | 3/2011 | Lanier | |
| 8,160,899 B2 | 4/2012 | Rhodes | |
| 8,416,984 B2 | 4/2013 | Liang | |
| D723,577 S | 3/2015 | Matias | |
| D741,884 S | 10/2015 | Lee | |
| D777,191 S | 1/2017 | Polimeni | |
| 9,710,603 B2 * | 7/2017 | Kaminski | A61C 19/00 |
| 9,792,413 B2 | 10/2017 | Badawi | |
| D852,838 S | 7/2019 | Ibsies | |
| RE47,596 E | 9/2019 | Muller | |
| D870,751 S | 12/2019 | Peeters | |
| D878,397 S | 3/2020 | Gratzki | |
| D889,496 S | 7/2020 | Giannino | |
| D913,298 S | 3/2021 | Haws | |
| 2004/0236608 A1 | 11/2004 | Ruggio | |
| 2006/0285636 A1 | 12/2006 | Razzano | |
| 2008/0172386 A1 | 7/2008 | Ammar | |
| 2010/0121658 A1 * | 5/2010 | Kaminski | G16H 50/20 705/3 |
| 2012/0189182 A1 * | 7/2012 | Liang | G16H 10/60 382/131 |
| 2013/0111353 A1 | 5/2013 | Ueda | |
| 2014/0023984 A1 | 1/2014 | Weatherly | |
| 2014/0282265 A1 | 9/2014 | Shaich | |
| 2015/0294066 A1 | 10/2015 | Golay | |
| 2016/0055321 A1 | 2/2016 | Acharya | |
| 2016/0124920 A1 | 5/2016 | Golay | |
| 2019/0043607 A1 * | 2/2019 | Sears | G16H 30/20 |

OTHER PUBLICATIONS

"Veterinary Dental Charting for Dummies." vetanswers.com.au. Jul. 30, 2020. Retrieved Mar. 24, 2021 online at URL: http://www.vetanswers.com.au/blog/post/veterinary-dental-charting-for-dummies/375 (Year: 2020).

Notice of Allowance issued on U.S. Appl. No. 29/770,496, dated Apr. 6, 2021.

Office Action issued on U.S. Appl. No. 29/658,981, dated Oct. 18, 2019.

Office Action issued on U.S. Appl. No. 29/658,981, dated Jun. 18, 2020.

* cited by examiner

Feline Dental Chart
Deciduous

Feline Occlusal Dental Chart
Deciduous

Patient:                                           Date:
Patient ID:                                        Veterinarian:

Right maxilla    501  ○  1st incisor  ○  601    Left maxilla
                 502  ○  2nd incisor  ○  602
                 503  ○  3rd incisor  ○  603
                 504  ⬭  canine       ⬭  604
                 506  ○  2nd premolar ○  606
                 507  ⬭  3rd premolar ⬭  607
                 508  ○  4th premolar ○  608

808  ⬭  4th premolar ⬭  708
                 807  ⬭  3rd premolar ⬭  707
                 804  ⬭  canine       ⬭  704
                 803  ○  3rd incisor  ○  703
                 802  ○  2nd incisor  ○  702
Right mandible   801  ○  1st incisor  ○  701    Left mandible Key
Pathology / Abnormality
Missing Tooth
Oral Surgery
Orthodontics

Diagnosis Tool

- ☑ ALL  ☐ Normal  ☐ Occlusion  ☐ Tooth Type or Pathology
- ☐ Periodontal Pathology and Measurements Search by Abbreviation: `frq`

| | Abbreviation | Medical Description | Category |
|---|---|---|---|
| ☐ | T/FX | Fractured tooth | Tooth Type or Pathology |
| ☐ | T/FX/CCF | Complicated crown fracture | Tooth Type or Pathology |
| ☐ | T/FX/CCRF | Complicated crown-root fracture | Tooth Type or Pathology |
| ☐ | T/FX/EF | Enamel fracture | Tooth Type or Pathology |
| ☐ | T/FX/EI | Enamel infraction | Tooth Type or Pathology |
| ☐ | T/FX/RF | Root fracture | Tooth Type or Pathology |
| ☐ | T/FX/UCF | Uncomplicated crown fracture | Tooth Type or Pathology |

860 → (callout)
864 → (callout to search field)

[ Save ]  [ Cancel ]

SYSTEM AND METHODS FOR ANIMAL DENTAL CHARTING

CROSS-REFERENCE TO RELATED APPLICATIONS

This application claims all benefit including priority to U.S. Provisional Patent Application 62/627,471, filed Feb. 7, 2018, and entitled: "System and Methods for Animal Dental Charting," which is hereby incorporated by reference in its entirety.

FIELD

The present disclosure generally relates to the field of animal dental charting.

INTRODUCTION

Veterinarians chart the teeth of dogs and cats. There a number of abbreviations, including an international standard of abbreviations, that veterinarians can use to speed up the diagnosis of a tooth of an animal. Speed of charting is desired for efficiency purposes and for the health and safety of the animal that is anesthetized during dental diagnostics and procedures.

SUMMARY

In accordance with one aspect, there is provided a dental charting system. The dental charting system comprises a display unit, an input unit and an output unit. The display unit is configured to display a quadrant view of a set of teeth. The quadrant view comprises a quadrant subset of the set of teeth, and at least one of a diagnosis field and a procedure field for each tooth in the quadrant subset. Each tooth in the quadrant subset displayed having a crown, a root and an outline. The input unit is configured to receive an input for at least one of the diagnosis field and the procedure field for at least one tooth in the quadrant set of teeth. The output unit is configured to generate a dental chart displaying the set of teeth. Each tooth in the set of teeth displayed in a color associated with the received input for at least one of the diagnosis field and the procedure field.

In accordance with another aspect, there is provided a method of generating a dental chart. The method comprises displaying a quadrant view of a set of teeth, receiving an input for at least one of the diagnosis field and the procedure field for at least one tooth in the quadrant set of teeth, and generating a dental chart displaying the set of teeth. The quadrant view comprises a quadrant subset of the set of teeth, and at least one of a diagnosis field and a procedure field for each tooth in the quadrant subset. Each tooth in the quadrant subset displayed having a crown, a root and an outline. Each tooth in the set of teeth displayed in a color associated with the received input for at least one of the diagnosis field and the procedure field.

In various further aspects, the disclosure provides corresponding systems and devices, and logic structures such as machine-executable coded instruction sets for implementing such systems, devices, and methods.

In this respect, before explaining at least one embodiment in detail, it is to be understood that the embodiments are not limited in application to the details of construction and to the arrangements of the components set forth in the following description or illustrated in the drawings. Also, it is to be understood that the phraseology and terminology employed herein are for the purpose of description and should not be regarded as limiting.

Many further features and combinations thereof concerning embodiments described herein will appear to those skilled in the art following a reading of the instant disclosure.

DESCRIPTION OF THE FIGURES

Embodiments will be described, by way of example only, with reference to the attached figures, wherein in the figures:

Figure 5C:
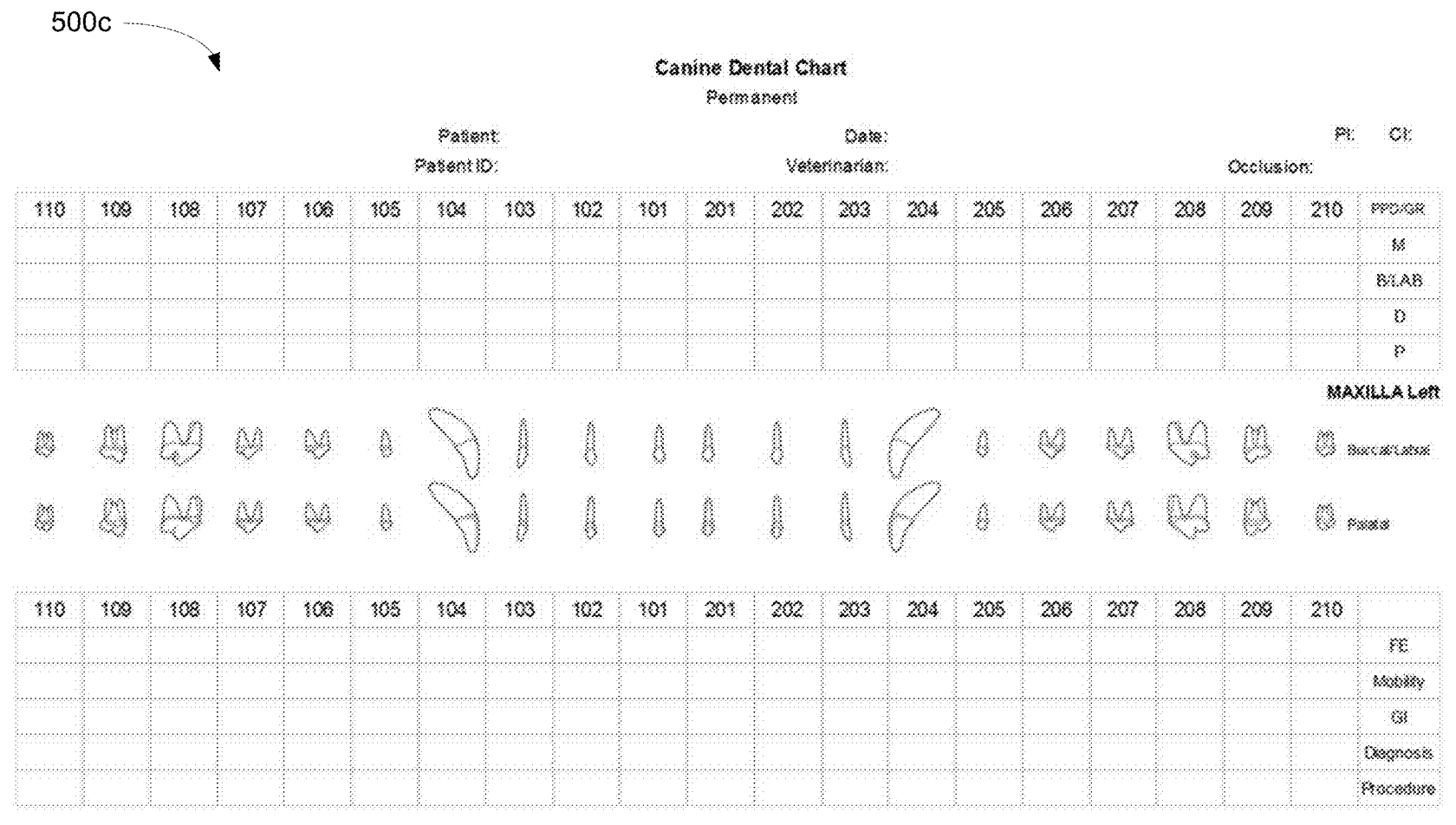
Figure 5F:
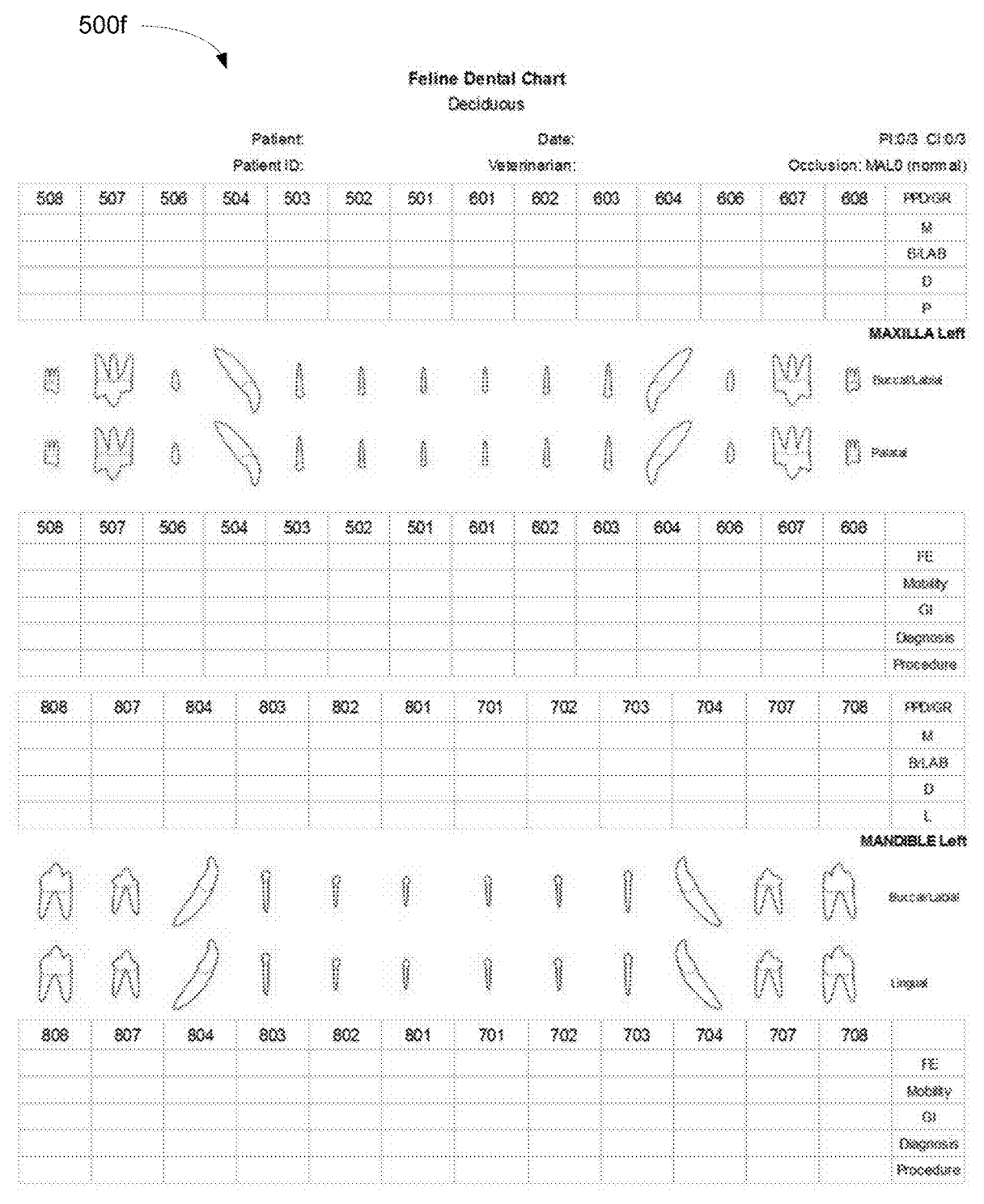

FIGS. 5A to 5I illustrate examples of a dental charts, in accordance with some embodiments.

FIGS. 8A to 8E Illustrate, in a sequence of screen shots, an example of the use of the dental charting system, in accordance with some embodiments.

FIGS. 12A to 12G illustrate, in a sequence of screenshots, another example of operation of the dental charting system, in accordance with some embodiments.

FIG. 16A illustrates, in a screenshot, an example of an anesthetic monitoring input field, in accordance with some embodiments.

DETAILED DESCRIPTION

Embodiments of methods, systems, and apparatus are described through reference to the drawings.

There are several aspects to dentistry, including endodontics (e.g., root canal therapy to save teeth), periodontics (e.g., gum surgery to save teeth), orthodontics (e.g., moving teeth to alleviate a painful, abnormal bite), restorative and prosthodontics (e.g., crowns for working dogs), as well as oral surgery (e.g., extractions of teeth with deep bone infection of sockets). There are at least 180 teeth for a veterinarian to track, including the teeth for dogs, puppies, cats and kittens.

To assist dentists and veterinarians with monitoring teeth, there are international abbreviations for many conditions of teeth and procedures on teeth. It is cumbersome to memorize and retain all of the abbreviations. Moreover, handwritten notes may be sloppy and difficult to read or interpret at a later time.

Animals are often anesthetized while a veterinarian performs dental diagnostics and procedures on their teeth. For the health and safety of the animal, it is desirable to speed the inspection, diagnosis and procedures on teeth while the animal is under an anesthetic.

The teachings describe aspects of a clinical tool (e.g., dental charting system) that may be used by a veterinarian during dental diagnostics and procedures. The use of the clinical tool may reduce risk to a patient (e.g., dog or cat) that is under an anesthetic during the diagnostic and/or procedure. The clinical tool allows for observations to be inputted directly during the diagnostic or procedure. This mitigates error due to illegible handwriting (of an assistant or the veterinarian) that may be sloppy and difficult to read, thereby providing a clearer clinical record that may be easier to read and interpret at a later date.

Figure 1:
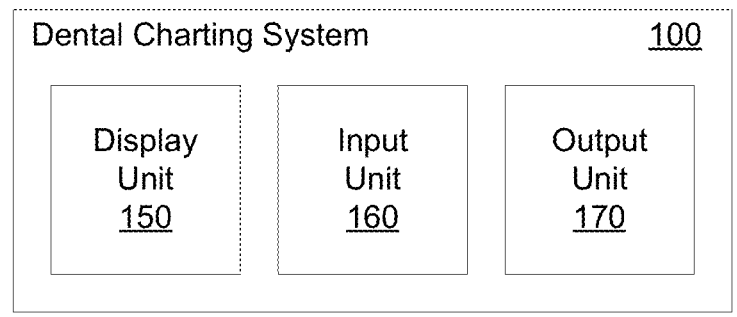
FIG. 1 illustrates, in a component diagram, an example of a dental charting system, in accordance with some embodiments.

FIG. 1 illustrates, in a component diagram, an example of a dental charting system 100, in accordance with some embodiments. The dental charting system 100 comprises a display unit 150 configured to display a quadrant view of a set of teeth, an input unit 160 configured to receive an input for at least one diagnosis or procedure for at least one tooth in the quadrant view, and an output unit 170 configured to generate a dental chart of the set of teeth. The dental chart may be displayed on the display unit 150, printed, or stored in a memory for future viewing.

Figure 2A:
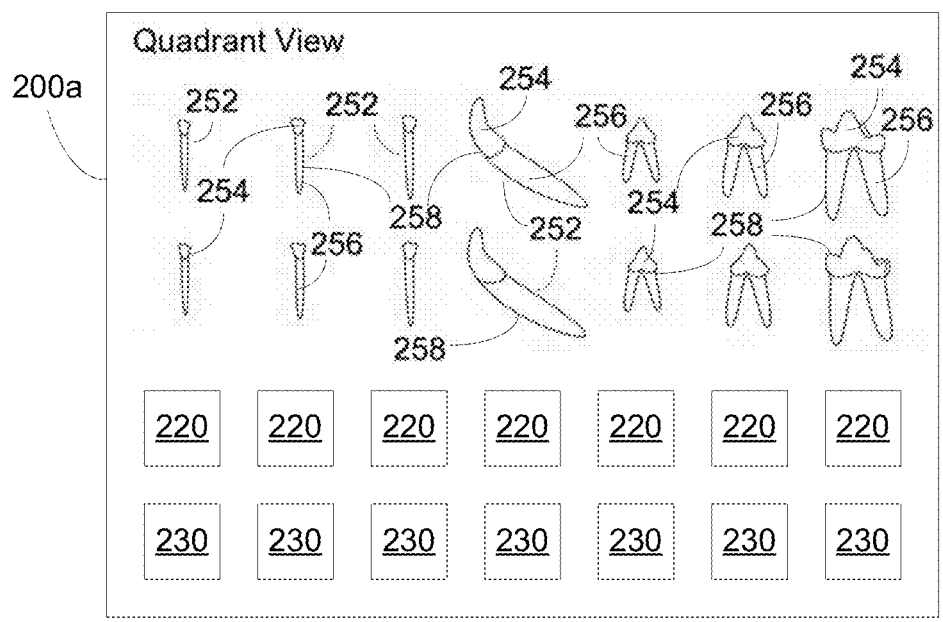
FIG. 2A illustrates, in a component diagram, an example of a quadrant view, in accordance with some embodiments.

FIG. 2A illustrates, in a component diagram, an example of a quadrant view 200a displayed by the display unit 150. The quadrant view 200a comprises a quadrant subset of the set of teeth. Each tooth 252 in the quadrant subset displayed may have separate regions. For example, in some embodiments, each tooth 252 may be displayed showing a root 254, a crown 256 and an outline 258. It is understood that variants to the embodiment may show different regions for different teeth.

The quadrant view 200a may also comprise at least one of a diagnosis field 220 and a procedure field 230 for each tooth 252 in the quadrant subset of teeth. The input unit 170 is configured to receive an input for at least one of the diagnosis field 220 and the procedure field 230 for at least one tooth 252 in the quadrant set of teeth. Each tooth 252 in the set of teeth may be displayed in the dental chart in a color that is associated with the received input for the at least one of the diagnosis field 220 and the procedure field 230. While the embodiment in FIG. 2A illustrates both the diagnosis field 220 and the procedure field 230 for each tooth 252, it should be understood that in other examples only one of the fields 220, 230 may be displayed and that some of the teeth 252 may be displayed with only one or neither of the diagnosis field 220 or the procedure field 230. For example, the display unit 160 may be configured to not display any blank fields in some embodiments.

Upon receiving at least one diagnosis and/or procedure assignment (i.e., selection input received in at least one of the diagnosis field 220 and/or the procedure field 230), to one or more teeth 252 within the quadrant view 200a, the display unit 160 may update the one or more teeth 252 associated with the selection input received in the diagnosis 220 and/or procedure 230 fields. In some embodiments, the update may occur immediately after each individual diagnosis or procedure is assigned, while in other embodiments the update may occur at once for a group of diagnosis and procedure assignments after the system receives an input (e.g., a user clicks an "Apply" button). The update may occur on the quadrant view 200a displayed and/or to the dental chart that is generated. The update will visually reflect the diagnosis and procedure for each tooth 252 within the quadrant 200a.

It is understood that four quadrants may be displayed separately, namely, one quadrant view for each of a right mandible (i.e., right lower jaw), a left mandible (i.e., left lower jaw), a right maxilla (i.e., right upper jaw), and a left maxilla (i.e., left upper jaw) of a patient (i.e., animal). It is also understood that the quadrants may be associated with different animals, such as felines (i.e., cats) and canines (i.e., dogs), and with different sets of teeth for each animal, such as deciduous (i.e., baby or temporary) teeth and permanent (i.e., adult) teeth. The example in FIG. 2A shows a left mandible quadrant view of the deciduous set of canine (e.g., puppy) teeth.

Figures 2B, 3:
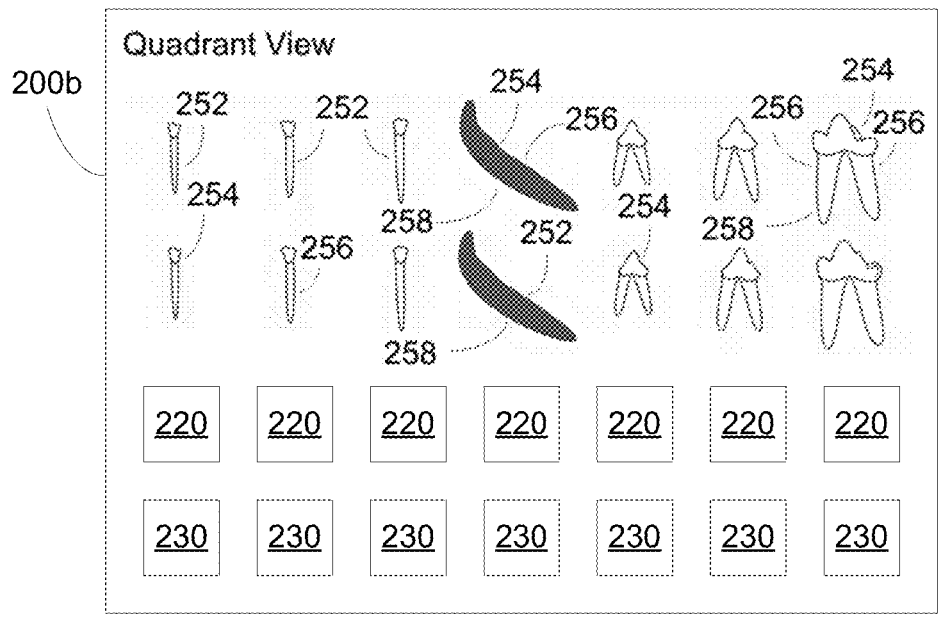
FIG. 2B illustrates, in a component diagram, another example of a quadrant view, in accordance with some embodiments.
FIG. 3 illustrates an example of a data structure for a dental chart diagnosis and procedure abbreviation record, in accordance with some embodiments.

FIG. 2B illustrates in a component diagram, another example of the quadrant view 200b displayed by the display unit 160, in accordance with some embodiments. In this example, a diagnosis that oral surgery is required for a tooth 252 was received as a diagnosis input. In the quadrant view 200b, that tooth is now displayed in a different color (e.g., red) or shading.

The diagnosis and procedure input may be selected from a set of predefined terms or records. FIG. 3 illustrates an example of a data structure for a dental chart diagnosis and procedure abbreviation record 300, in accordance with some embodiments. The abbreviation record 300 may comprise a unique searchable abbreviation field 352, a category field 354, a searchable medical description field 356, a lay description field 358, and four visual aspects 360. In one embodiment, the visual aspects 360 may be related to color, and include a root 362 color, a crown 364 color and an outline 366 color. Other visual aspects may be included, such as an occlusal crown 368 color. In some embodiments, the visual aspects 360 may pertain to different views of each tooth (i.e., mesial or side of tooth towards the middle of the jaw, buccal/labial or front of tooth towards the cheeks/lips, distal or side of tooth away from the middle of the jaw, and palatal or back of tooth towards the palate). Visual processing may include changes to tooth outline color 366, root color 362 and crown color 364. In some embodiments, visual processing may also include semi-transparent fills (e.g., in an occlusal view or view of the chewing plane surface of the teeth) which allows depths of crowns to be shaded and a setting to not influence a region (e.g., a tooth will reflect a previous visual change related to a prior diagnosis or procedure applied). It is noted that diagnosis and procedure inputs in the dental charting system 100 may affect any combination of the crown 256, the root 254, and the outline 258, or there may be no changes to any region whatsoever.

Figure 4:
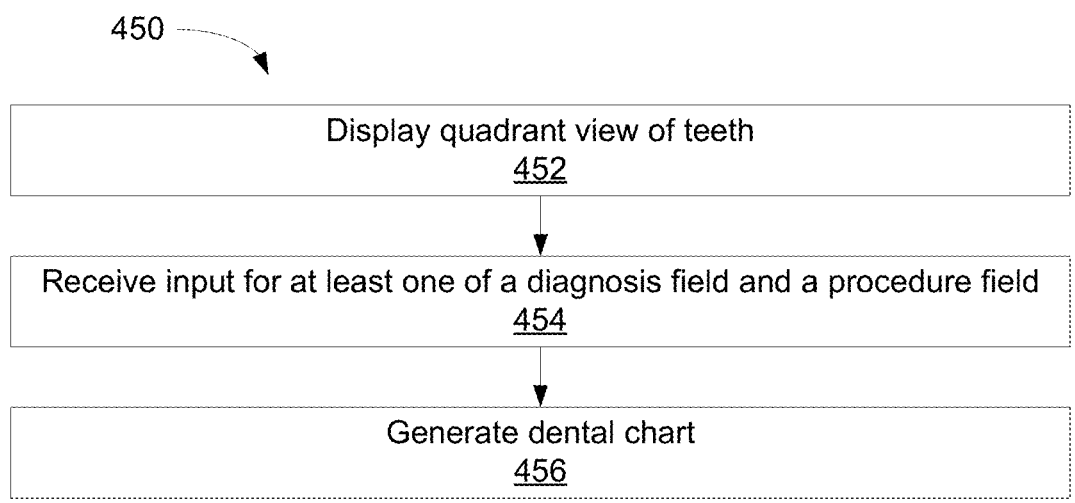
FIG. 4 illustrates, in a flowchart, an example of a method of generating a chart, in accordance with some embodiments.
Figure 5A:
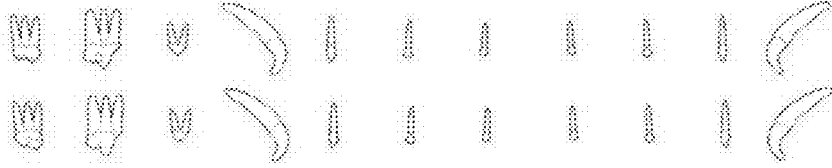
Figure 5B:
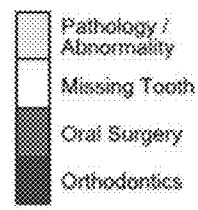
Figure 5D:
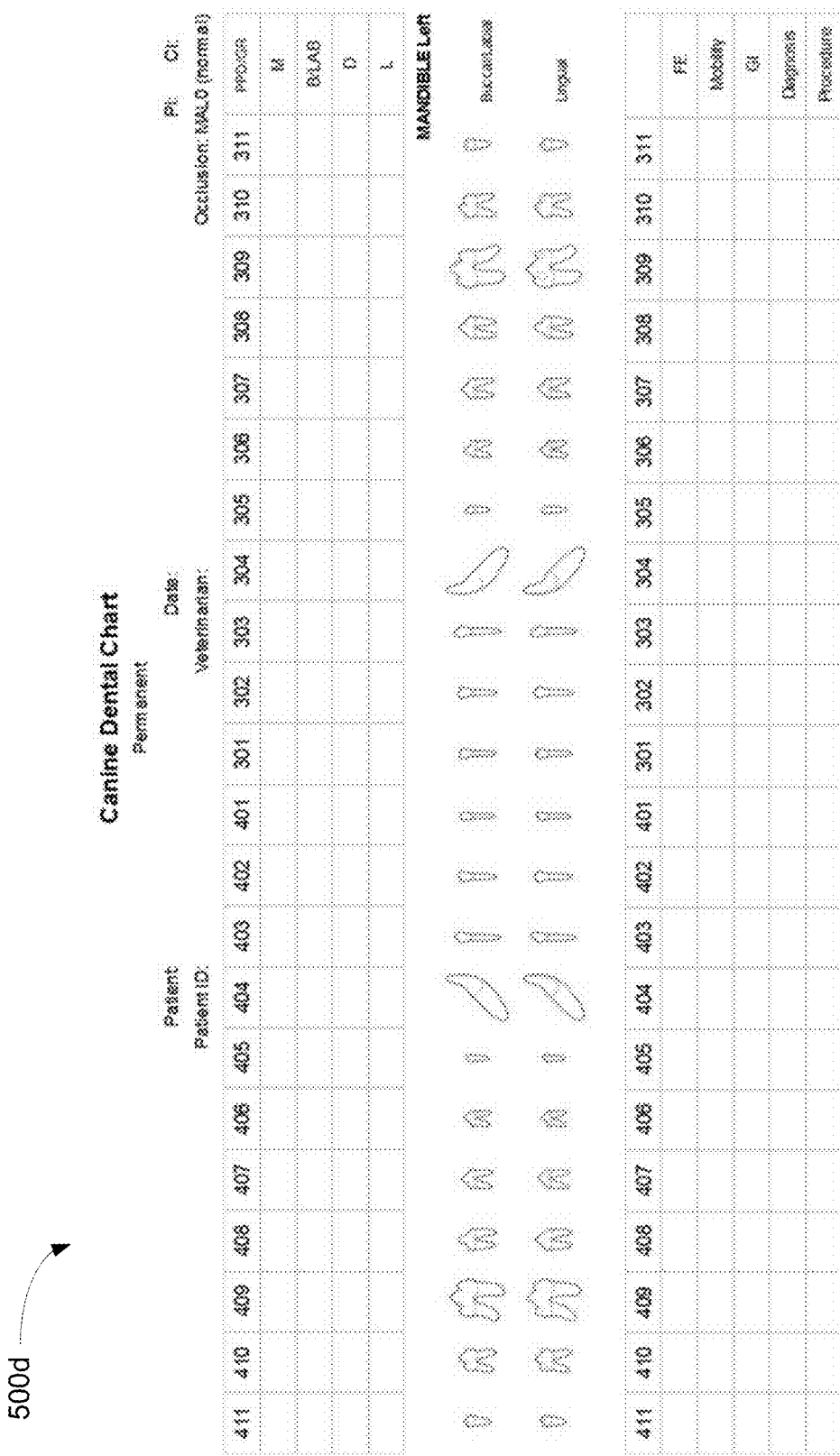
Figure 5E:
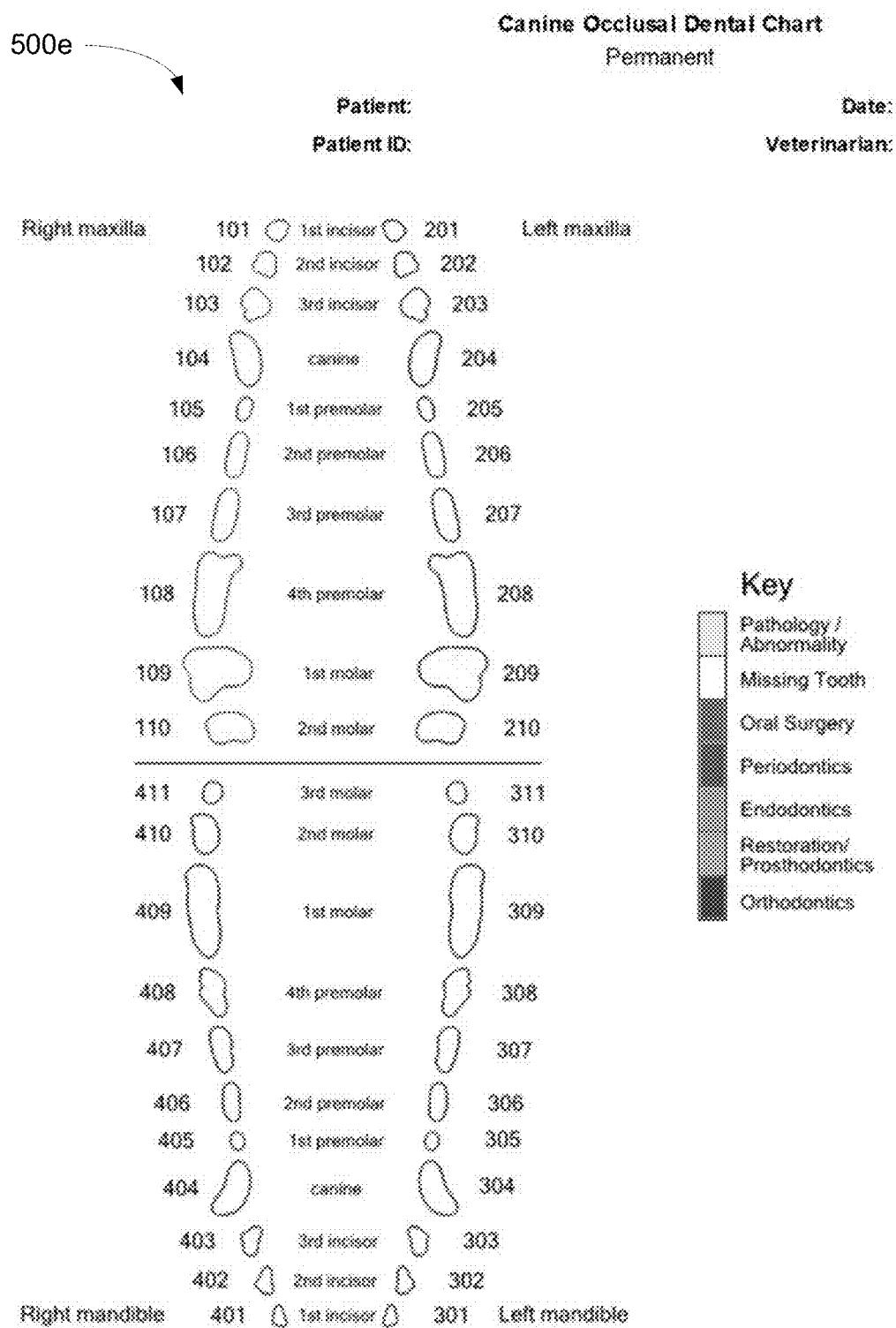
Figure 5H:
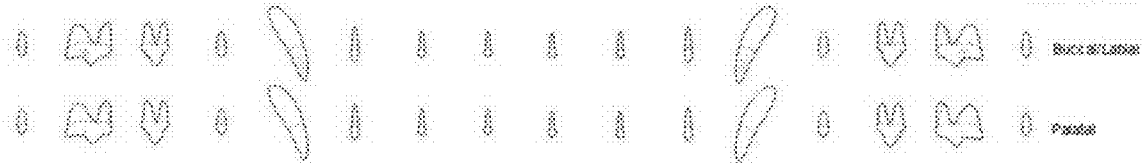
Figure 5I:
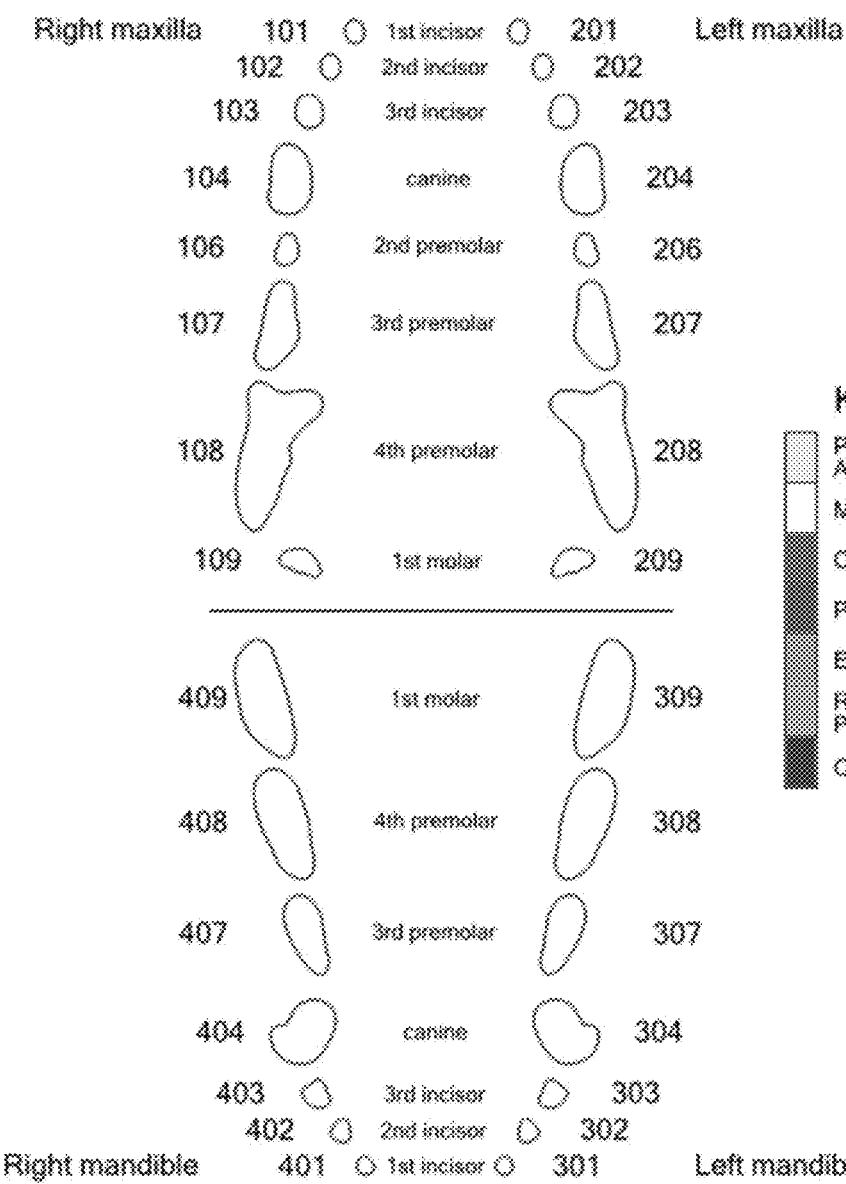
Figure 6A:
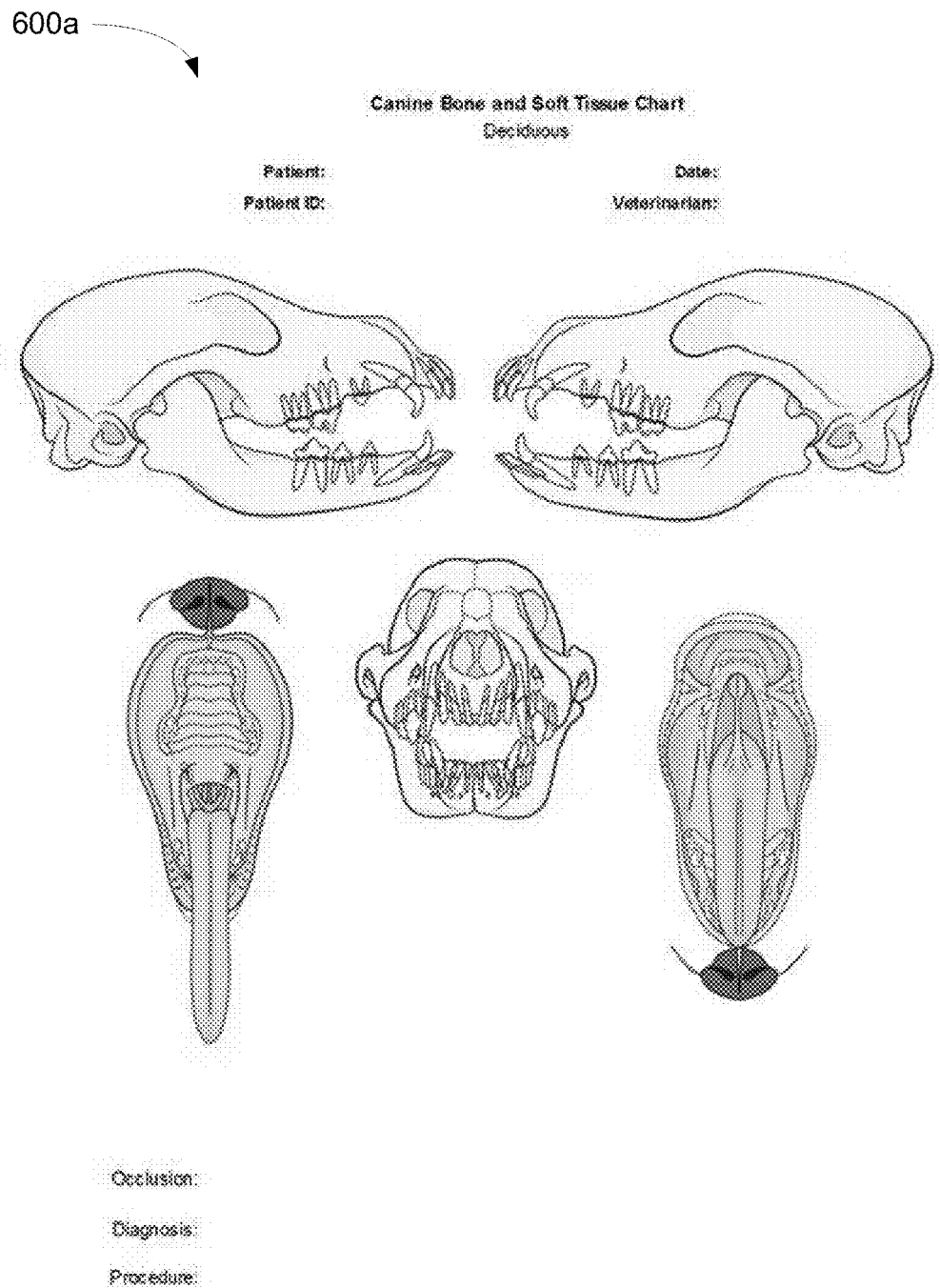
FIGS. 6A to 6D illustrate examples of bone and soft tissue charts, in accordance with some embodiments.
Figure 6B:
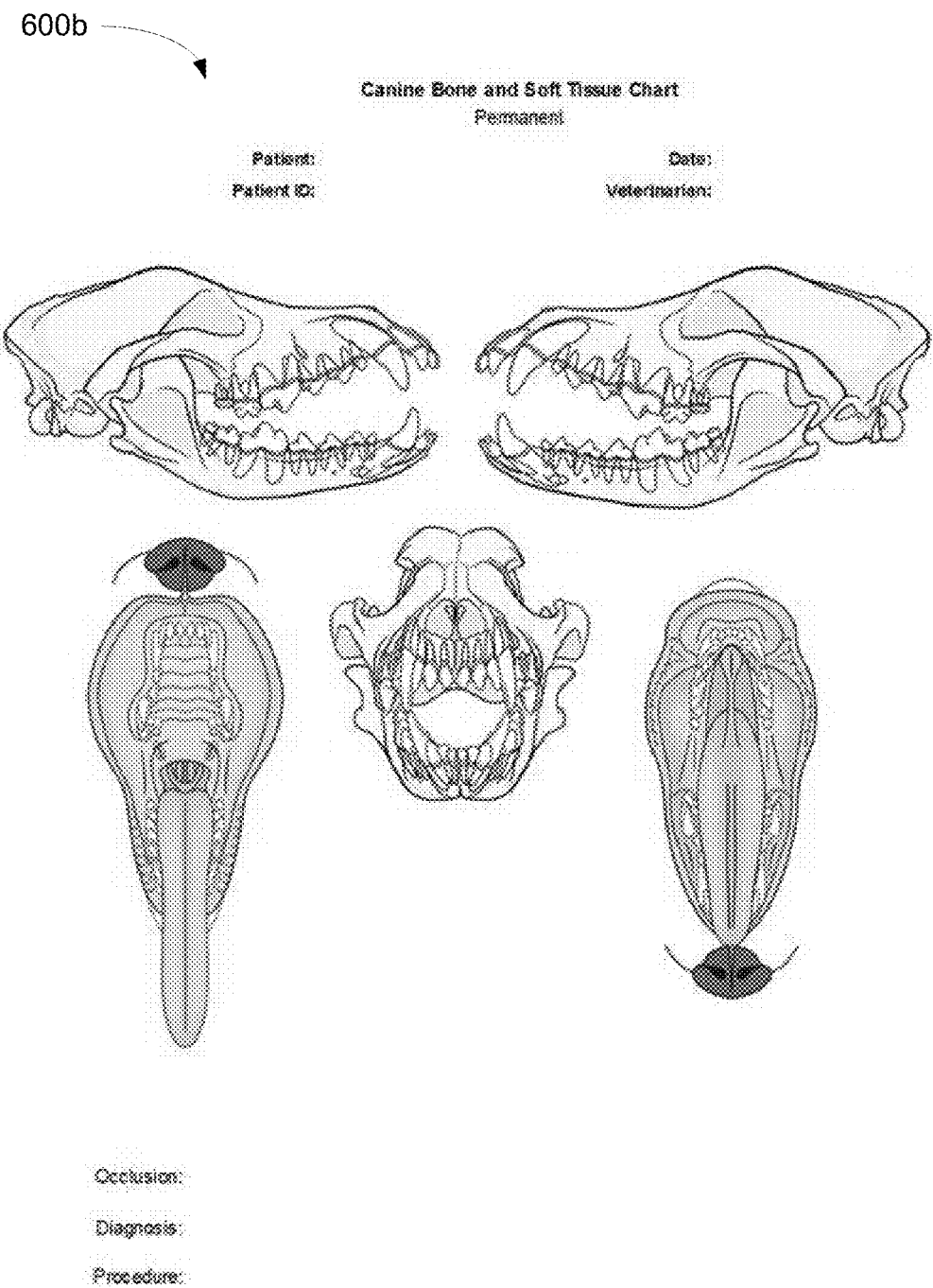
Figure 6C:
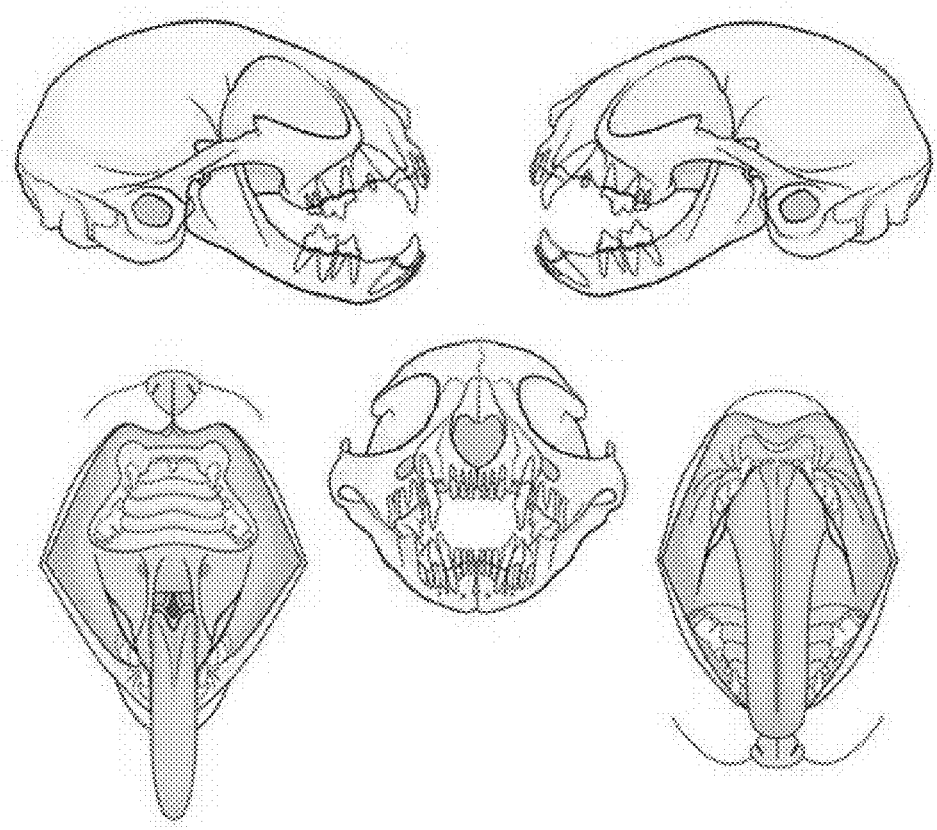
Figure 6D:
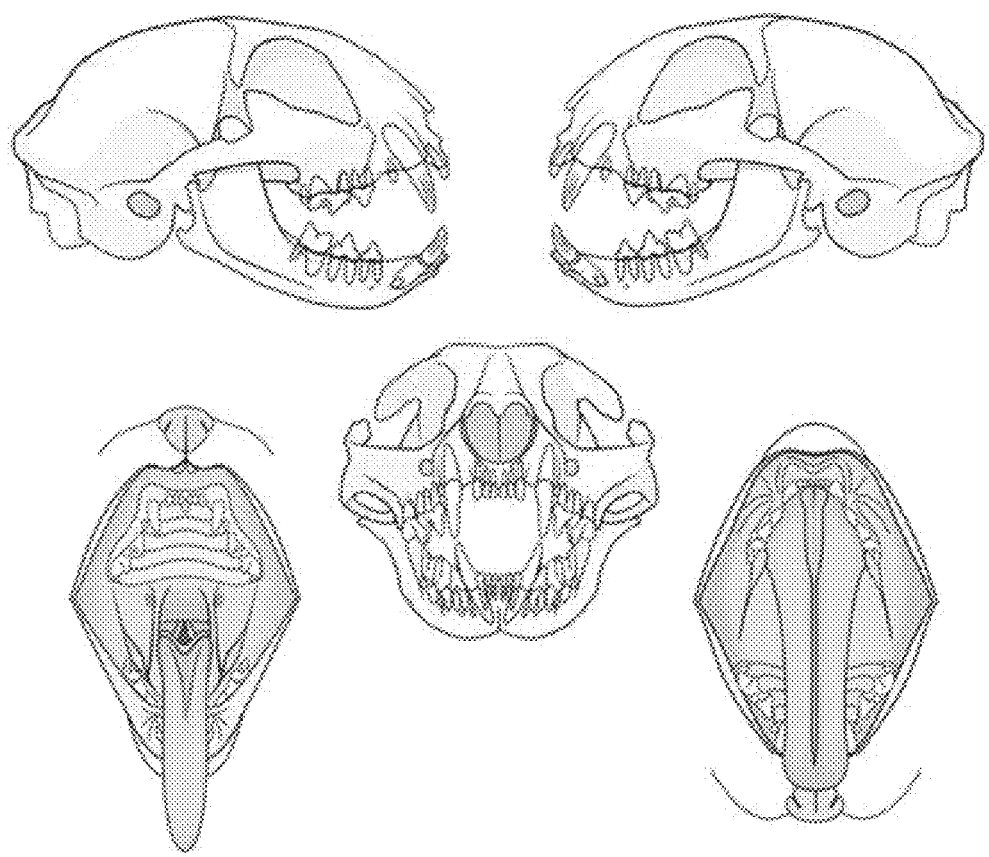

FIG. 4 illustrates, in a flowchart, an example of a method of generating a chart 450, in accordance with some embodiments. The method 450 comprises displaying a quadrant view of a set of teeth 452, receiving an input 454 for at least one of the diagnosis field and the procedure field for at least one tooth in the quadrant set of teeth, and generating a dental chart 456 displaying the set of teeth. The quadrant view comprises a quadrant subset of the set of teeth, and at least one of a diagnosis field and a procedure field for each tooth 252 in the quadrant subset. Each tooth 252 in the quadrant subset displayed has a crown, a root and an outline. Each tooth 252 in the set of teeth is displayed in a color associated with the received input for at least one of the diagnosis field and the procedure field.

Generally, visual representations associated with a diagnosis input and/or a procedure input are based upon the category (e.g., type of diagnosis or type of procedure discipline) assigned to the abbreviation. However, each diagnosis or procedure visualization element may differ, regardless of the category assigned. In some embodiments, the medical categories may be generally assigned visual keys (e.g., color) as shown in Table 1:

TABLE 1

| Medical Category Color Assignment | |
|---|---|
| Medical Category | Color |
| Pathology/Abnormality | YELLOW |
| Missing Tooth | WHITE |
| Oral Surgery | RED |
| Periodontics | PURPLE |
| Endodontics | ORANGE |
| Restoration/Prosthodontics | GREEN |
| Orthodontics | BLUE |

The color yellow for pathology/abnormality may be evocative of a yellow highlighter, the color white may be evocative of a Wite-Out® or other correction fluid that has been applied, the color red may be evocative of blood, the color purple may be evocative of the letter "P" for perio, the color orange may be evocative of gutta percha used as a filing material in root canal therapy, the color green may be evocative of new growth, and the color blue may be evocative of flowing water for tooth movement. It is understood that there may be other medical categories, and that other color assignments may be made to any of the medical categories. Thus, the clinical tool (e.g., system 100) allows for more clarity by showing diagnosis and procedures on teeth in different colors.

FIGS. 5A to 5I illustrate examples of dental charts 500a to 500f, in accordance with some embodiments. Dental chart 500a is for a deciduous set of teeth of a canine (e.g., puppy). Dental chart 500b is an occlusal view chart for the deciduous set of teeth of the canine. Dental chart 500c is for the maxilla of a permanent set of teeth of a canine (e.g., dog). Dental chart 500d is for the mandible of a permanent set of teeth of a canine. Dental chart 500e is an occlusal view chart for the permanent set of teeth of the canine. Dental chart 500f is for a deciduous set of teeth of a feline (e.g., kitten). Dental chart 500g is an occlusal view chart for the deciduous set of teeth of the feline. Dental chart 500h is for a permanent set of teeth of a feline (e.g., cat). Dental chart 500i is an occlusal view chart for the permanent set of teeth of the feline. Each of these charts shows different views of incisors, canine and premolar teeth. In some embodiments, the occlusal view charts show a color key for diagnosis and/or procedures. A color, such as ivory, may be initially assigned to each tooth in a blank chart.

FIGS. 6A to 6D illustrate examples of bone and soft tissue charts 600a to 600d, in accordance with some embodiments. Bone and soft tissue chart 600a is for a deciduous set of teeth of a canine (e.g., puppy). Bone and soft tissue chart 600b is for a permanent set of teeth of a canine (e.g., dog). Bone and soft tissue chart 600c is for a deciduous set of teeth of a feline (e.g., kitten). Bone and soft tissue chart 600d is for a permanent set of teeth of a feline (e.g., cat).

As noted above, the display of the color of teeth in the dental charts 500a to 500i may be modified based on received diagnosis and/or procedure input. In some embodiments, the teeth in the bone and soft tissue charts 600*a* to 600*d* may also change visually (e.g., color) based on received diagnosis and/or procedure input, or by freehand editing as will be described below. In some embodiments, such diagnosis and procedure inputs may be in the form of a selectable abbreviation record 300. In some embodiments, there are 209 dental chart diagnosis and procedure abbreviation records, and 255 bone and soft tissue chart abbreviation records. Such abbreviation records may be stored in a repository, such as a database.

Figure 7A:
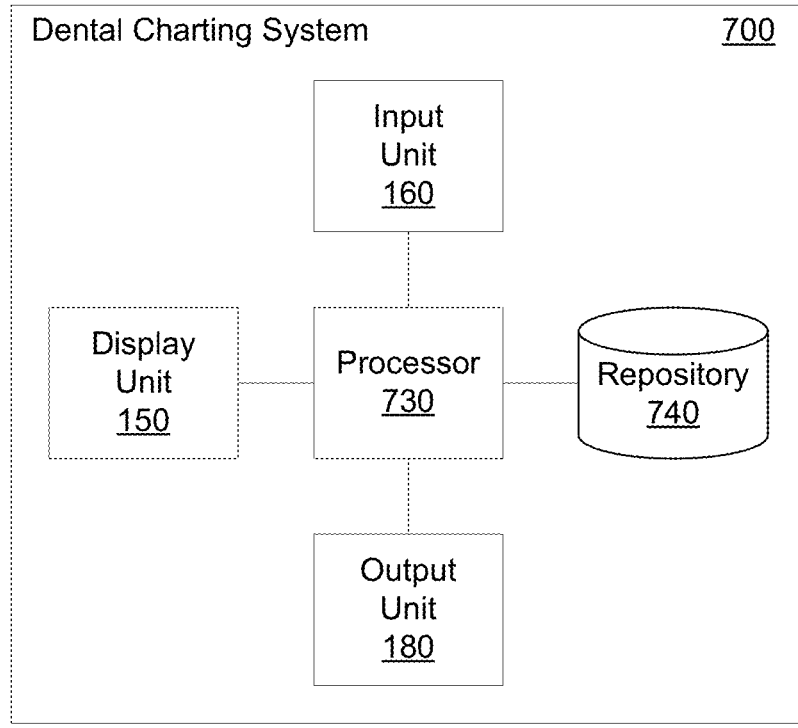
FIG. 7A illustrates, in a component diagram, an example of a dental charting system, in accordance with some embodiments.

FIG. 7A illustrates, in a component diagram, another example of a dental charting system 700, in accordance with some embodiments. The dental charting system 700 comprises the display unit 150, the input unit 160, the output unit 170, a repository 740 for storing records, and a processor 730 for carrying out instructions to operate the dental charting system 700. The repository 740 may store abbreviation records. In some embodiments, the repository 740 may also store patient records (e.g., charts and other patient information), and client records (e.g., owner information), including portions of medical record for veterinary patients. The repository 740 may be located locally on a server or device running the dental charting system 700. Alternatively, the repository 740 or another repository may be located on a server in the cloud. The processor 730 is shown as directing communication between the display unit 150, input unit 160, output unit 170 and repository 740. It is understood that each unit may comprise its own processor. It is also understood that in some embodiments, each unit may communicate directly with the repository 740.

Figure 7B:
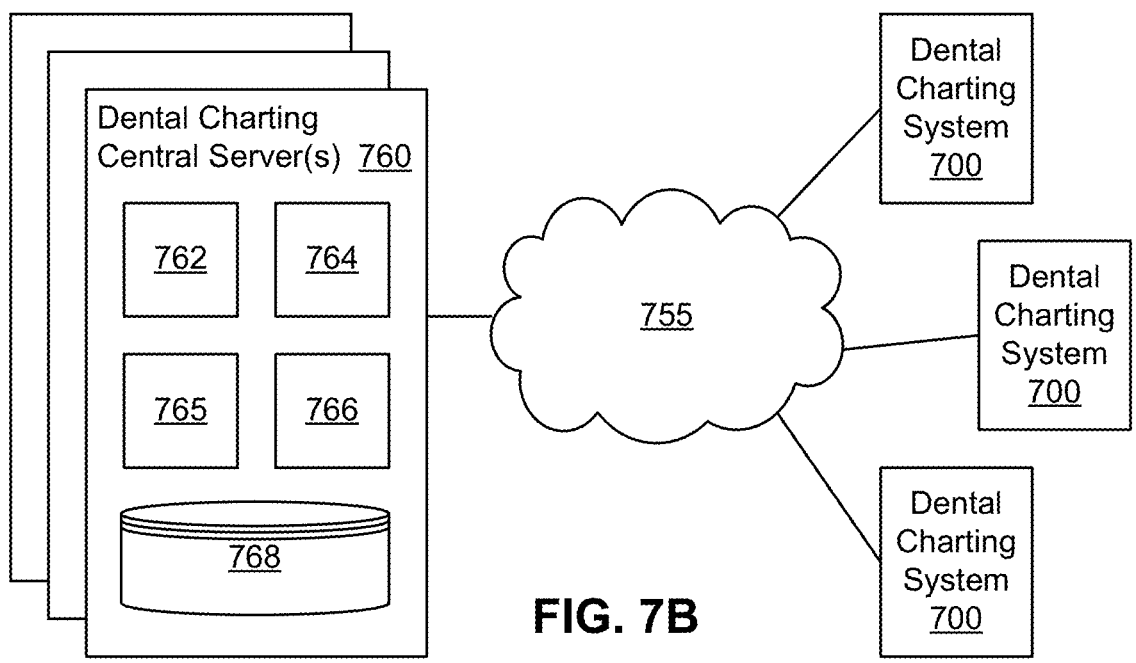
FIG. 7B illustrates, in a component diagram, an example of a dental charting system architecture, in accordance with some embodiments.

FIG. 7B illustrates, in a component diagram, an example of a dental charting system architecture 750, in accordance with some embodiments. The architecture 750 comprises at least one dental charting central server 760 communicating over the Internet 755 to one or more devices and/or server implementing the dental charting system 700. The at least one dental charting central server 760 may comprise an application programming interface (API) 762 used by the dental charting system 700, a practice portal 764 for referring veterinarians, a management portal 765, a billing module 766 and a repository 768. Other components may be added to the at least one dental charting central server 760, including data layer services, security layers, etc. In some embodiments, the records and files of a veterinarian's practice may be stored on the repository 768. The veterinarian may access a patient's file and download a copy via the Internet 755 to a local implementation of the dental charting system 700.

In some embodiments, the dental charting system 700 may also include menu options for a calendar for scheduling patients as well as patient medical history where medical records may be added either locally or online by referring veterinarians on a practice portal 764, such as for patients they are referring. Some menu options may include options for Body Weight, Consultation, Recheck, Master Problem List, Progress Notes, as well as Case Summary. The medical records in the dental charging system 700 may be outputted as documents to view or print in the practice, or to export to any other practice management application. In some embodiments, a menu item for Client may provide the option of an electronic mail to be sent from the server to invite the client to securely view, print, or download selected medical records on a practice portal 764 for his or her own pets. In some embodiments, a menu option for Referring Vet may provide an option of an electronic mail to be sent from the server to invite a referring veterinarian to securely view, print or download selected medical records on a practice portal 764 for patients the veterinarian has referred to the user.

Figure 7C:
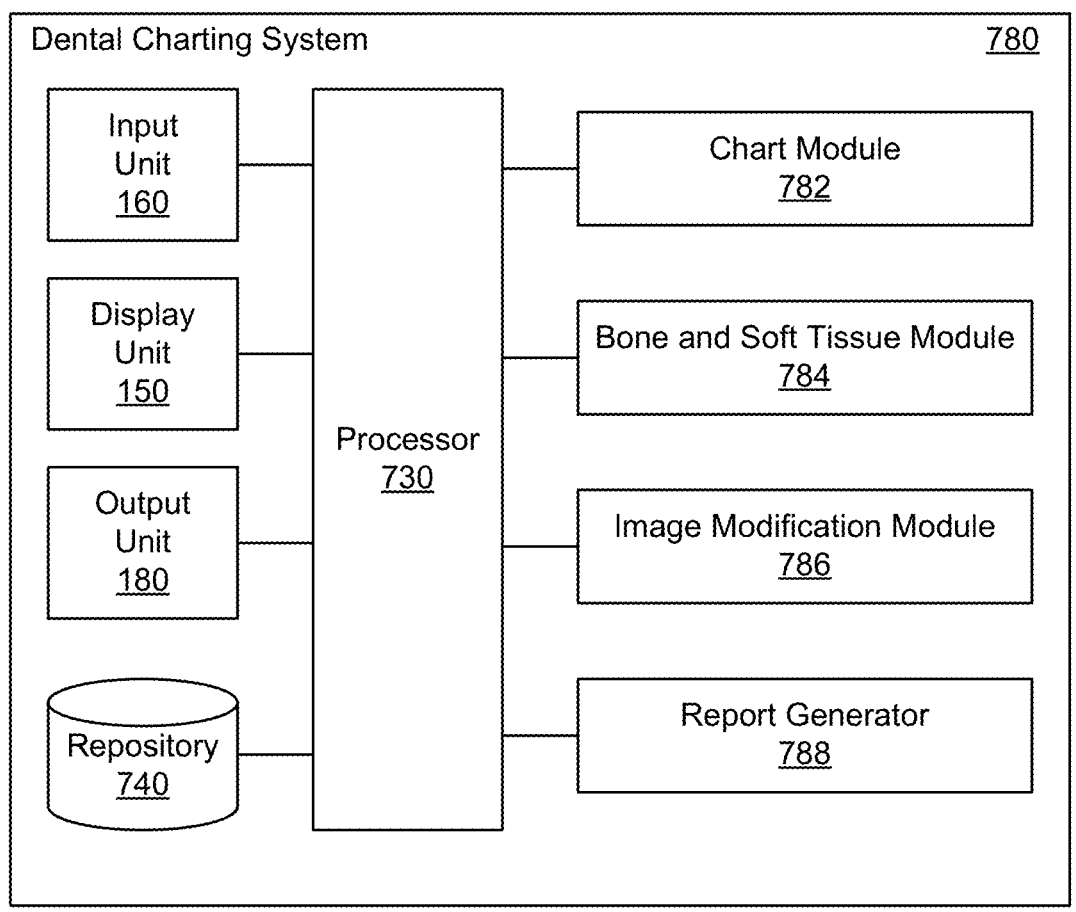
FIG. 7C illustrates, in a component diagram, another example of the dental charting system, in accordance with some embodiments.

FIG. 7C illustrates, in a component diagram, another example of the dental charting system 780, in accordance with some embodiments. The system 780 comprises the display unit 150, the input unit 160, the output unit 180, the processor 730, the repository 740 and a chart module 782 for charting teeth 252, a bone and soft tissue module 784 for charting the bone and soft tissue charts, an image modification module 786 for allowing for manual, freehand, edits to the charts, and a report generator 788 for generating dental charts, technical reports and/or client reports. It is understood that the chart module 782, bone and soft tissue module 784 and image modification module 786 may comprise code stored in a memory of the system 780 and processed by the processor 730.

In some embodiments, to prepare the dental charting system 100, 700, 780, image preparation may be performed to define namespaces (e.g., using XML). In some embodiments, a base set of vector based images may be created for four sets of images for two species (canine and feline) with two different types of teeth (deciduous and permanent). Image sets include each tooth, quadrant view and occlusal view for each combination of species (canine and feline) and type (deciduous and permanent). These images may then be exported to a SVG format. The SVG file text may then be edited using a text editor such that vector drawing commands are grouped, name spaces are added, tooth numbers are added, etc., using an approach that enables programmatic identification and alteration of thickness values, color values and opaqueness. In addition, the entire may be duplicated as Joint Photographic Experts Group (JPG) images, where tooth outline color is lighter and fill colors (ivory) are replaced with white. These sets of images may be used as default (primary) images for manual edits, as described below with reference to FIGS. 9A to 9C.

In some embodiments, vector based namespace coloring may be performed. Vector based images may be loaded as text. Tooth numbers may be identified, namespaces may be found programmatically, and colors and thickness values may be changed, based upon diagnosis or procedure definitions. These definitions define the colors, thickness and opaqueness values of tooth regions (e.g., outline, root, crown, occlusal crown). Vector based images (each tooth, quadrant group and occlusal view) may be hand crafted and altered to include namespaces. Namespaces are used to identify tooth outlines, outline thickness, outline color, crown fill color and root fill color. This approach allows the system 100, 700, 780 to programmatically identify areas or sections of teeth to be colored. Unlike using raster based images, the quality of the final image is better than attempting to paint colors using pixels.

When a new dental chart is created for a patient, the appropriate base of default vector images may be copied to a workspace for the selected patient. These images now become related to the dental chart record related to the patient. From this point on, each tooth, quadrant group and occlusal view groups of images may be manipulated per patient, based upon diagnosis and procedures assigned to each tooth. Depending upon the diagnosis or procedures assigned each of the patients' teeth, the vector image namespaces may be updated (per tooth) at runtime (color, fill, outline, thickness, etc.). The updated "work in process" vector image may then be rendered to a bitmap or jpg image. Corresponding user manual edits may be overlaid (e.g., bitmap based XOR process).

Figure 8A:
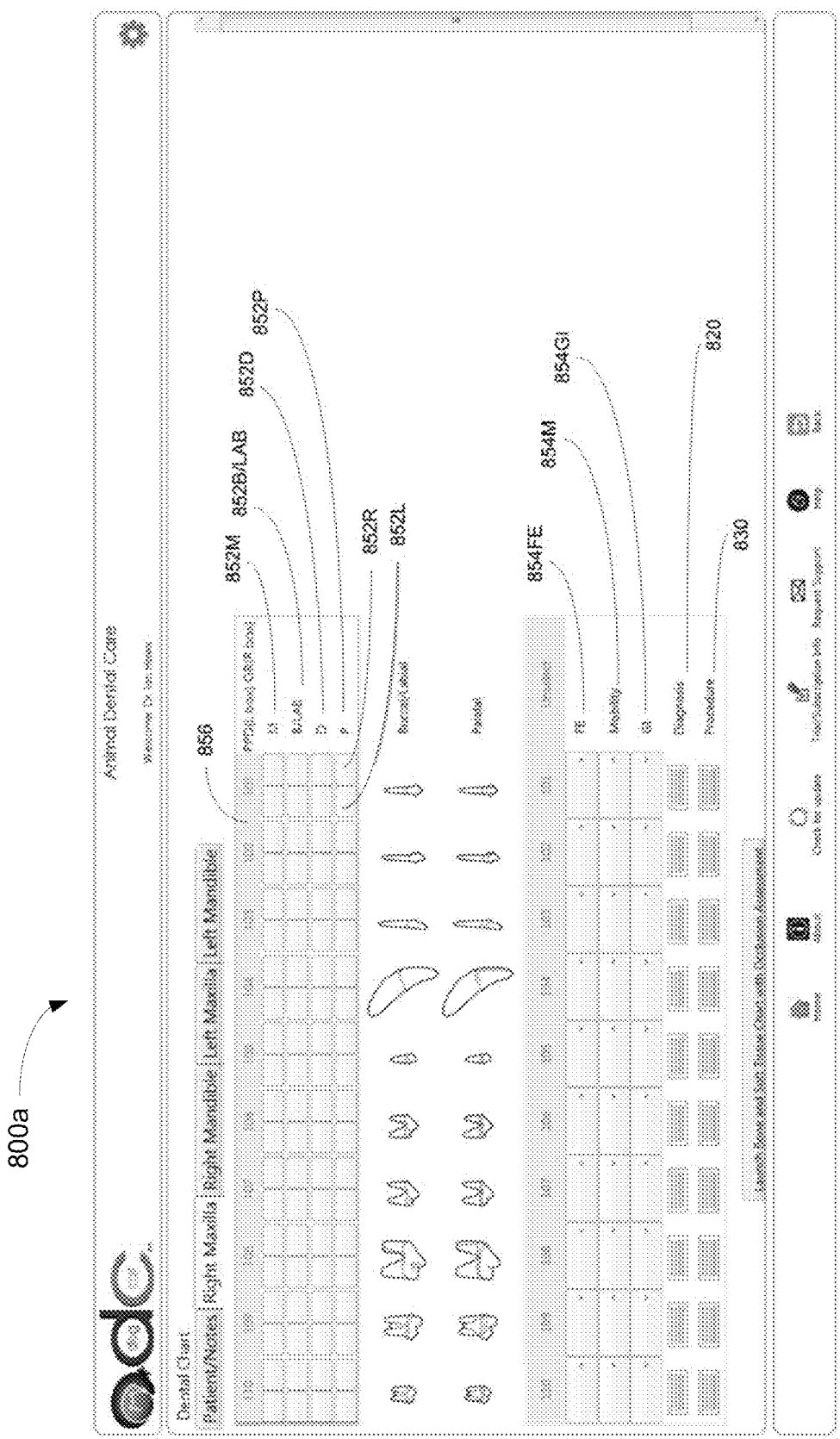

FIGS. 8A to 8E Illustrate, in a sequence of screenshots, an example of the use of the dental charting system 100, 700, 780 in accordance with some embodiments. This example pertains to permanent teeth of a canine (e.g., dog). Other examples may be similarly obtained for canine deciduous teeth (e.g., puppy), feline permanent teeth (e.g. cat) or feline deciduous teeth (e.g., kitten). FIG. 8A illustrates in a screen shot an example of a right maxilla quadrant view 800a, in accordance with some embodiments. This quadrant view 800a includes optional input fields 852 for periodontal measurements above each tooth 252. In this example, each set of input fields 852 are labelled 856 using an international standard tooth numbering convention (e.g., the modified Triadan numbering system). It is understood that other numbering or labels may be associated with each tooth 252.

The periodontal measurements for this example include a clinical periodontal probing depth (PPD) measured in millimetres from the free gingival margin to the base of pocket. In some embodiments, this measurement may be greater than the actual pocket depth if there is a diseased epithelial attachment. The measurement may be received in the left (L) box 852L of the periodontal measurement input fields 852. The right (R) box 852R of the periodontal measurement input fields 852 may be used to receive clinical gingival recession (GR) measured in millimetres from the cementoenamel junction to the free gingival margin. In alternative embodiments, the periodontal measurements may be a clinical periodontal attachment loss (PAL) in the left box 852L and the clinical PPD in the right box 852R for each tooth 252. Either embodiment for the periodontal measurement input fields 852 may be used to store the periodontal measurements for subsequent diagnosis.

In the example shown in FIG. 8A, there are four pairs of periodontal measurement fields 852 for each tooth 252. These four pairs correspond to different views of the teeth. One view is the mesial (M) view 852M or the side portion of the tooth that is towards the midline of the dental arch. Another view is the buccal or labial (B/LAB) view 852B/LAB or outside/front portion of the tooth that is towards the cheek or lip. Another view is the distal (D) view 852D or side portion of the tooth that is away from the midline of the dental arch. Another view is a palatal (P) view 852P or inside/back portion of the tooth that is towards the palate in the maxilla. It is understood that the order of the periodontal measurement input fields 852 may be different in variants of some embodiments. The periodontal measurement data received in the input fields 852 may be stored in a repository record of the patent for future viewing and analysis. The periodontal measurement data may also be time and date stamped to allow a history of periodontal measurement data for a patient to be stored.

The example shown in FIG. 8A also includes periodontal stage input fields 854 for each tooth 252. In this example, three such fields are shown. A furcation exposure (FE) field 854FE is used to receive input in values of stages for a multi-rooted tooth. Table 2 shows an example of stage values for FE:

TABLE 2

Stage values for FE

Value Meaning

1 Soft tissue lesion extending to the furcation level with minimal osseous destruction
2 Osseous destruction at a furcation that permits to probe to enter the TABLE 2-continued Stage values for FE Value Meaning furcation but not pass completely through
3 Osseous destruction as a furcation that permits the probe to pass completely through The example shown in FIG. 8A also includes periodontal stage input fields 854 for each tooth 202. In this example, three such fields are shown. A mobility field 854M is used to receive input in values of stages for individual teeth. Table 3 shows an example of stage values for Mobility:

TABLE 3

Stage values for Mobility

Value Meaning

0 Physiologic mobility up to approximately 0.2 millimeters
1 Mobility increasing in any direction other than axial over a distance of more than 0.2 millimetres and up to approximately 0.5 millimeters
2 Mobility increasing in any direction other than axial over a distance of more than 0.5 millimetres and up to approximately 1.0 millimetres
3 Mobility increasing in any direction other than axial over a distance exceeding 1.0 millimetres or any axial movement The example shown in FIG. 8A also includes periodontal stage input fields 854 for each tooth 252. In this example, three such fields are shown. A gingivitis index (GI) field 854GI is used to receive input in values of stages for individual teeth. Table 4 shows an example of stage values for GI:

TABLE 4

Stage values for GI

Value Meaning

0 Normal gingiva
1 Mild inflammation, slight change in color, slight edema, no bleeding on probing
2 Moderate inflammation, redness, edema, bleeding on probing
3 Severe inflammation, marked redness, edema, ulceration, tendency to spontaneous bleeding It is understood that the order of the periodontal stage input fields 854 may be different in variants of some embodiments. Moreover different and/or other periodontal stage categories may be used. The periodontal stage data received in the input fields 854 may be stored in a repository record of the patent for future viewing and analysis. The periodontal stage data may also be time and date stamped to allow a history of periodontal stage data for a patient to be store. In this example, a mobility stage value input of "0" and a GI stage value input of "3" was received.

Figure 8B:
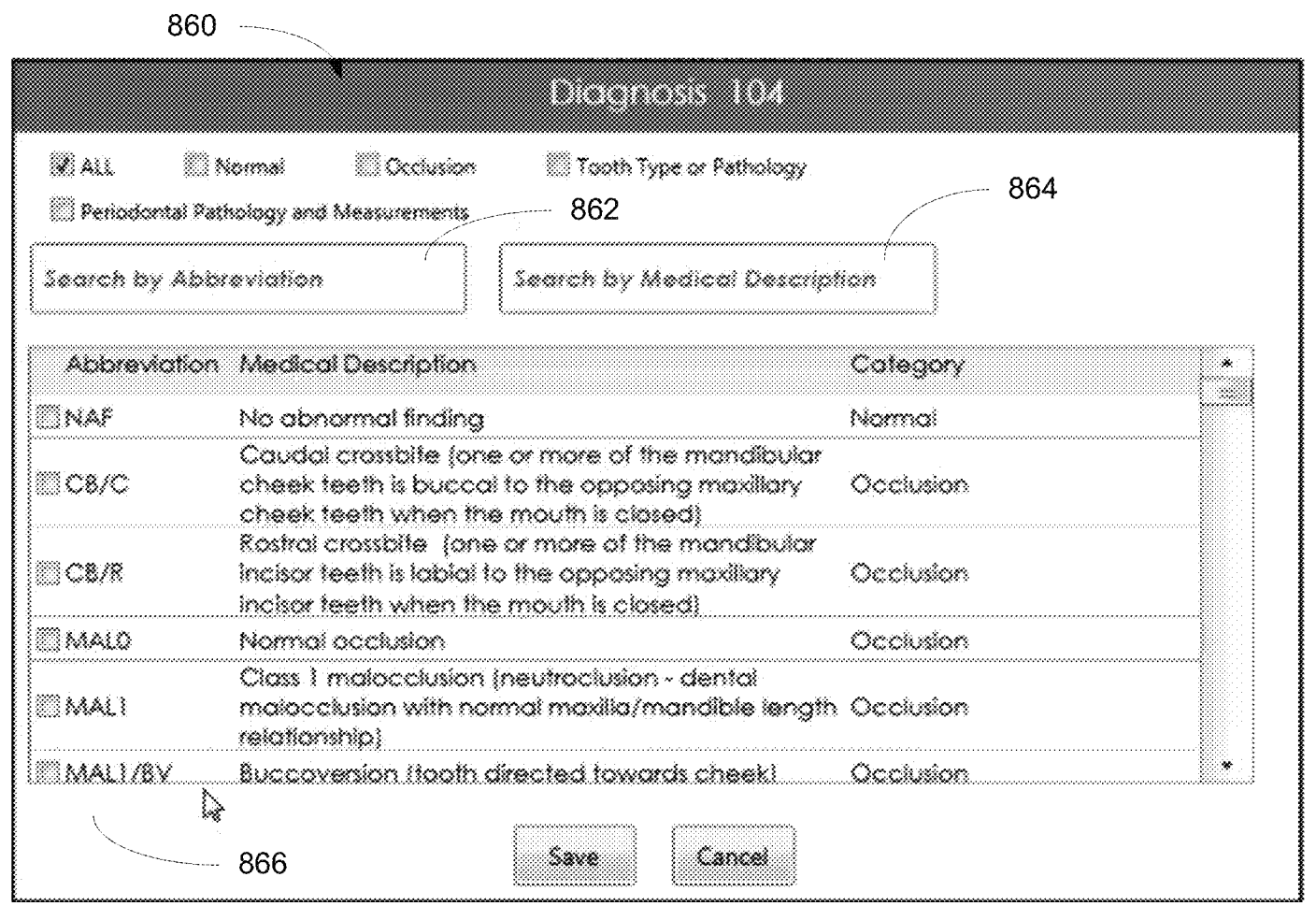

The example shown in FIG. 8A also includes a diagnosis field 220 and a procedure field 230 for each tooth 252. The diagnosis field 220 may receive a diagnosis input. In some embodiments, an input selecting the diagnosis icon 220 may result in a pop up dialog box. FIG. 8B illustrates in a screenshot an example of a diagnosis selection dialog box 860. The diagnosis selection dialog box includes an abbreviation search input field 862, a medical description search input field 864, and a listing of diagnosis abbreviation values

866. A user may scroll down the listing of diagnosis abbreviation values 866 or take advantage of the search input fields 862, 864.

Figure 8D:
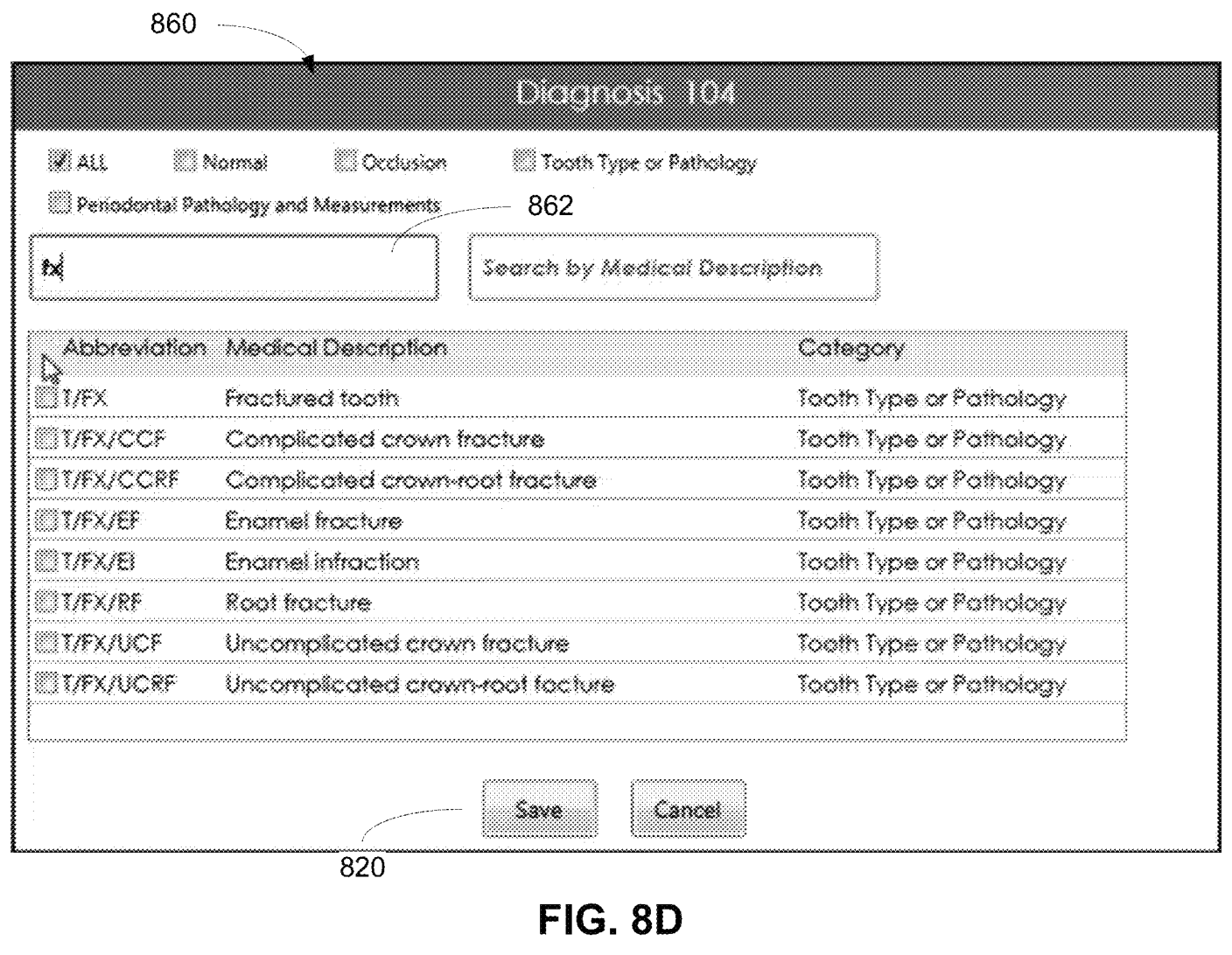
Figure 8E:
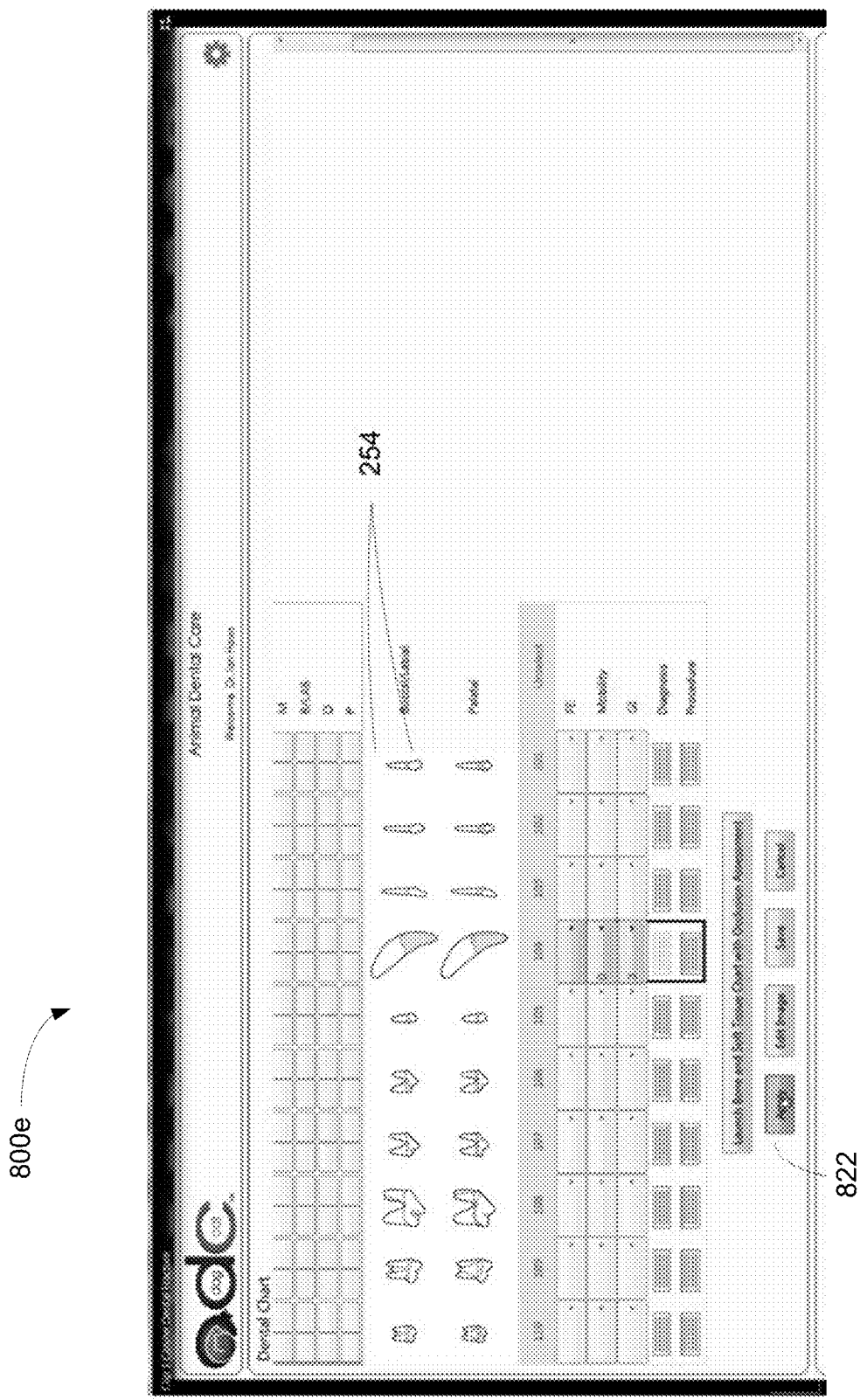

FIG. 8C illustrates, in another example of the diagnosis selection dialog box 860, the selections that appear when the medical description search input field 864 receives an input of "fra". FIG. 8D illustrates, in another example of the diagnosis selection dialog box 860, the selections that appear when the abbreviations search input field 862 receives an input of "fx". In this case, a user has selected the diagnosis "T/FX/CCF" which is a universal standard abbreviation for "Complicated crown fracture". In this example, the diagnosis selection is received when the user selects the "save" button 820. The diagnosis field 220 is highlighted in a color that the tooth (in this example, tooth 104) will be modified after an "Apply" button 822 selection is received. FIG. 8E illustrates, in a screenshot, another example of the quadrant view 800e showing the crown 254 colored (e.g., in yellow) or shaded (that signifies a pathology/abnormality condition; see Table 1 above).

In some embodiments, freehand editing of teeth in the quadrant may be performed by drawing lesions, fractures, chips, or any other notations, as well as adding text using a complement of common painting tools, such as pencils, brushes and line widths. Upon receiving the manual editing input, the manual edits may be transparently overlaid onto the programmatically visualized quadrant image. In some embodiments, if additional diagnoses or procedures inputs are received (including the input to remove a diagnosis or procedure) from the quadrant, when the additional diagnoses or procedures are applied, the manual editing may still be transparently overlaid on to the updated programmatically visualized quadrant. It is desirable to be able to modify the color of the teeth 252 as applicable without having to regenerate the manual entry. I.e., the animal dental system 100, 700, 780 allows for both the coloring of teeth 252 based on diagnoses and/or procedures, and manual entry of marking on the teeth 252. Thus, allowing for quicker note taking during diagnoses and/or procedures by a veterinarian while the patient (e.g., dog or cat) is under an anesthetic. The clinical tool (e.g., system 100, 700, 780) also allows for contemporaneous diagnosis and procedures which may lead to more accurate clinical records and animal care (e.g., no misinterpretations between diagnosis and procedure).

Figure 9A:
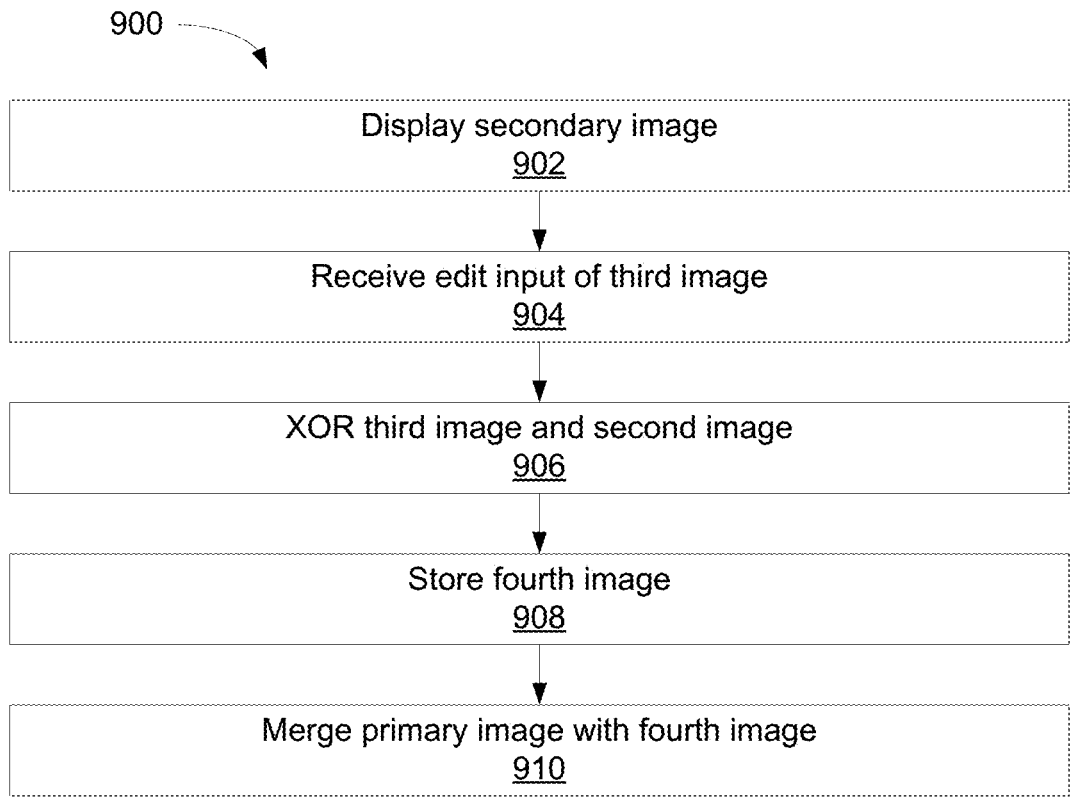
FIG. 9A illustrates, in a flowchart, an example of a method of tooth image editing, in accordance with some embodiments.
Figure 9B:
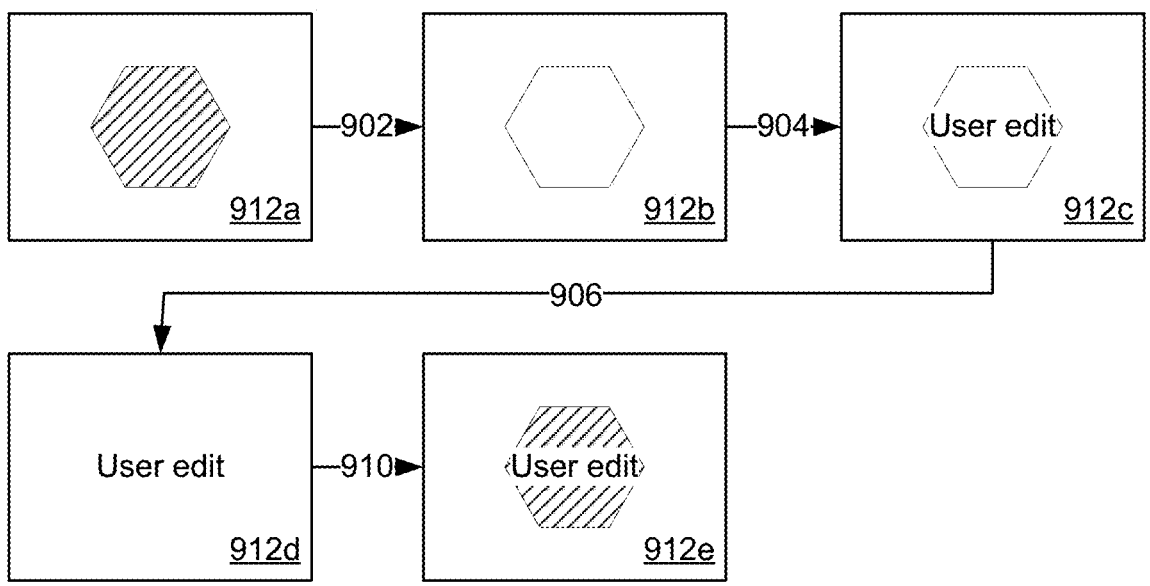
FIG. 9B illustrates an example of an image processed using the method of FIG. 9A, in accordance with some embodiments.

FIG. 9A illustrates, in a flowchart, an example of a method of tooth image editing 910, in accordance with some embodiments. FIG. 9B illustrates an example of an image processed using the method 900 of FIG. 9A, in accordance with some embodiments. The method 900 may be performed by the processor 730 implementing the image modification module 786. The method 900 comprises displaying 902, a secondary image 912b for the tooth, quadrant or view that is desired to be modified. In some embodiments, the secondary set of images do not have colored fills and the tooth outlines are lighter. In some embodiments, a bitmap based editing tool may be used to mark up the image. Thus, an edit input is received 904 that produces a third image 912c for the tooth, quadrant or view that is desired to be modified. Next the third image 912c and the secondary image 912b are XOR'd 906 such that a fourth image 912d comprises only the manual input. The fourth image 912d may be stored 908 in an appropriate location of the repository 740. Optionally, the primary image 912a for the tooth, quadrant or view may have been updated (i.e., colored) based on an assigned diagnosis or procedure (as described above). The primary image 912a is merged 910 with the fourth image 912d into merged image 912e. Other steps may be added to the method 900, such as converting the merged image 912e to a JPG or BITMAP image (for high quality final images), displaying the merged image 912e in a user interface by the display unit 150, and including the merged image 912e in charts and reports.

Figure 9C:
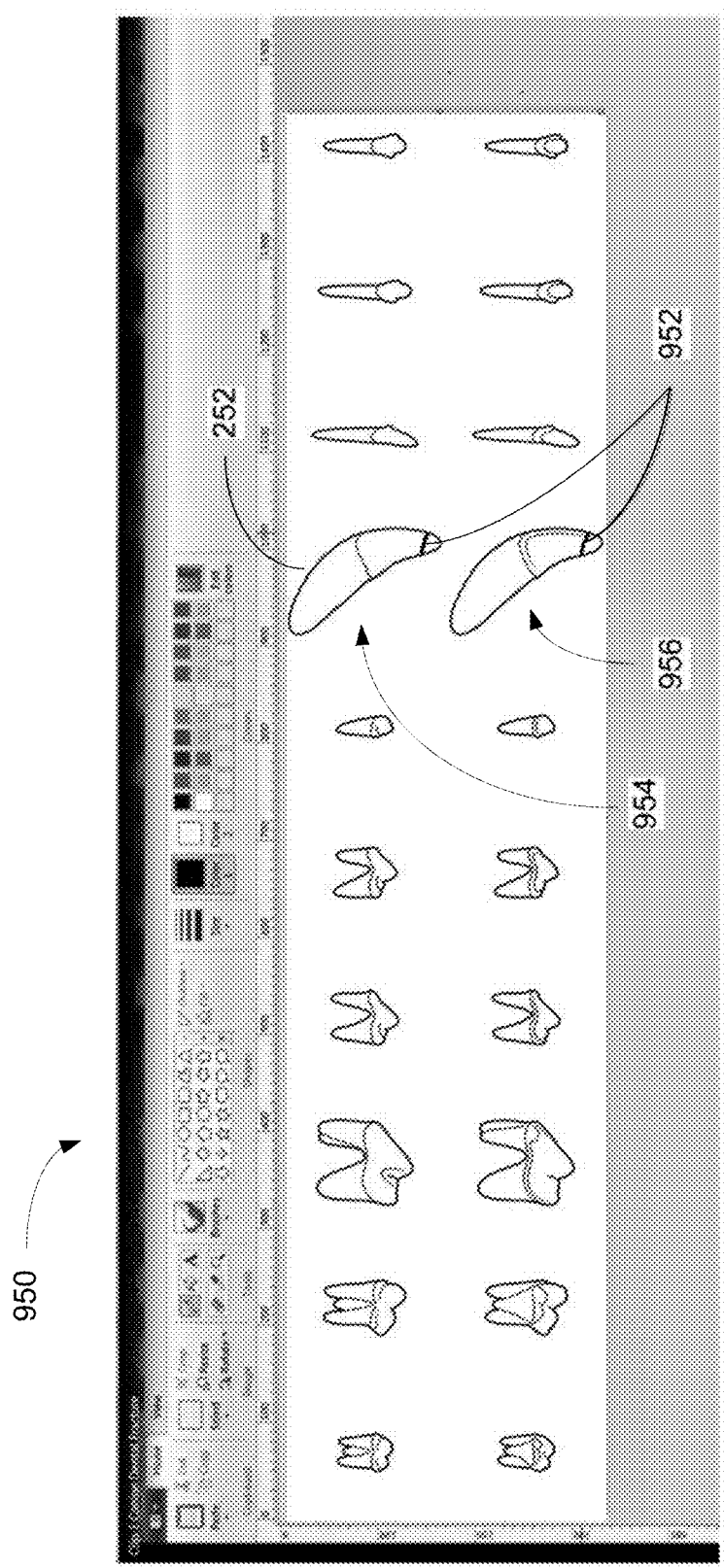
FIG. 9C illustrates in a screenshot an example of an image modification module that may be used to freehand edit a tooth, in accordance with some embodiments.

FIG. 9C illustrates in a screenshot an example of an image modification module 786 tool 920 that may be used to freehand edit a tooth 252, in accordance with some embodiments. In this example, a fracture line 922 is inserted on the crown 254 of tooth 104 that was diagnosed with a fracture in the example above. Both the buccal/labial 924 and palatal 926 views are shown.

Figure 9D:
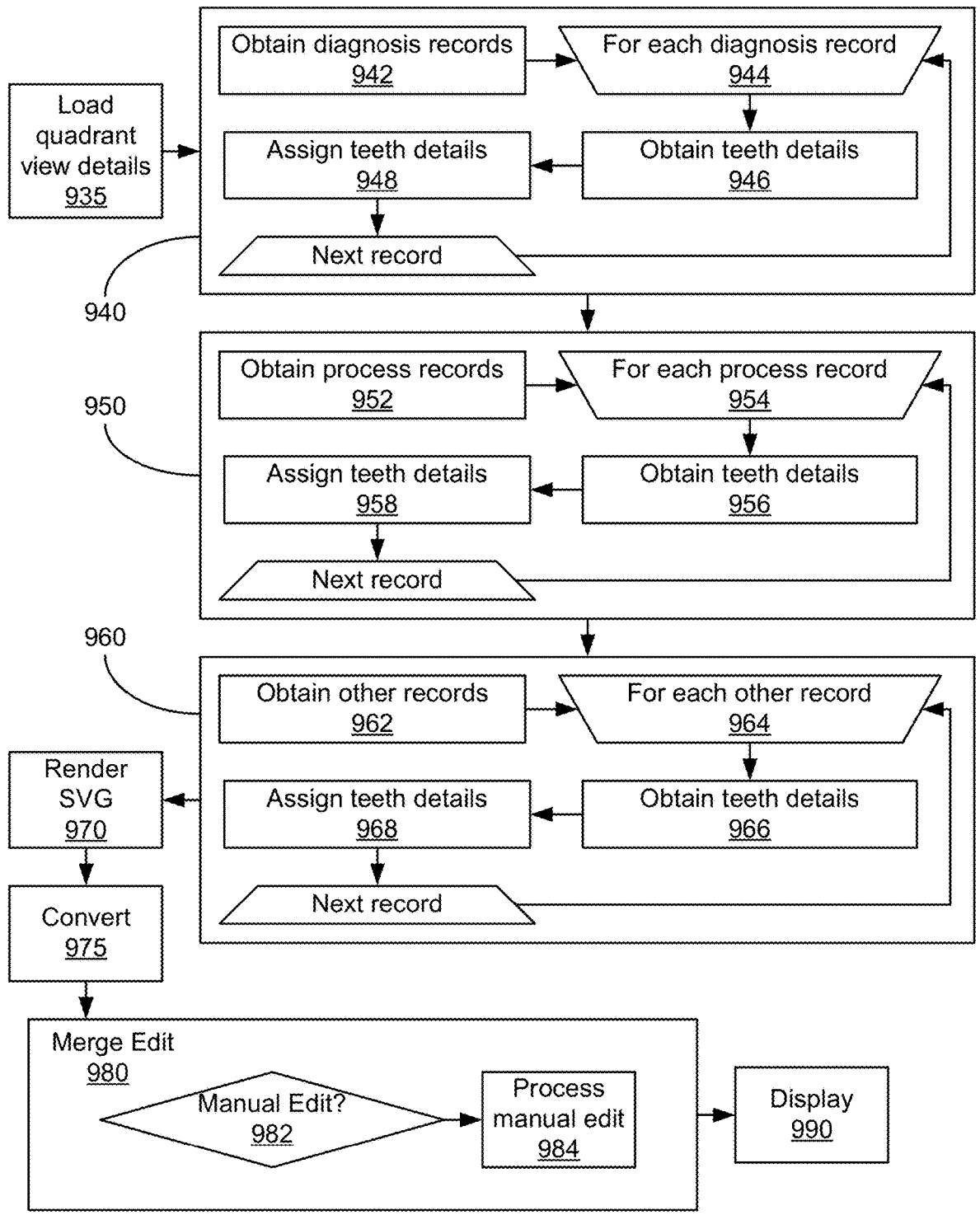
FIG. 9D illustrates, in a flowchart, an example of a method 930 of processing a quadrant view, in accordance with some embodiments.

FIG. 9D illustrates, in a flowchart, an example of a method 930 of processing a quadrant view, in accordance with some embodiments. The method 930 may be used to apply diagnosis and procedure medical records assigned to quadrant teeth, inclusive of tooth parts (crowns, roots and outline) and to apply manual edit merging. The method 930 comprises loading 935 a default quadrant view, processing 940 diagnosis records, processing 950 procedure records, processing 960 other records, rendering 970 a scalable vector graphic (SVG), converting 975 the rendered SVG into a JPG, merging 980 an overlay into a combined new single JPG image, and refreshing 990 the user interface to display the updated graphic. Other steps may be added to the method 930.

In some embodiments, the loaded 935 quadrant view may comprise a hybrid XML wrapped vector based quadrant view of images. As described above, the quadrant view of images may comprise the left or right maxilla, or left or right mandible of a canine or feline species, and may be of deciduous or permanent teeth types.

In some embodiments, the diagnosis processing 940, may comprise obtaining 942 diagnosis records applied to the loaded quadrant view, ordered by entry order. For each filtered and ordered diagnosis record 944 pertinent to the loaded quadrant, teeth details are obtained 946 and assigned 948. For example, for each tooth, a tooth number may be determined and teeth paths (crowns, roots, outline) may be selected, each of which may have a color, opacity and thickness properties. Teeth paths (crowns, roots, outlines) color, opacity and thickness properties are assigned 958 as inherited by the diagnosis definition record.

In some embodiments, the procedure processing 950, may comprise obtaining 952 procedure records applied to the loaded quadrant view, ordered by entry order. For each filtered and ordered procedure record 954 pertinent to the loaded quadrant, teeth details are obtained 956 and assigned 958. For example, for each tooth, a tooth number may be determined and teeth paths (crowns, roots, outline) may be selected, each of which may have a color, opacity and thickness properties. Teeth paths (crowns, roots, outlines) color, opacity and thickness properties are assigned 958 as inherited by the procedure definition record.

In some embodiments, the other processing 960, may comprise obtaining 962 diagnosis records applied to the loaded quadrant view, specifically of TBT or XSS diagnosis type. Such types are processed last. For each filtered special case diagnosis record 964 pertinent to the loaded quadrant, teeth details are obtained 966 and assigned 968. For example, for each tooth, a tooth number may be determined and teeth paths (crowns, roots, outline) may be selected, each of which may have a color, opacity and thickness properties. Teeth paths (crowns, roots, outlines) color, opacity and thickness properties are assigned 958 as inherited by the special case diagnosis definition record.

In some embodiments, the quadrant of teeth may be rendered 970 as a single SVG graphic by extracting SVB teeth images to render a standard combined SVG image. Once converted 975, if there are manual edits 982 for the quadrant, an overlay may be merged 984 into a combined new single JPG image (for example, as described above with reference to FIGS. 9A to 9C).

Figure 10A:
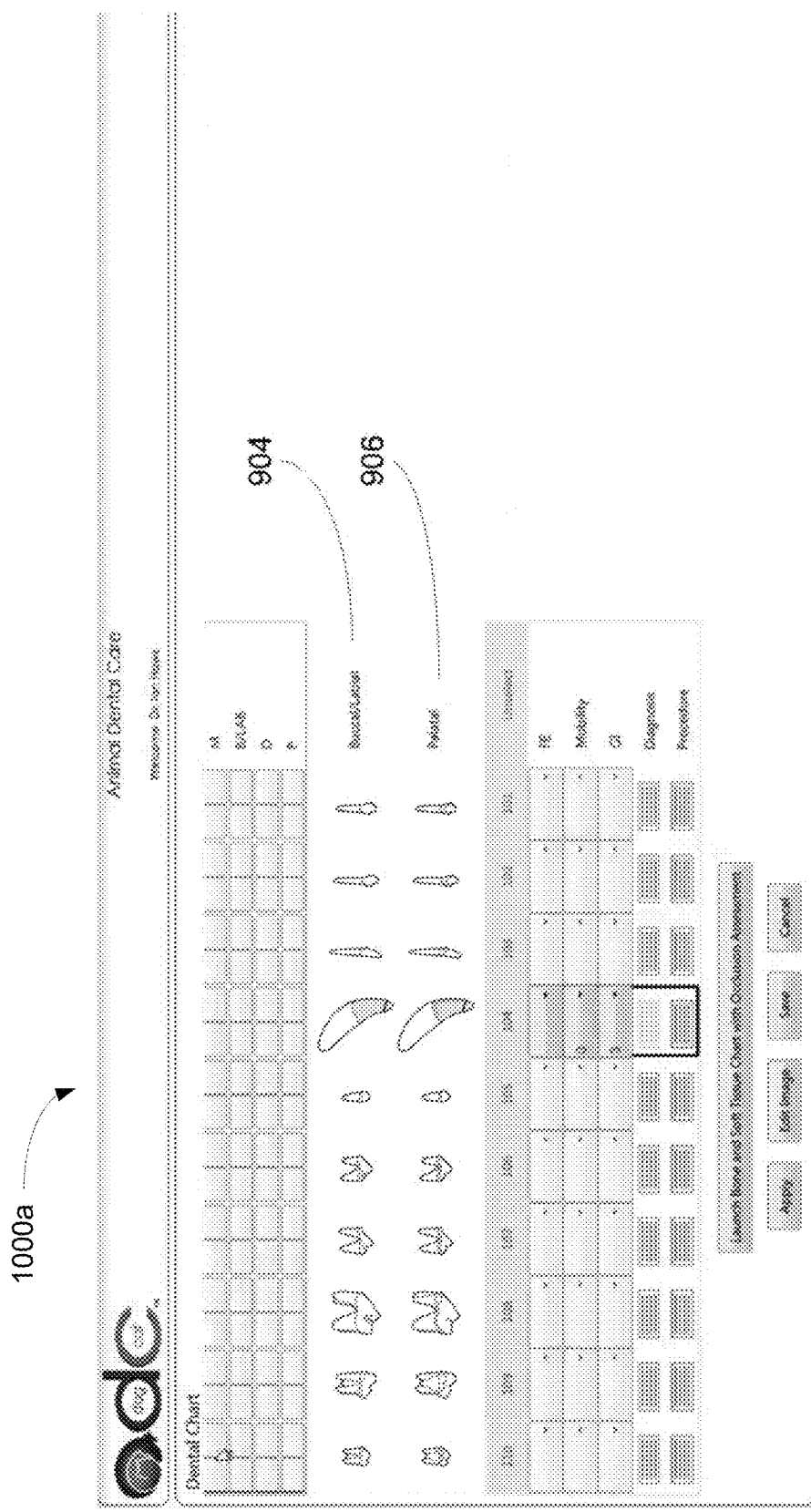
FIG. 10A illustrates in a screenshot another example of the right maxilla quadrant view, in accordance with some embodiments.
Figure 10B:
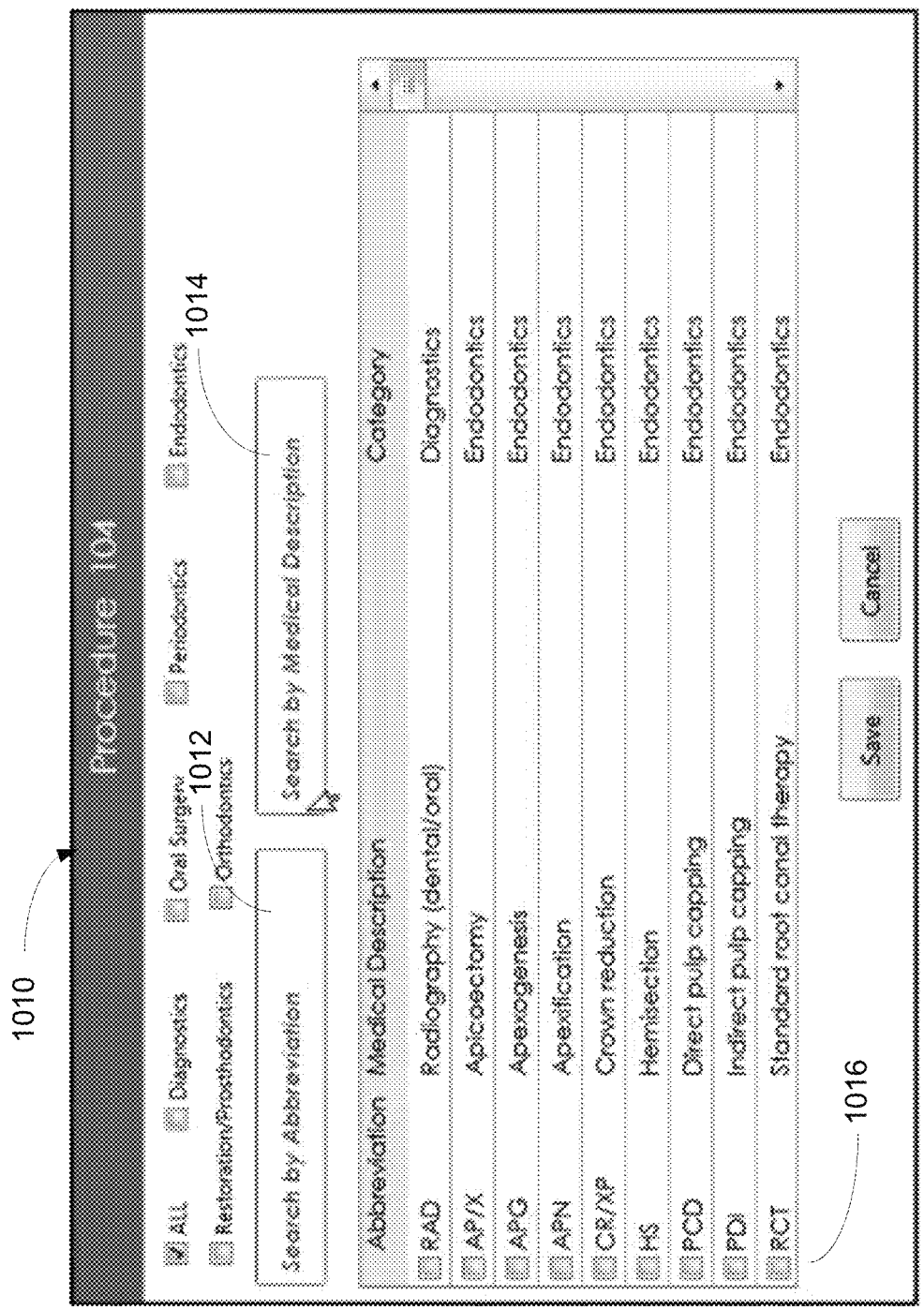
FIG. 10B illustrates in a screenshot an example of a procedure selection dialog box, in accordance with some embodiments.

FIG. 10A illustrates in a screenshot another example of the right maxilla quadrant view 1000a, in accordance with some embodiments. In this view, both buccal/labial 924 and palatal 926 views of the crown on the 104 tooth are colored (e.g., in yellow) or shaded, and show the fracture line 922. In some embodiments, an input selecting the procedure icon 230 may result in a pop up dialog box. FIG. 10B illustrates in a screenshot an example of a procedure selection dialog box 1010, in accordance with some embodiments. The procedure selection dialog box 1010 includes an abbreviation search input field 1012, a medical description search input field 1014, and a listing of procedure abbreviation values 1016. A user may scroll down the listing of procedure abbreviation values 1016 or take advantage of the search input fields 1012, 1014.

Figure 10C:
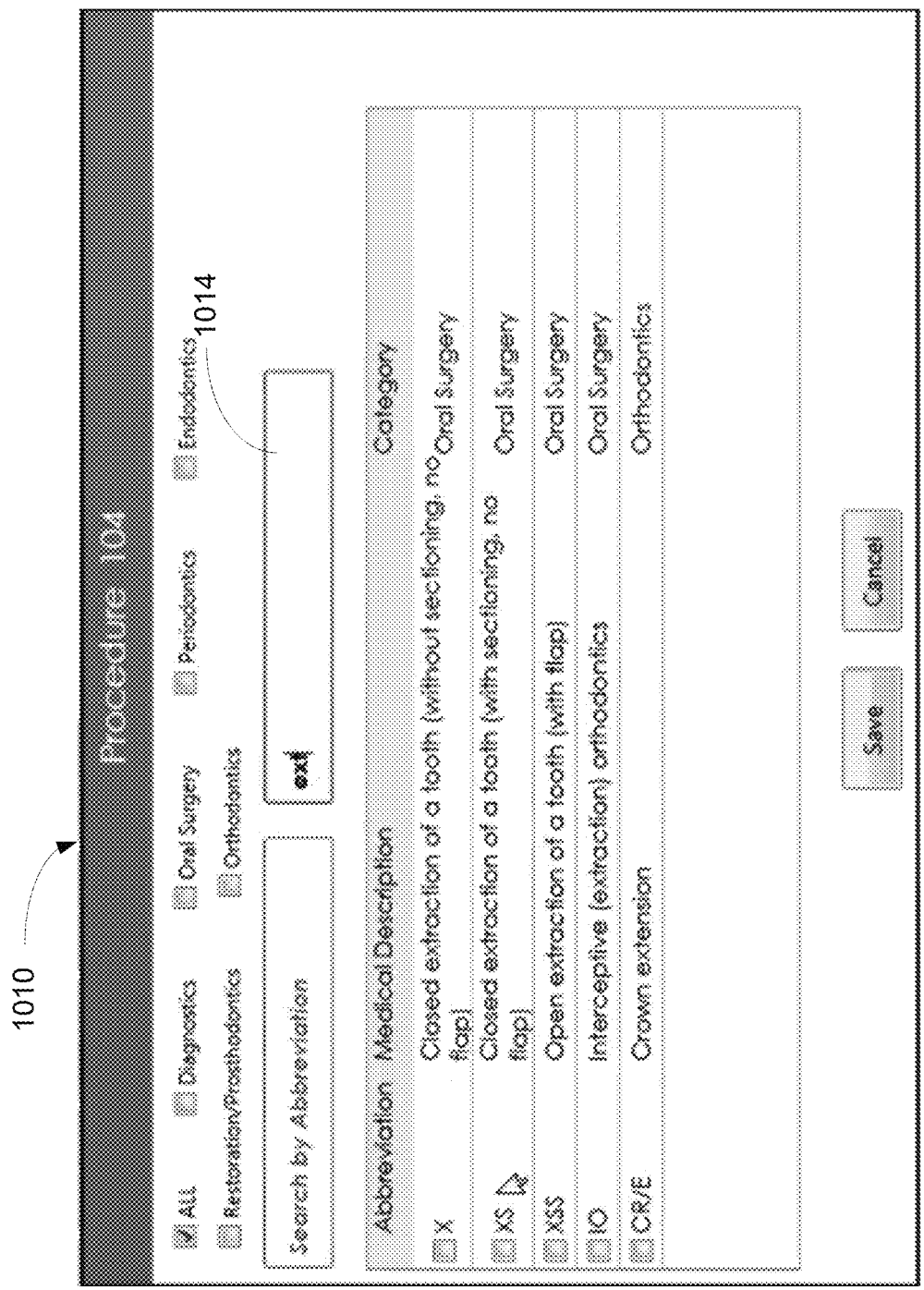
FIG. 10C illustrates another example of the procedure selection dialog box, in accordance with some embodiments.
Figure 10D:
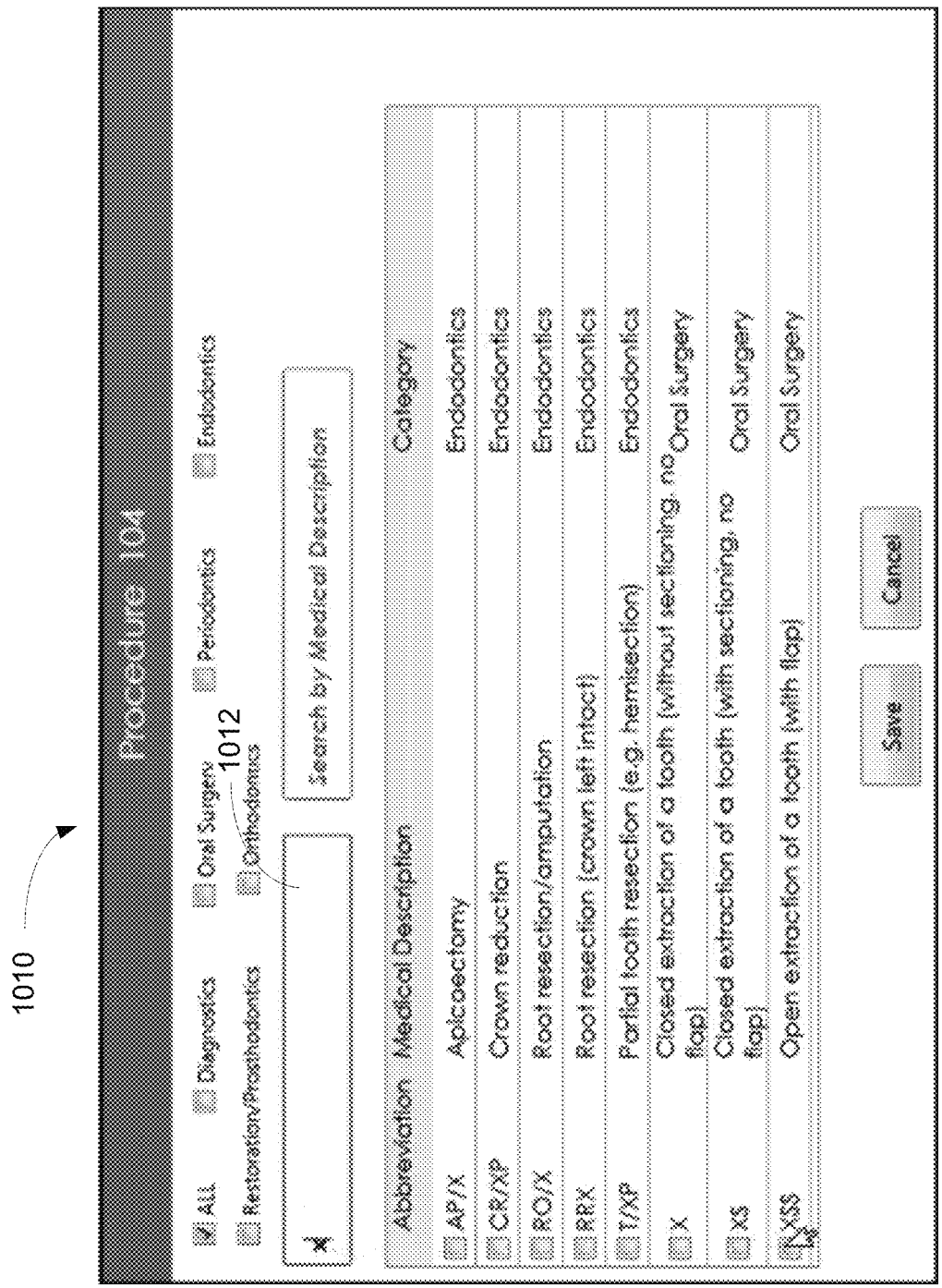
FIG. 10D illustrates another example of the procedure selection dialog box, in accordance with some embodiments.
Figure 10E:
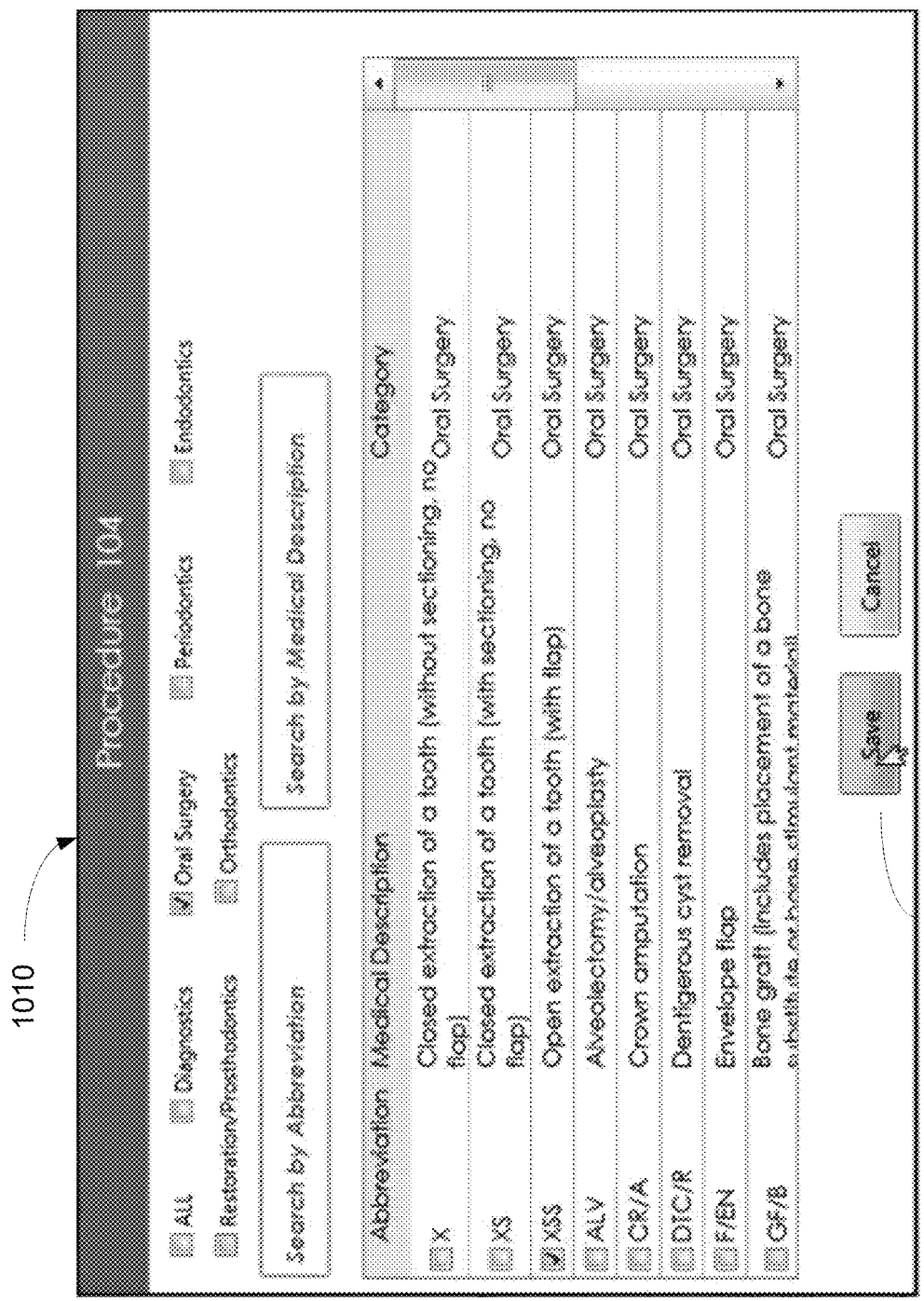
FIG. 10E illustrates another example of the procedure selection dialog box, in accordance with some embodiments.
Figure 10F:
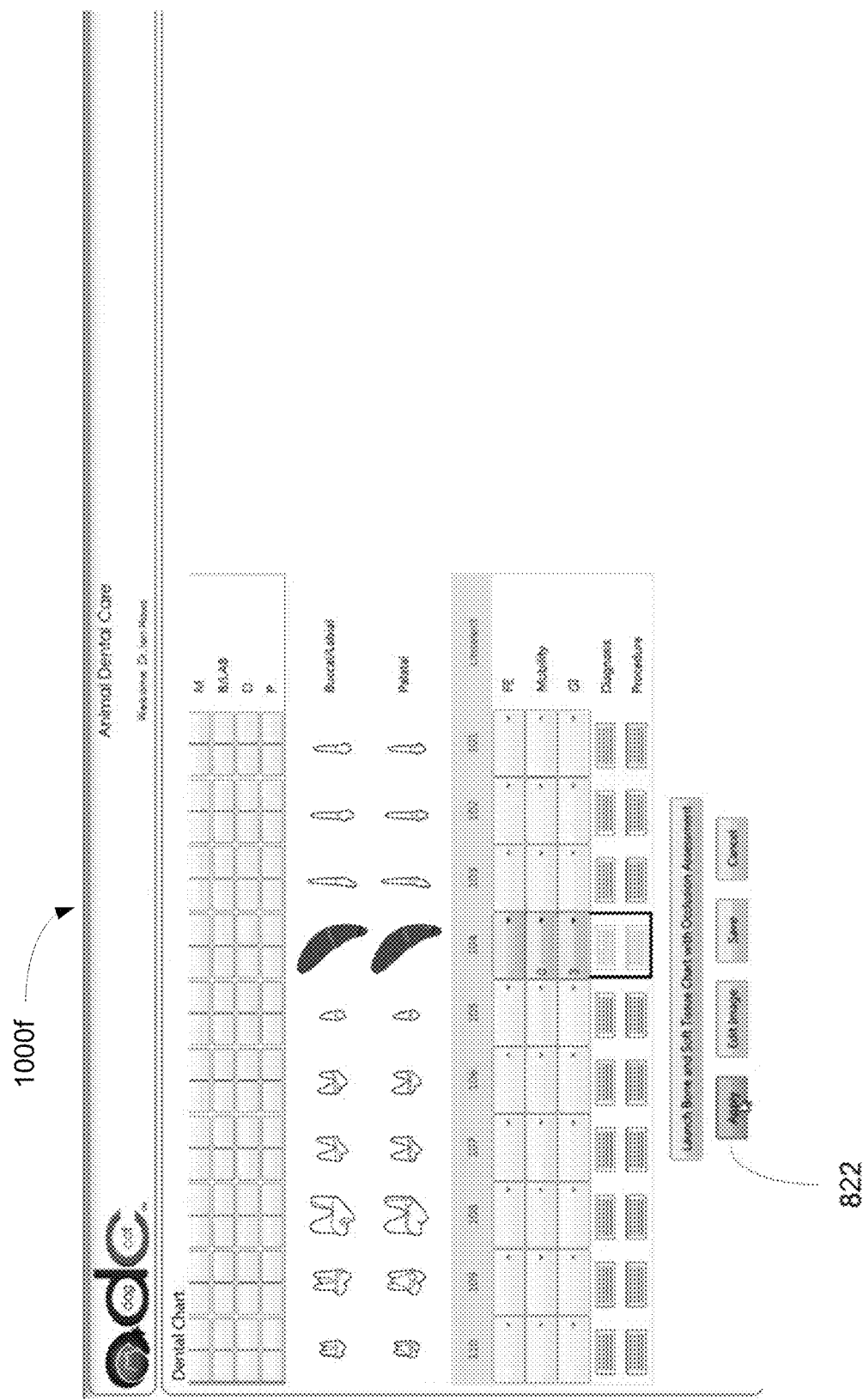
FIG. 10F illustrates, in a screenshot, another example of the quadrant view, in accordance with some embodiments.

FIG. 10C illustrates, in another example of the procedure selection dialog box 1010, the selections that appear when the medical description search input field 1014 receives an input of "ext". FIG. 10D illustrates, in another example of the procedure selection dialog box 1010, the selections that appear when the abbreviation search input field 1012 receives an input of "x". FIG. 10E illustrates, in another example of the procedure selection dialog box 1010, the selections that appear when the types of abbreviations are limited to only "Oral Surgery". In this case, a user has selected the procedure "XSS" which is a universal standard abbreviation for "Open extraction of a tooth (with flap)". In this example, the procedure selection is received when the user selects the "save" button 1020. In this example, once the "Apply" button 822 selection is received, the quadrant view is updated. FIG. 10F illustrates, in a screenshot, another example of the quadrant view 1000f showing the 104 tooth colored or shaded differently (e.g., in red) (that signifies oral surgery; see Table 1 above).

In some embodiments, once the "Apply" button 822 selection is received, an appropriate quadrant definition is retrieved from the repository. The quadrant definition file may include vector based drawing information for each tooth 252 in the quadrant, organized into an extended markup language (XML) based structure, including namespaces, properties and vector based drawing data of each tooth part. Below is a representation of an example of a quadrant definition:

```
<Quadrant>
    <Teeth>
        <Tooth Number>
            <Crowns>
                <Crown>
                    <Color></Color>
                    <Opaque></Opaque>
                    <Vector Line Art Positional Data>
                </Crown>
                <Crown>
                    <Color></Color>
                    <Opaque></Opaque>
                    <Vector Line Art Positional Data>
                </Crown>
            </Crowns>
            <Roots>
                <Root>
                    <Color></Color>
                    <Opaque></Opaque>
                    <Vector Line Art Positional Data>
                </Root>
                <Root>
                    <Color></Color>
                    <Opaque></Opaque>
                    <Vector Line Art Positional Data>
                </Root>
            </Roots>
            <Outline>
                <Color></Color>
                <Opaque></Opaque>
                <Vector Line Art Positional Data>
            </Outline>
        </Tooth Number>
        <Tooth Number>
            ... As above, repeats for each tooth
        </Tooth Number>
    </Teeth>
</Quadrant>
```

The quadrant XML may be updated to a fresh "reset" point, where all properties are reset to represent that no diagnosis or procedure abbreviations have affected the XML structure. Diagnosis abbreviations that have been selected for the quadrant of teeth may be retrieved. Abbreviations may be ordered based upon date/time stamp of user interface (UI) entry (e.g., date ascending order). Each diagnosis abbreviation record may then be applied to the appropriate tooth. None, one, two, or three regions of a tooth may be visually affected by altering XML properties related to a specific tooth, based upon the diagnosis abbreviation's visual impact definitions. All diagnosis abbreviations may be applied in the same manner.

Procedure abbreviations that have been selected for the quadrant of teeth may be retrieved. Abbreviations may be ordered based upon date/time stamp of UI entry (e.g., date ascending order). Each procedure abbreviation may then be applied to the appropriate tooth. None, one, two, or three regions of a tooth may be visually affected by altering XML properties related to a specific tooth, based upon the procedure abbreviation's visual impact definitions. All procedure abbreviations may be applied in the same manner.

The updated XML structure may then be programmatically converted to an SVG graphic which is rendered, which is then programmatically converted to a BITMAP or JPG image, depending upon charting type. At this point, there is a vector-based lossless graphic that is rendered to a BITMAP or JPG specific to diagnosis and procedure abbreviations for teeth in the quadrant. In some embodiments, vector based images produce non-pixelated fills resulting in higher quality images. When vector based renderings are reduced or increased in size, image quality is not impacted (as compared to raster-based images that suffer degradation when enlarged or shrunk).

If a manually edited quadrant image exists, both images may be programmatically loaded into memory. Using a GDI kernel API, a bitblt process may be used with a specific raster constant to overlay (transparently) the edited image on to the dynamically generated image. In some embodiments, the combined image may be rendered as a 100% quality JPG or BITMAP image. The ADC application may now display either a visually updated preview of the quadrant, or a merged update (if a manually edited image exists). By merging a manually edited diagrams transparently with the programmatically rendered quadrants (e.g., by overlaying the manual edits over the quadrant view renderings), the dental charting system 100, 700, 780 may change underlying (programmatically rendered quadrants) without affecting the manually edited content. This allows for the manually edited graphic to be retained (and does not need to be re-created or re-edited) when the programmatically rendered quadrants are updated with subsequent diagnosis and/or procedures.

The SAVE process is similar, but all four quadrants are processed. Diagnosis and procedure abbreviations and other non-image data related to the dental chart may be synchronized to the server where the repository is located. Finally, a similar technique may be used to process an occlusal view using an opaqueness factor that allows teeth shading contours to be visible. Images generated by the ADC client application may then be synchronized to the server, enabling other users in the same practice to immediately view current records via the ADC application or web portal (i.e., secure access can be given to a client or referring veterinarian).

In some embodiments, where multiple diagnoses or procedures have been assigned to the same tooth (i.e., multiple diagnosis and/or procedure inputs have been received), each tooth may be processed first using the assigned diagnosis abbreviations in the order they were selected, and then processed using assigned procedure abbreviations assigned in the order they were selected. It is noted that diagnosis and procedure abbreviation definitions do not always affect all regions of a tooth. It is noted that diagnosis records may be processed first—ordered by timestamp—oldest (firstly entered) to newest (lastly entered). This affects visual aspects of the result by ensuring that the newest or last diagnosis entry for a specific tooth supersedes, if necessary, a previous diagnosis for that tooth. Procedure records may then be processed—ordered by timestamp—oldest (firstly entered) to newest (lastly entered). Once again, this affects visual aspects of the result by ensuring that the newest or last procedure entry for a specific tooth supersedes, if necessary, a previous procedure or diagnosis for that tooth.

Figure 11A:
FIG. 11A illustrates, in a chart diagram, an example of an animal dental chart, in accordance with some embodiments.
Figure 11B:
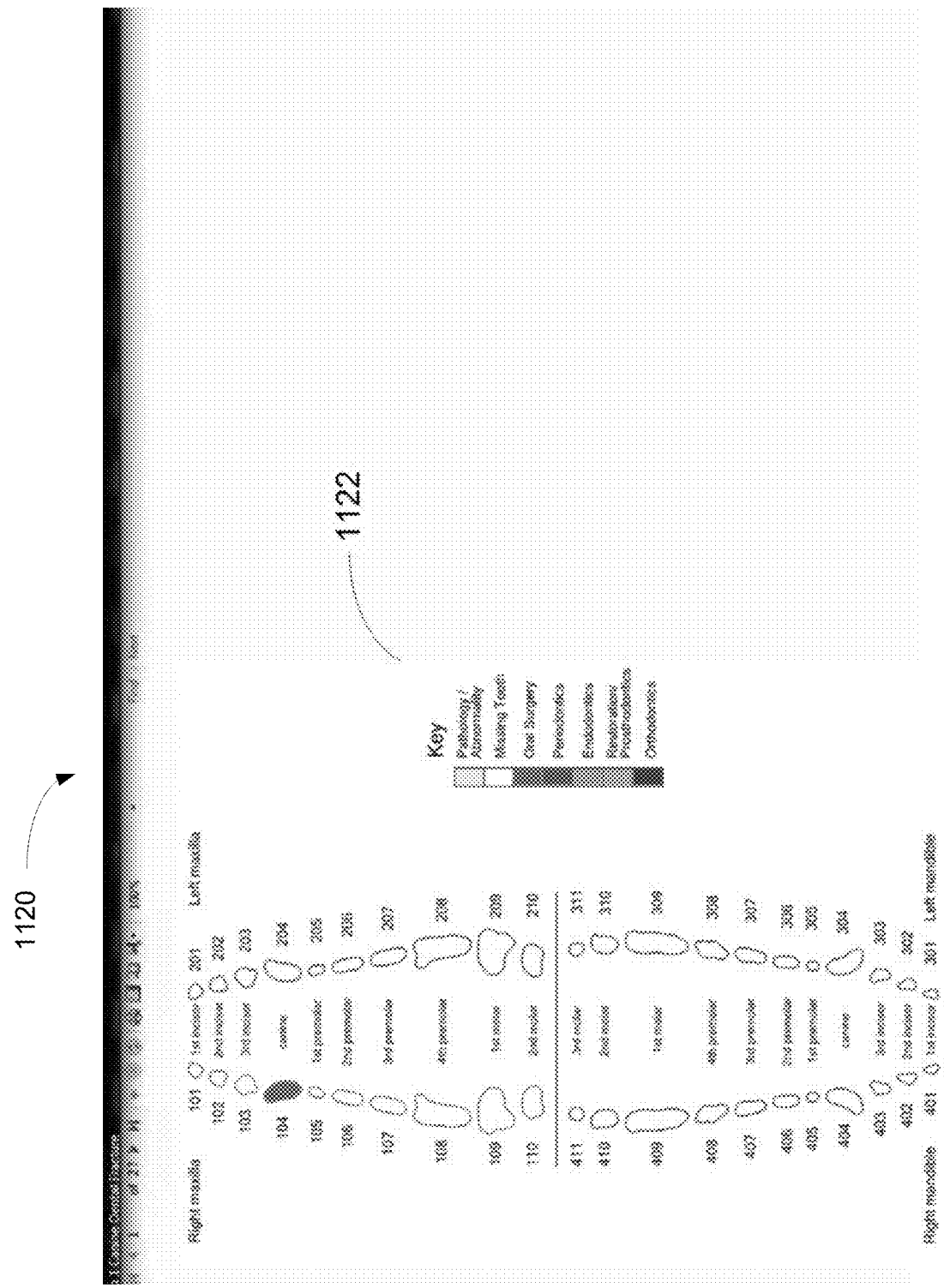
FIG. 11B illustrates, in a chart diagram, an example of an occlusal dental chart, in accordance with some embodiments.
Figure 11C:
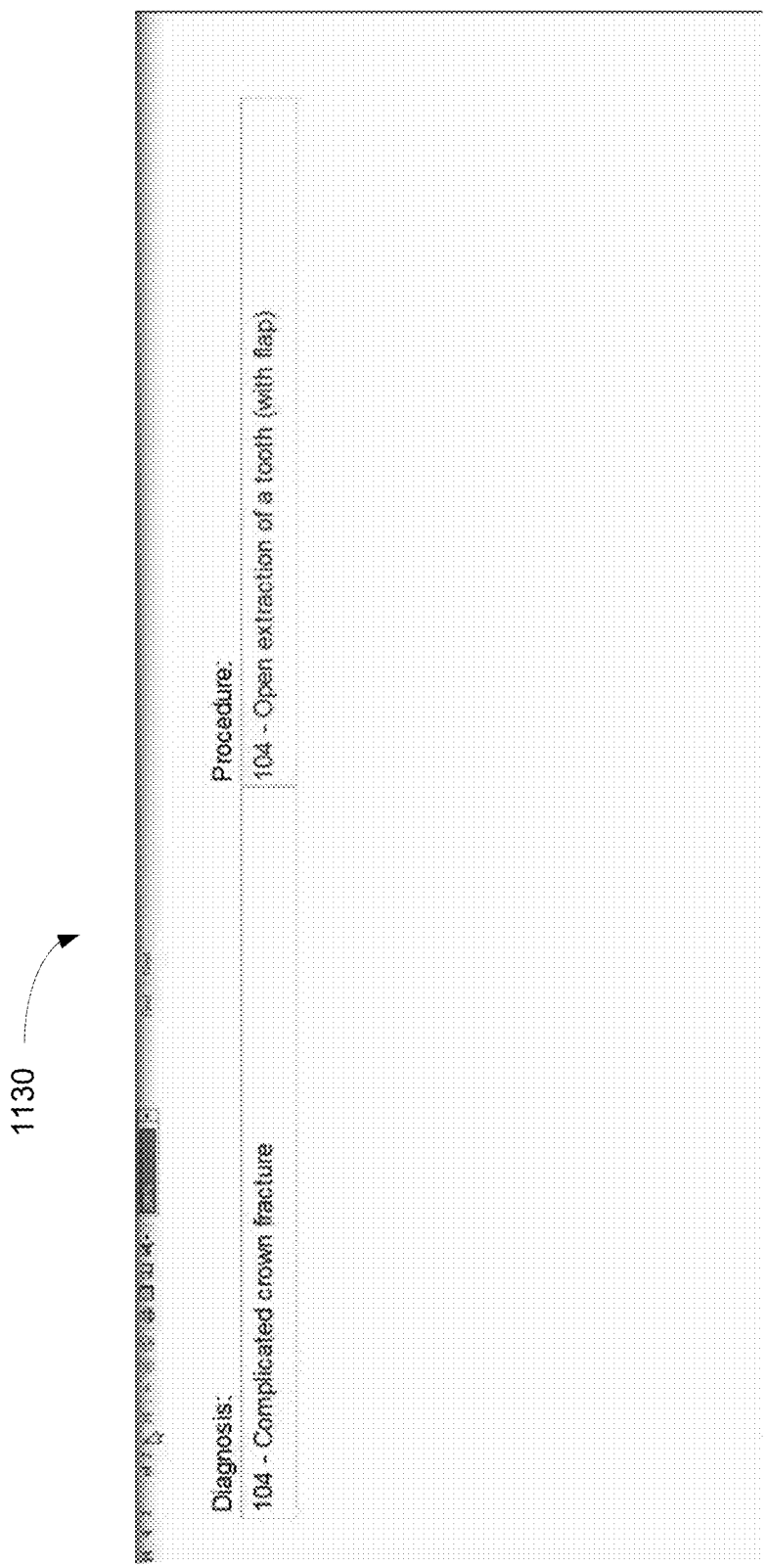
FIG. 11C illustrates, in a screenshot, an example of a technical description of a diagnosis and a procedure, in accordance with some embodiments.
Figure 11D:
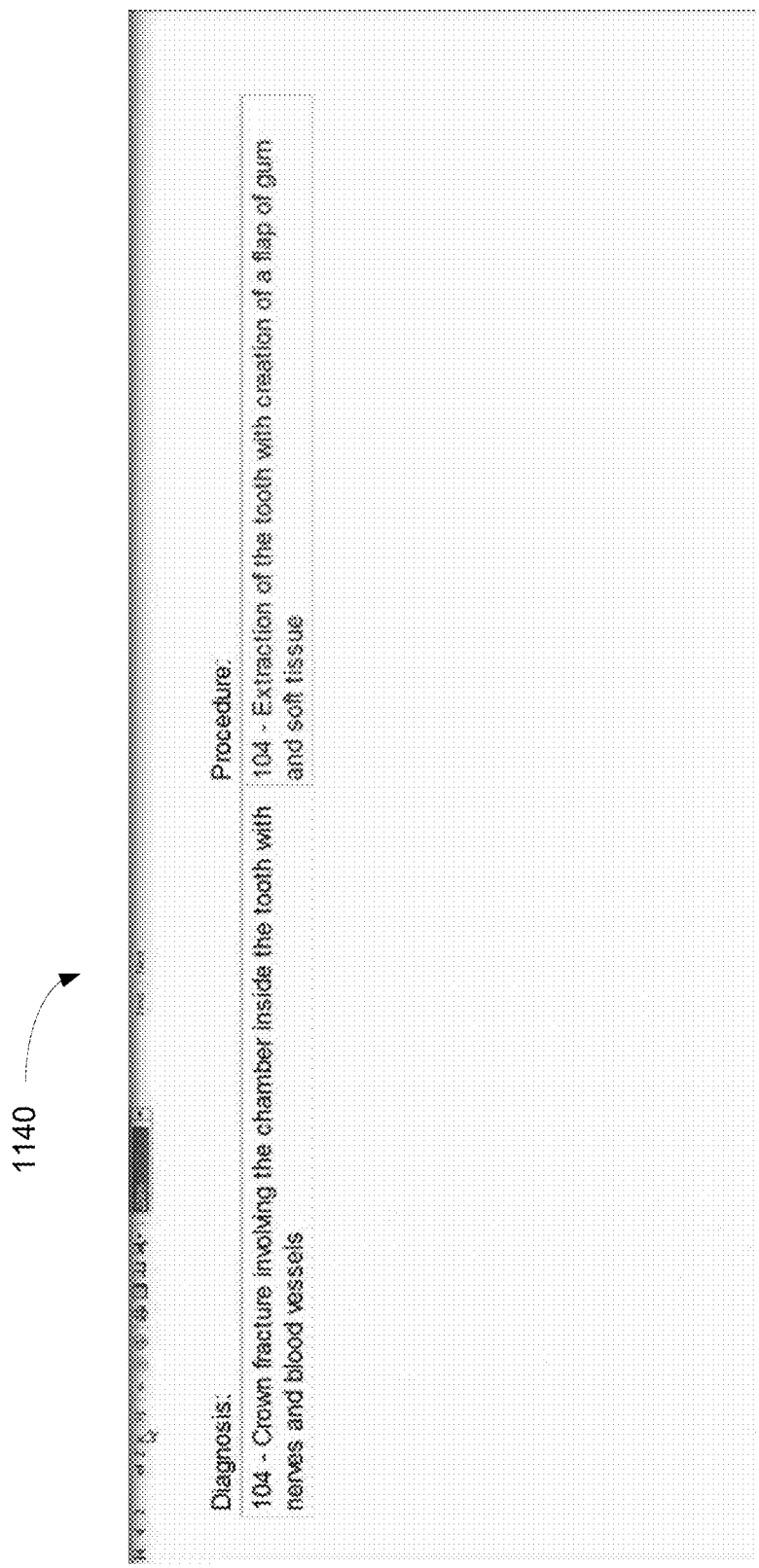
FIG. 11D illustrates, in a screenshot, an example of a lay person description of the diagnosis and the procedure, in accordance with some embodiments.

FIG. 11A illustrates, in a chart diagram, an example of an animal dental chart 1100, in accordance with some embodiments. The dental chart 1100 shows the changes to tooth 104 for the canine. Also shown in the dental chart 1100 are the input values for Mobility, GI, diagnosis and procedure that were received. FIG. 11B illustrates, in a chart diagram, an example of an occlusal dental chart 1120, in accordance with some embodiments. The occlusal dental chart may include a key 1122 identifying the meaning of color or shading on the teeth in the chart 1120. A second page (or subsequent pages) may be added to the occlusal dental chart 1120 that includes (or include) the text for the diagnosis and procedure that have been applied to the teeth in the chart 1120. FIG. 11C illustrates, in a screenshot, an example of a technical description 1130 of the diagnosis and procedure that can be added as a second page or screen for an official report, in accordance with some embodiments. In this example, the diagnosis was "104—Complicated crown fracture." In this example, the procedure was "104—Open extraction of a tooth (with flap)." FIG. 11D illustrates, in a screenshot, an example of a lay person description 1140 of the diagnosis and procedure that can be added as a second page or screen for a lay person or client report, in accordance with some embodiments. In this example, the diagnosis was "104—Crown fracture involving the chamber inside the tooth with nerves and blood vessels." In this example, the procedure was "104—Extraction of the tooth with creation of a flap of gum and soft tissue."

As noted above, more than one tooth may receive the same diagnosis or procedure input at the same time. This would save veterinarian time providing cost efficiency for the owner, and better health for the animal that may otherwise need to be anesthetized for a longer period of time. Combining teeth into a quadrant collection allows for this to take place.

Figure 12A:
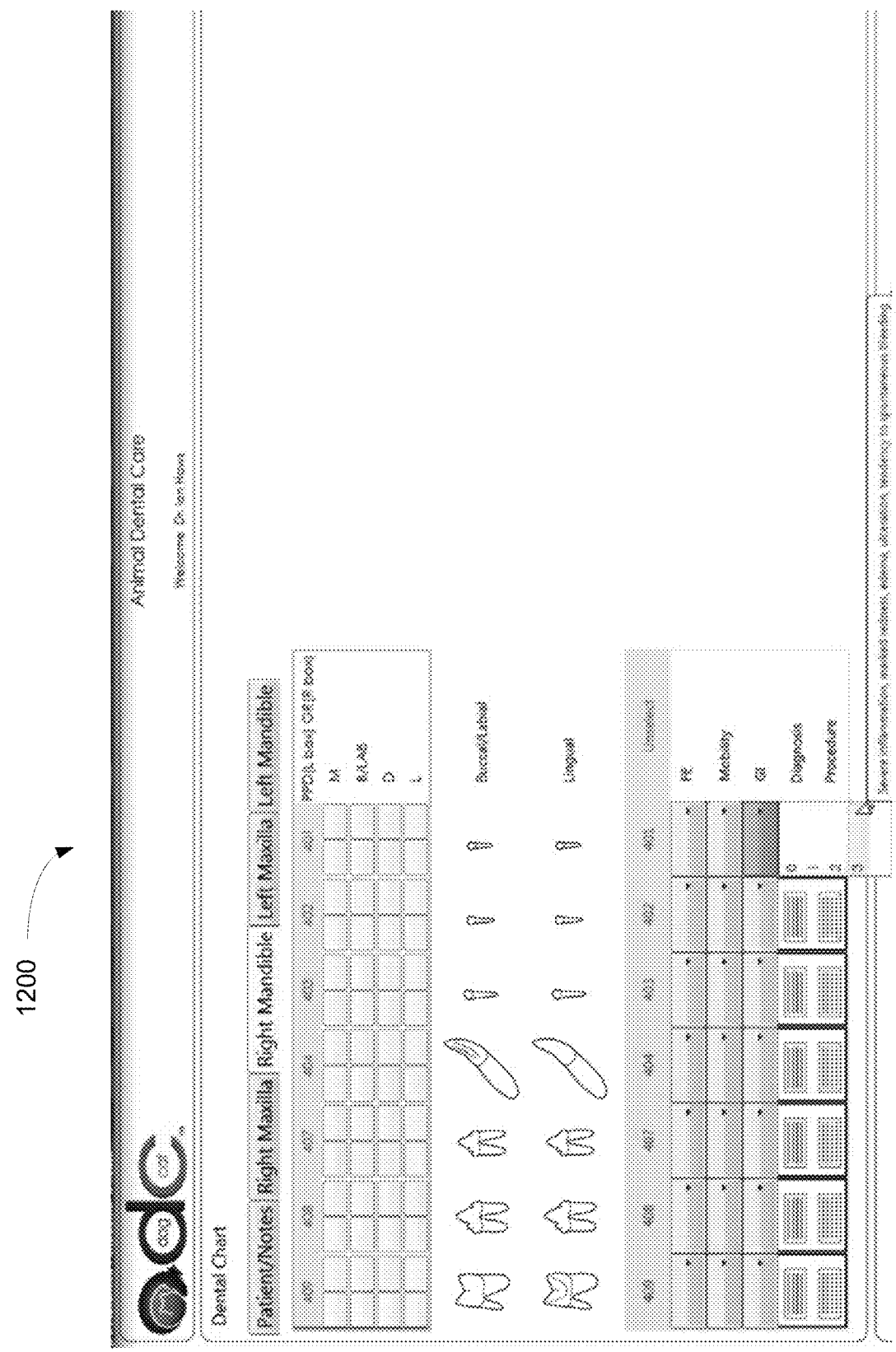
Figure 12B:
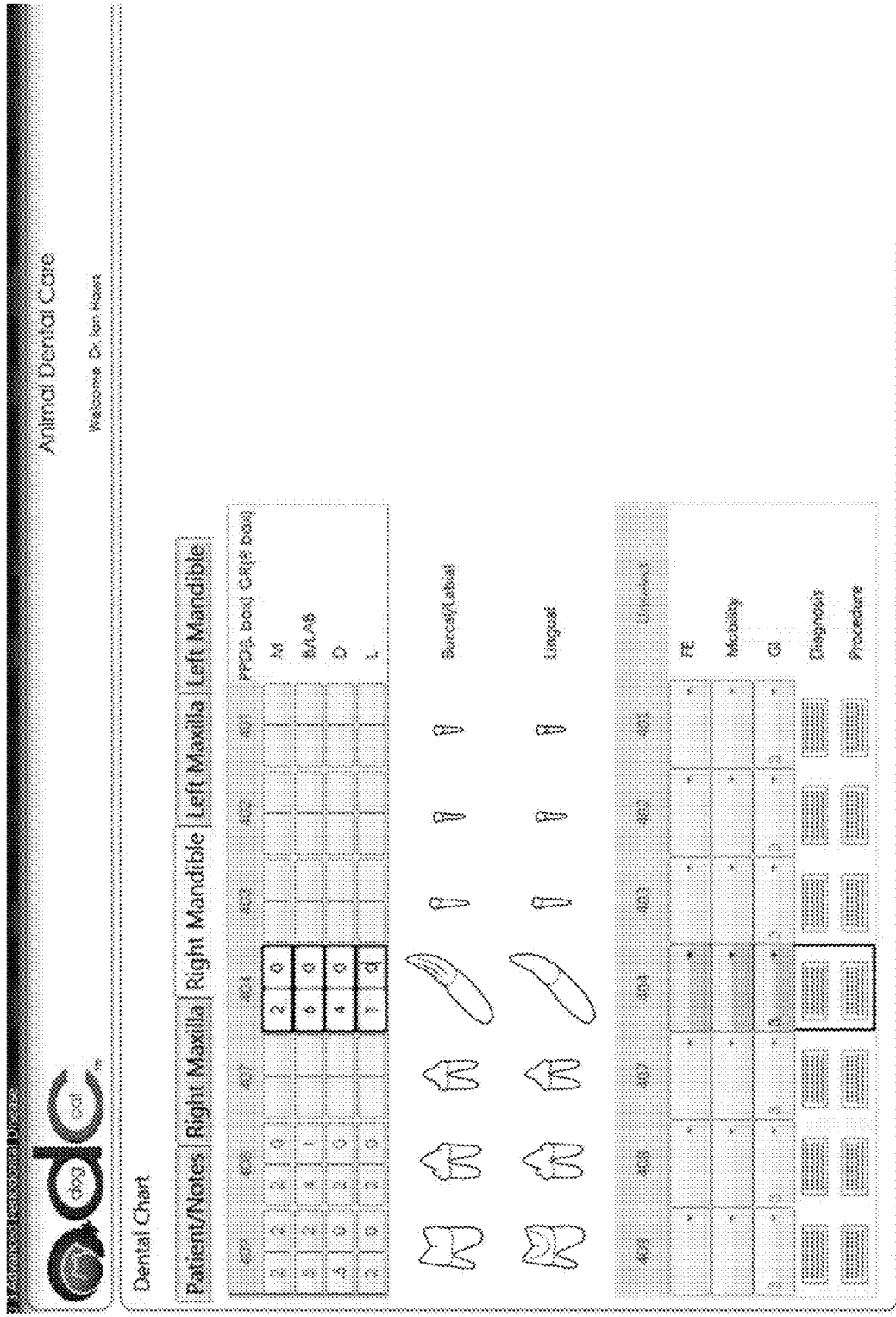
Figure 12C:
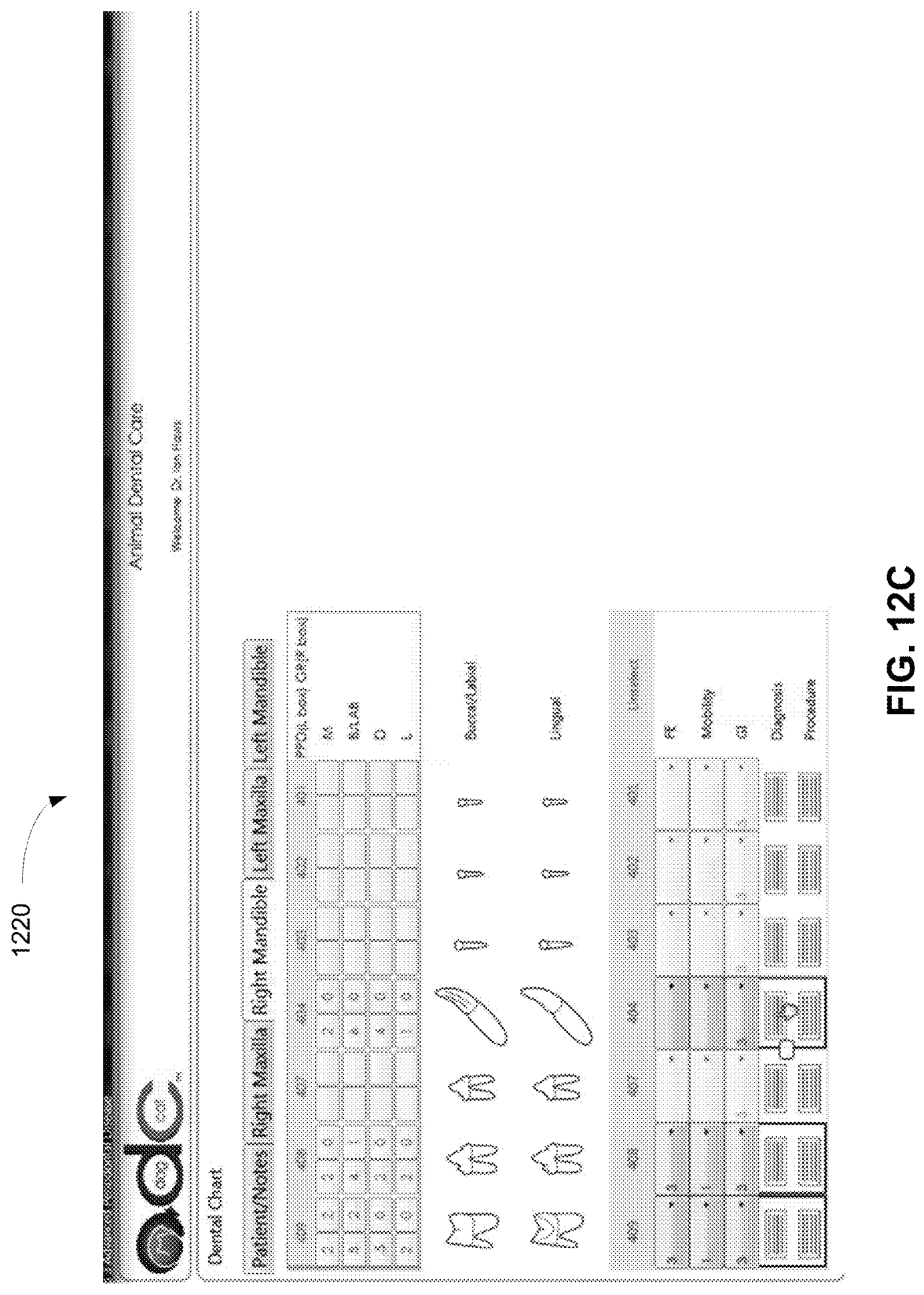
Figure 12D:
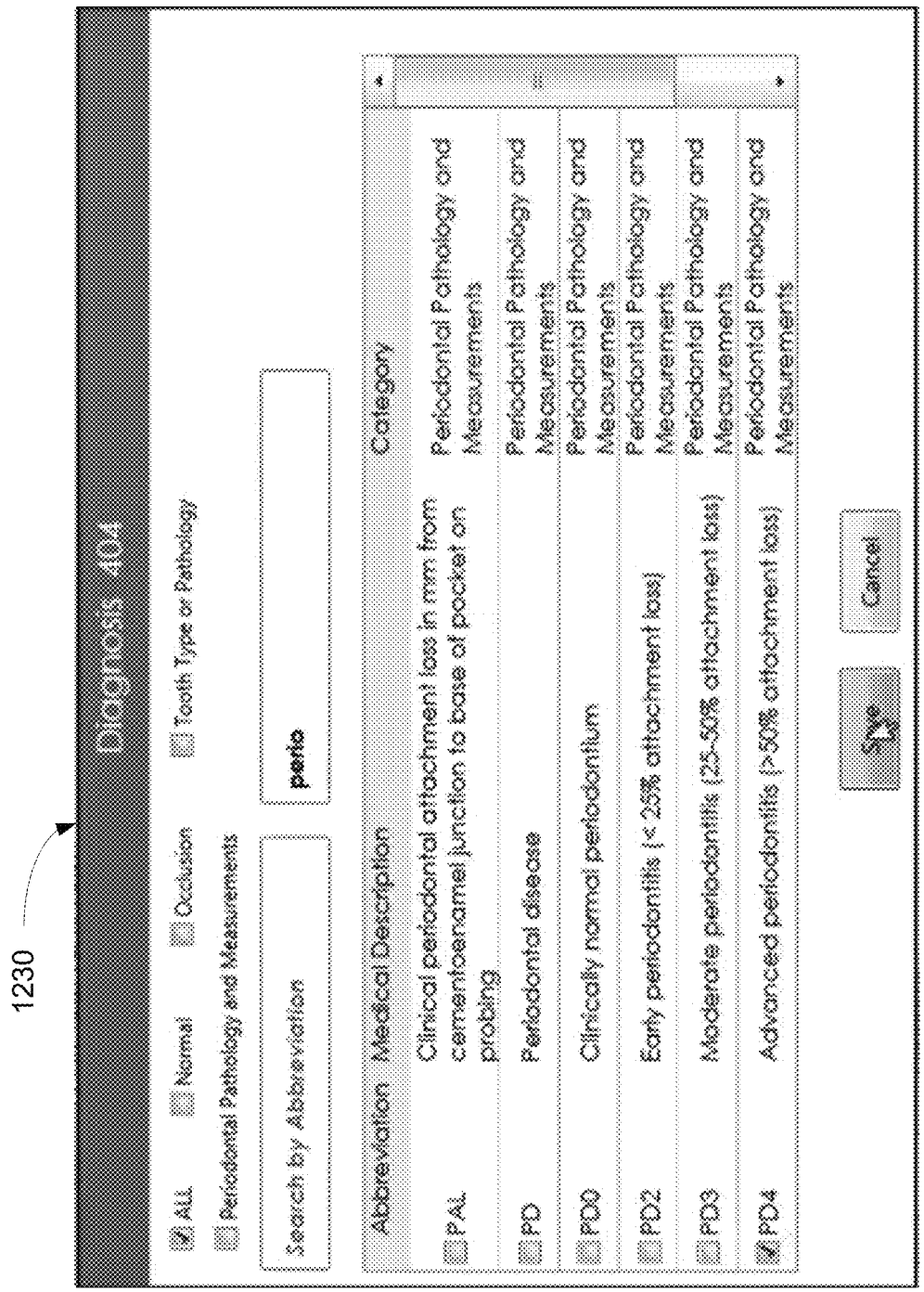
Figure 12E:
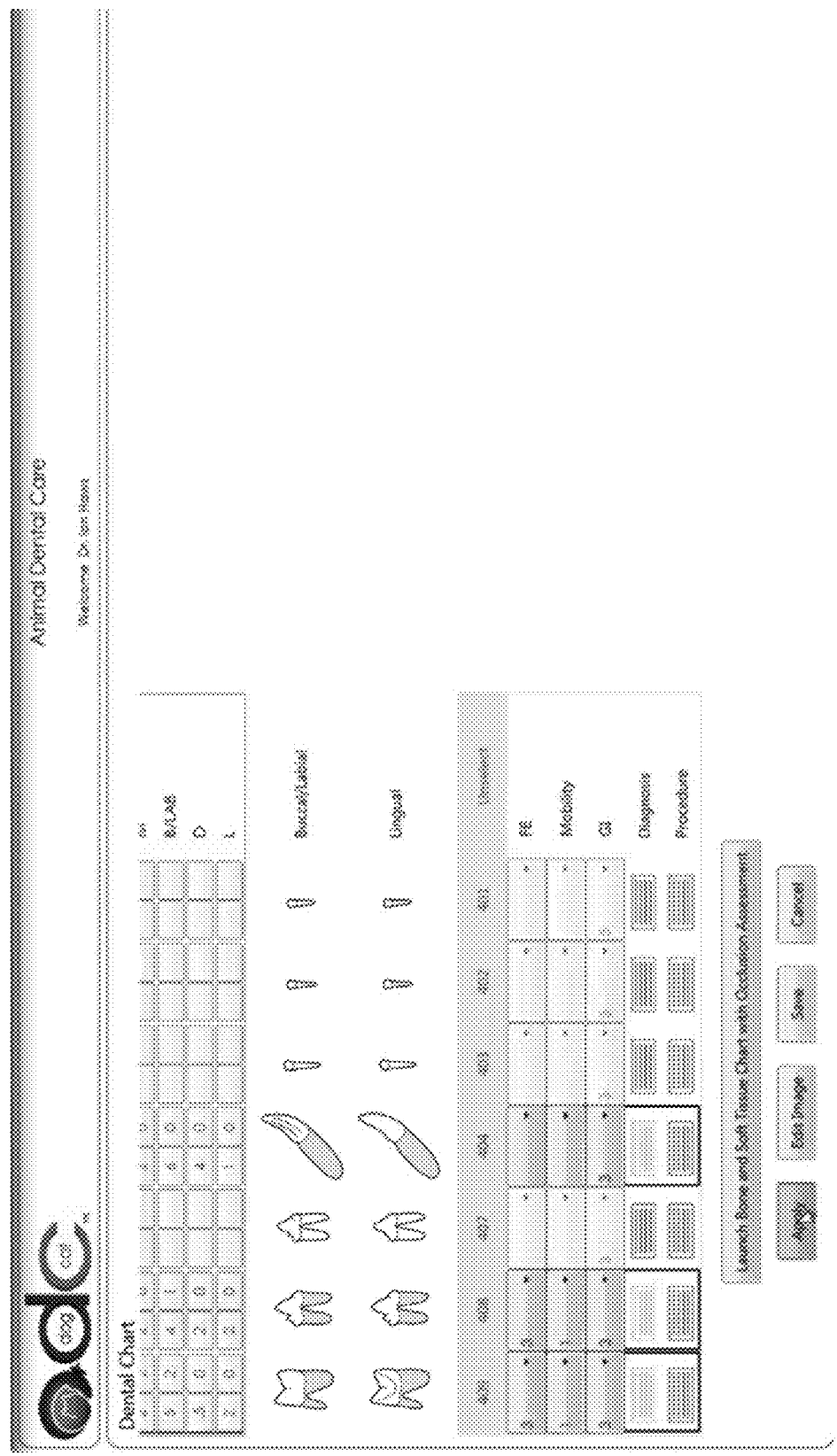
Figure 12F:
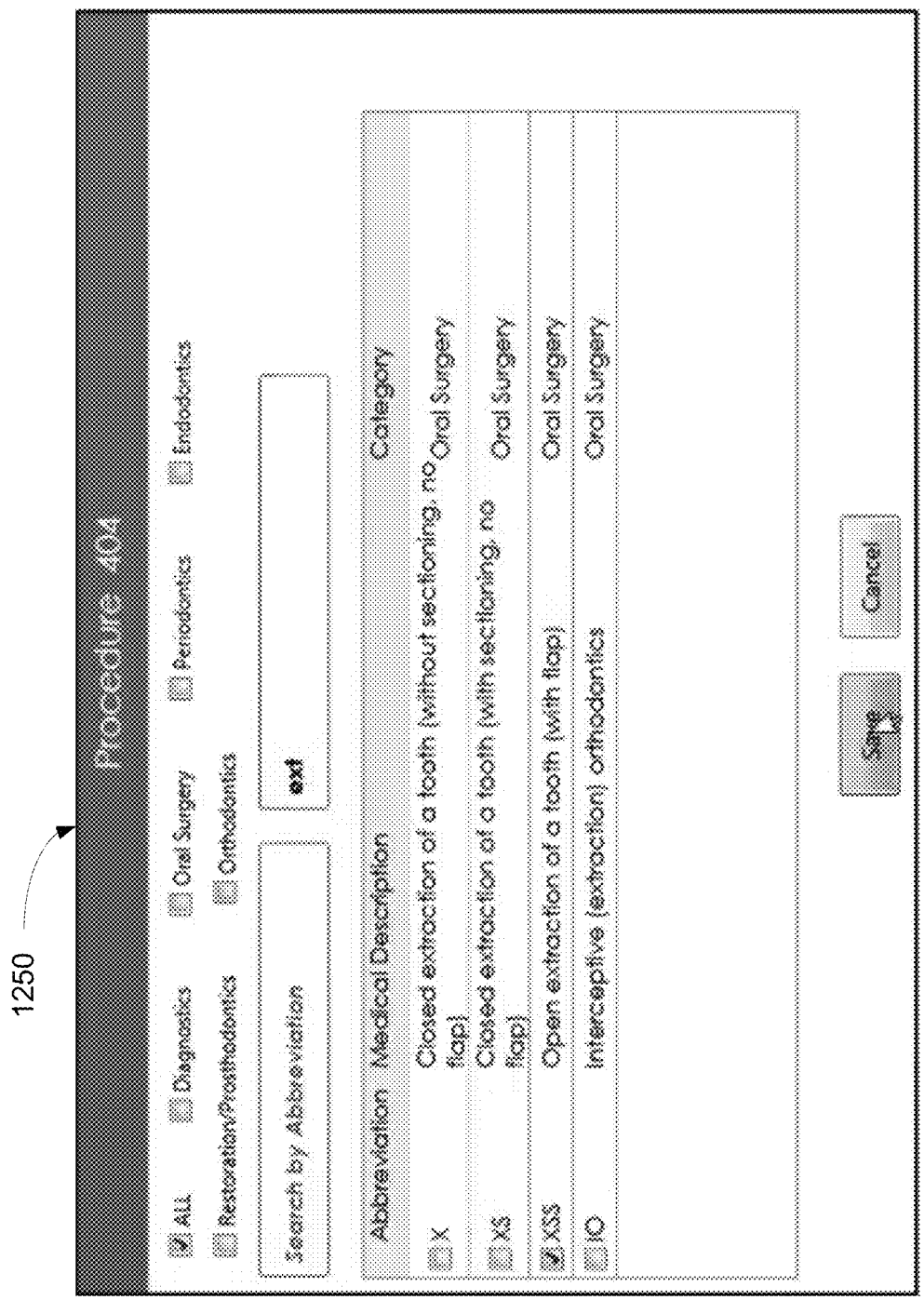
Figure 12G:
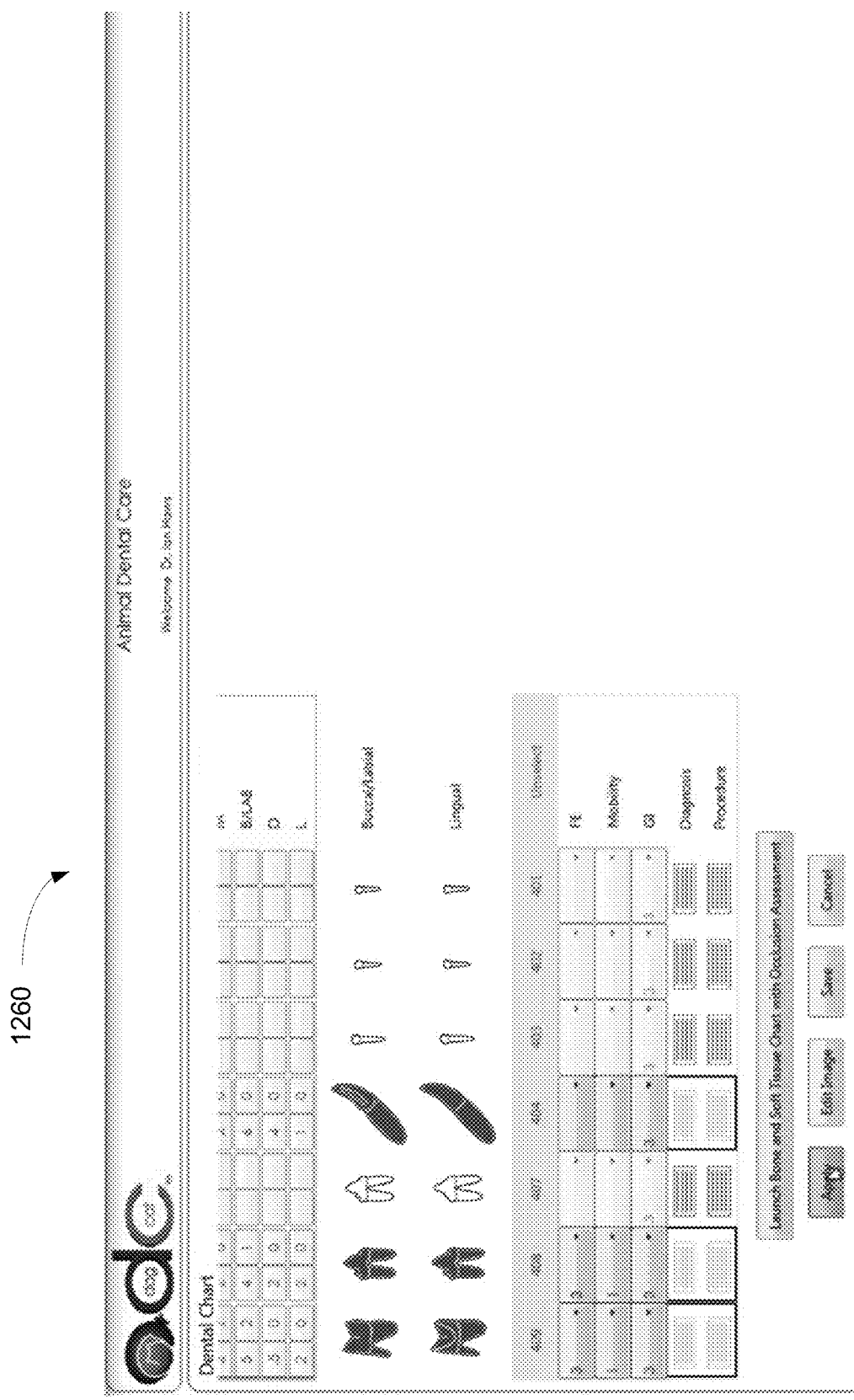
Figure 13:
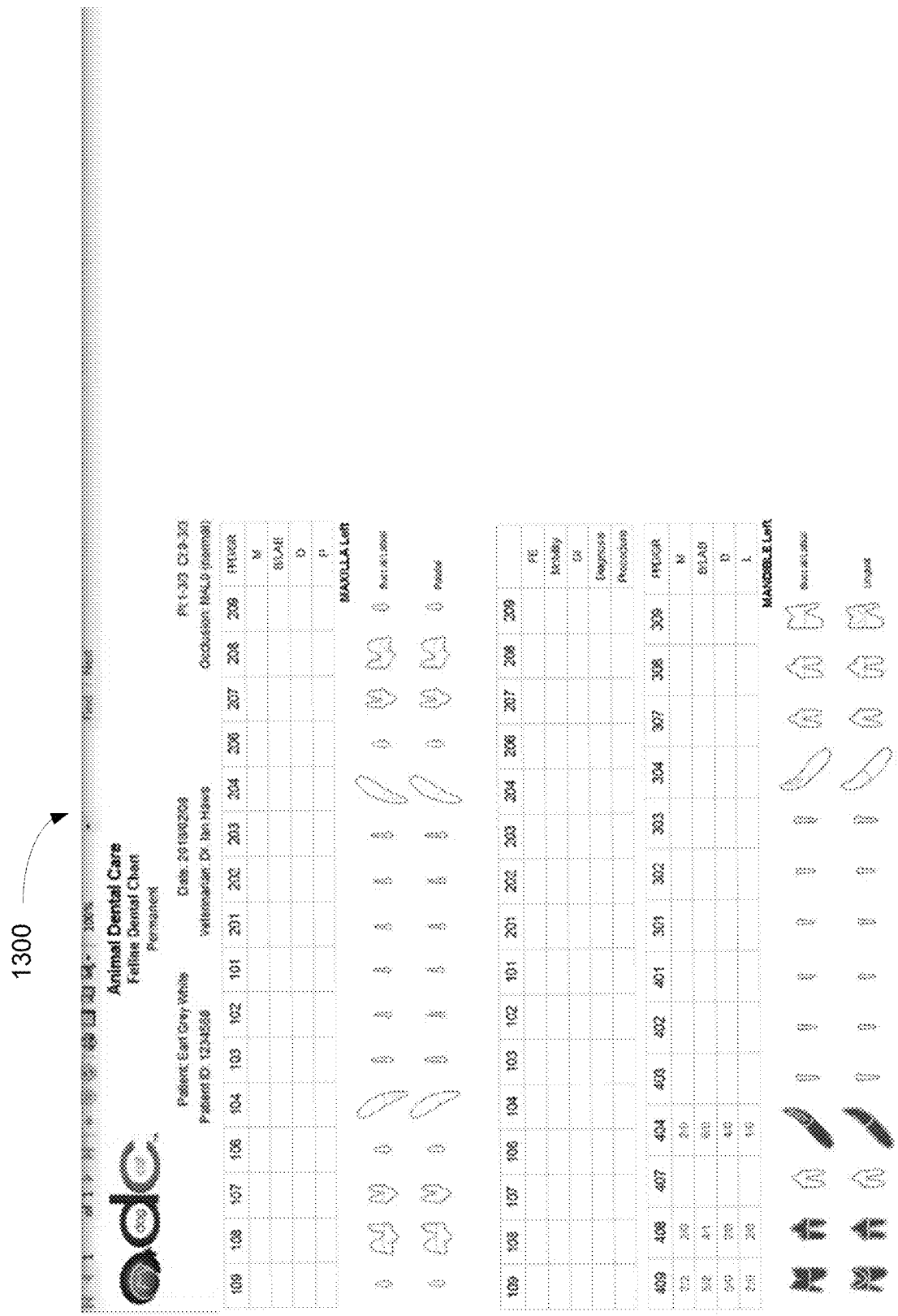
FIG. 13 illustrates, in a screenshot, the dental chart that is generated for the example of FIGS. 12A to 12G.

FIGS. 12A to 12G illustrate, in a sequence of screenshots, another example of operation of the dental charting system 100, 700, in accordance with some embodiments. This example involves a set of permanent canine teeth. FIG. 12A illustrates, in a screenshot, an example of a right mandible quadrant view 1200 of a set of permanent canine teeth. Each of teeth 409, 408, 407, 404, 403, 402 and 401 are selected and receive a GI input value of "3" at the same time. FIG. 12B illustrates, in a screenshot, another example of a right mandible quadrant view 1210. In this screenshot 1210, input for periodontal measurements are received separately for each tooth 409, 408 and 404. FIG. 12C illustrates, in a screenshot, another example of a right mandible quadrant view 1220. In this screenshot 1220, input for FE and Mobility was received for teeth 409 and 408 at the same time. Tooth 404 has been added to the selection and a diagnosis input will be entered for the three teeth at the same time. FIG. 12D illustrates, in a screenshot, another example of a diagnosis selection dialog box 1230. In this screenshot 1230, the diagnosis abbreviation "PD4" is selected as the diagnosis input value for the three teeth. FIG. 12E illustrates, in a screenshot 1240, the updated quadrant view showing the roots for teeth 409, 408 and 404 colored (e.g., in yellow) or shaded (corresponding to diagnosis input "PD4"). FIG. 12F illustrates, in a screenshot, another example of a procedure selection dialog box 1250. In this screenshot 1250, the procedure abbreviation "XSS" (associated with oral surgery) is selected as the procedure input value for the three teeth. FIG. 12G illustrates, in a screenshot 1260, the updated quadrant view showing teeth 409, 408 and 404 colored (e.g., in red) or shaded (corresponding to procedure input "XSS"). FIG. 13 illustrates, in a screenshot, the dental chart 1300 that is automatically generated for the example of FIGS. 12A to 12G.

Figure 14A:
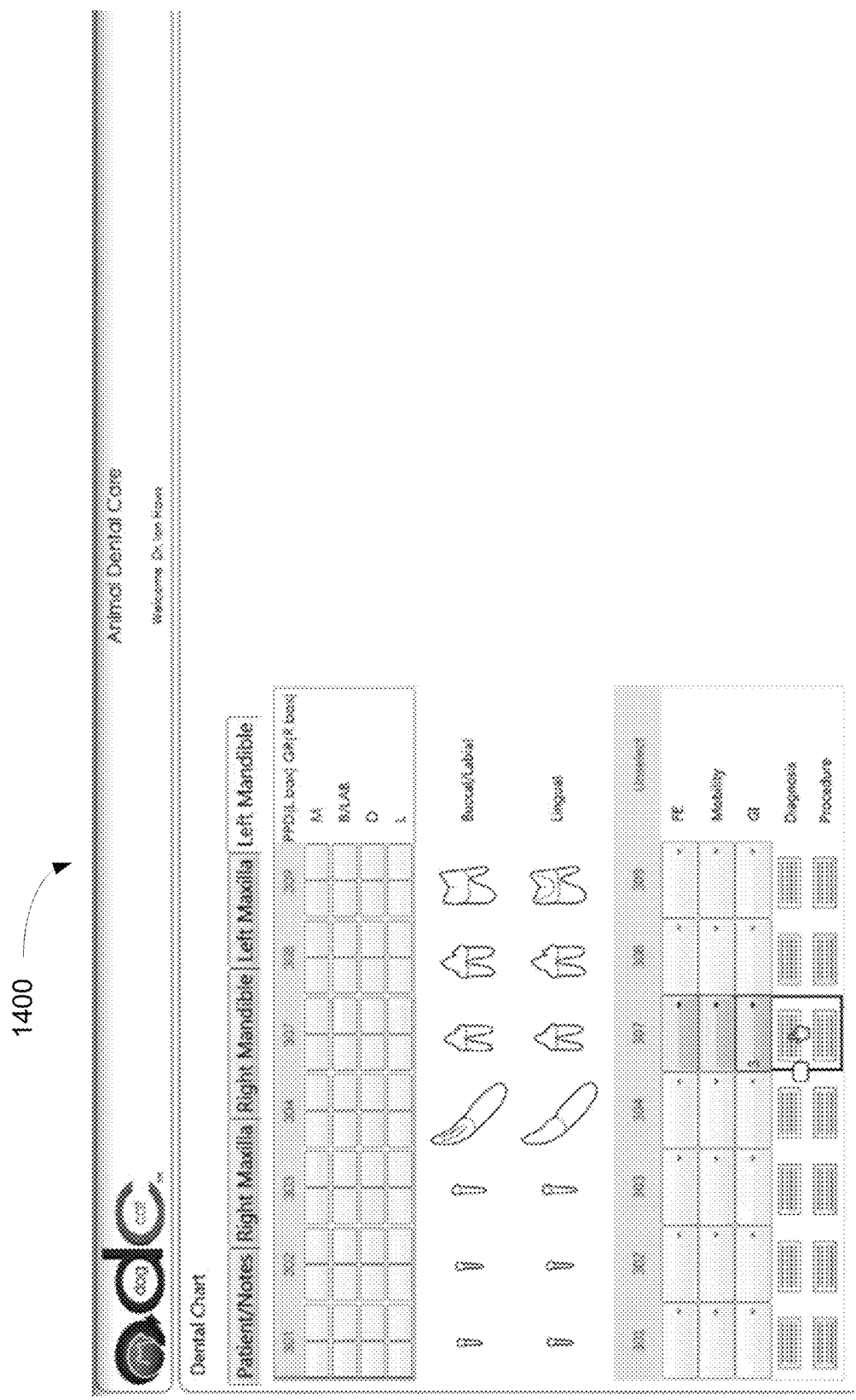
FIGS. 14A to 14G illustrate, in a sequence of screenshots, another example of operation of the dental charting system, in accordance with some embodiments.
Figure 14B:
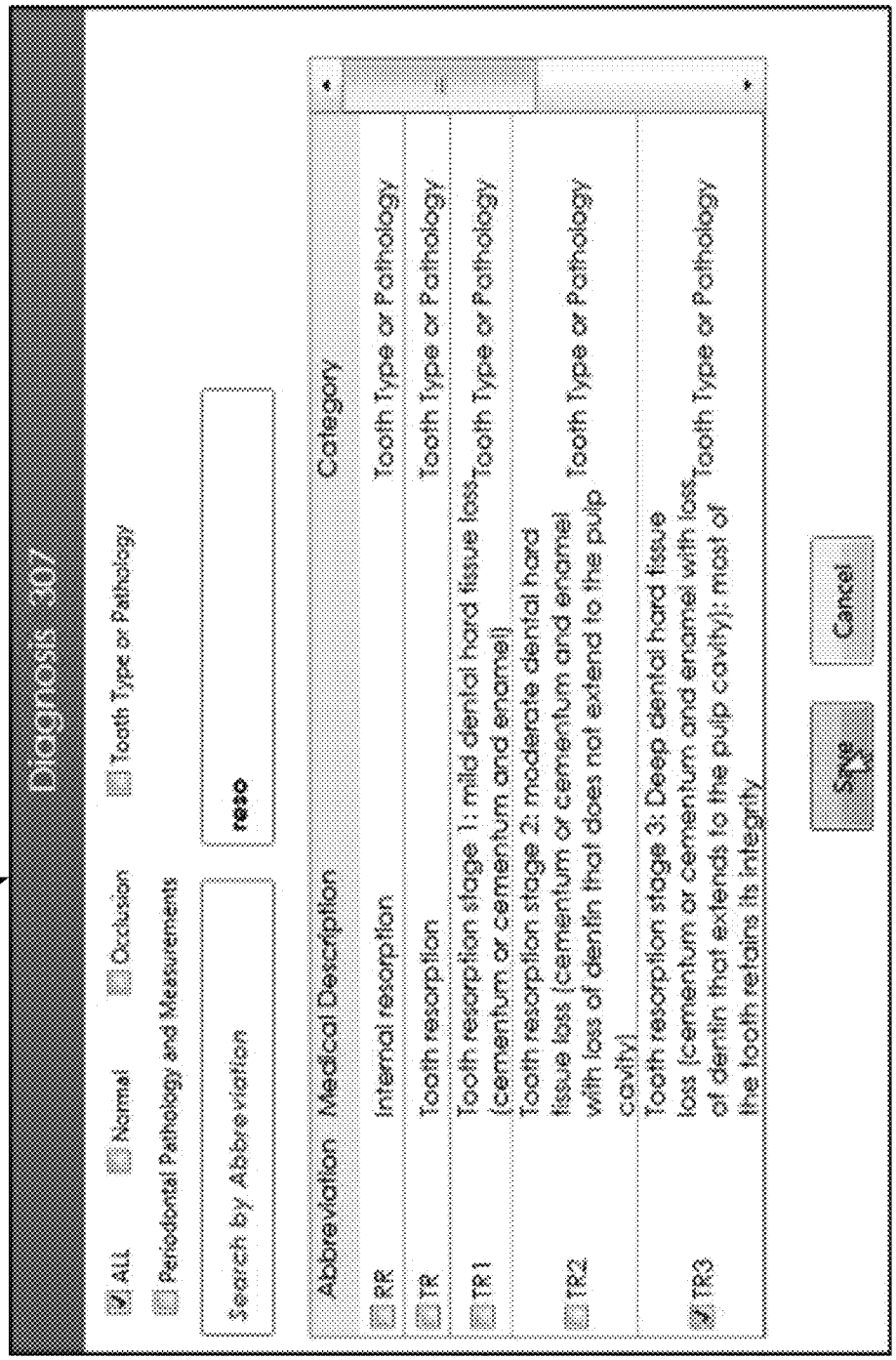
Figure 14C:
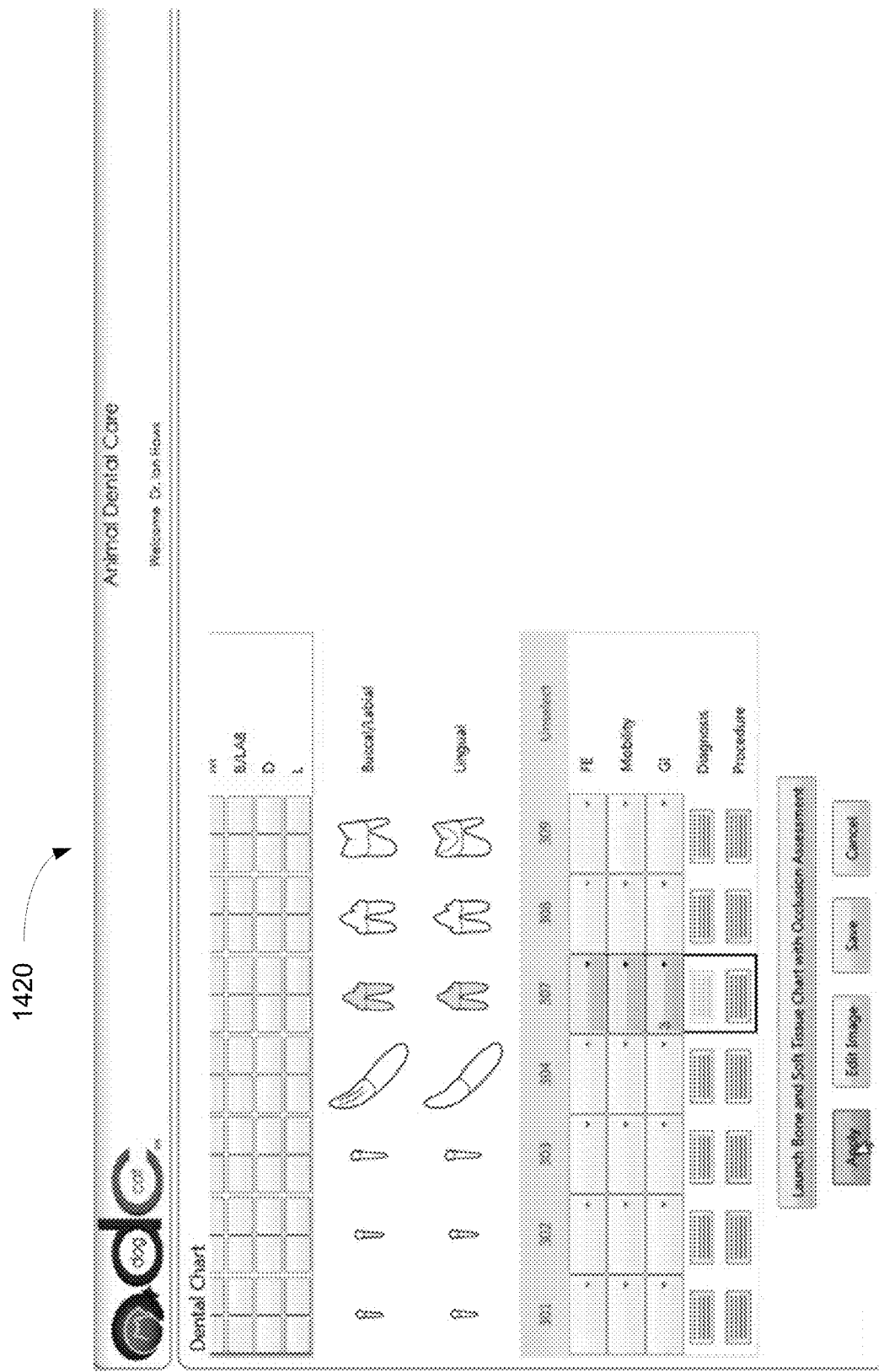
Figure 14D:
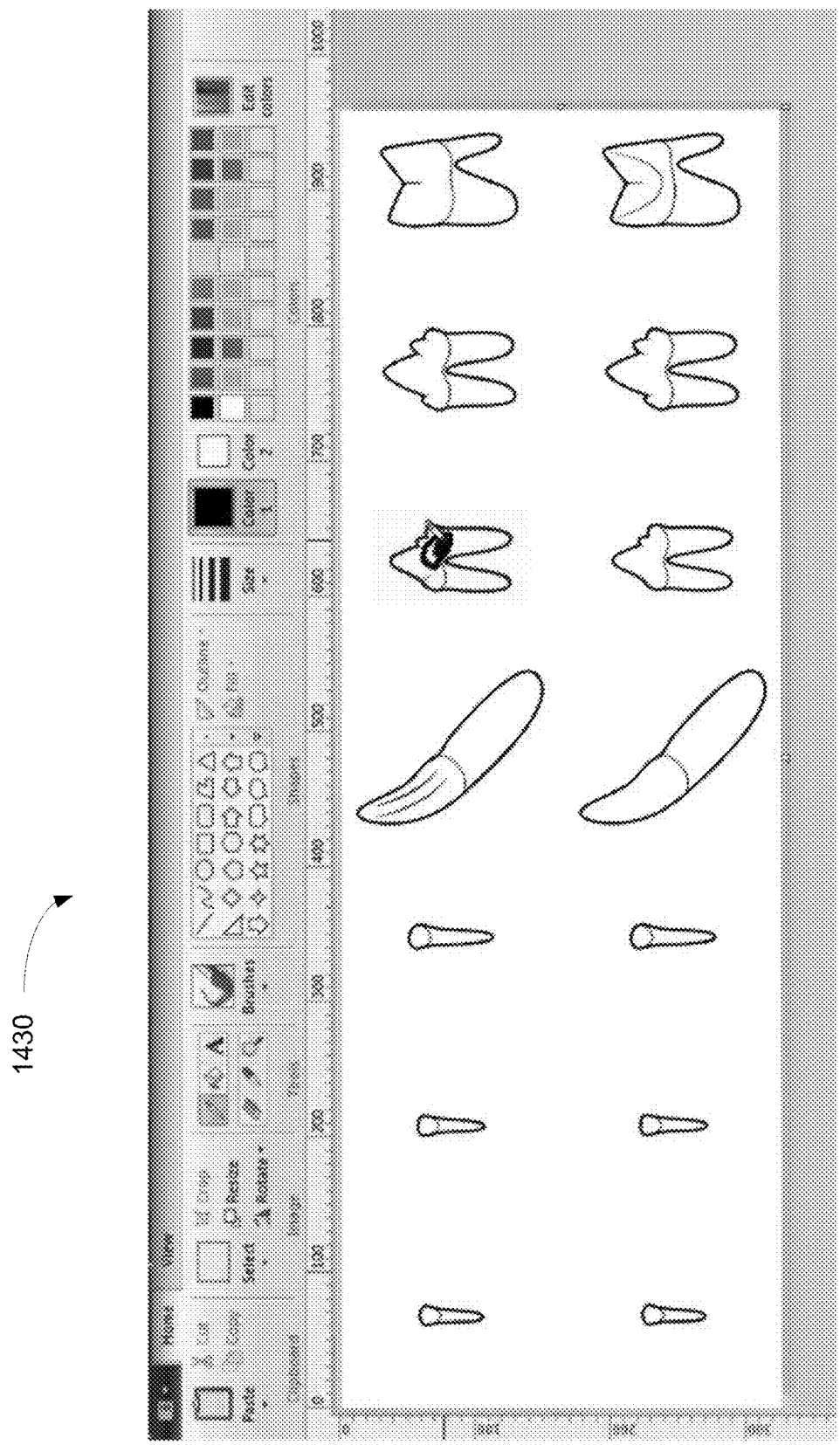
Figure 14E:
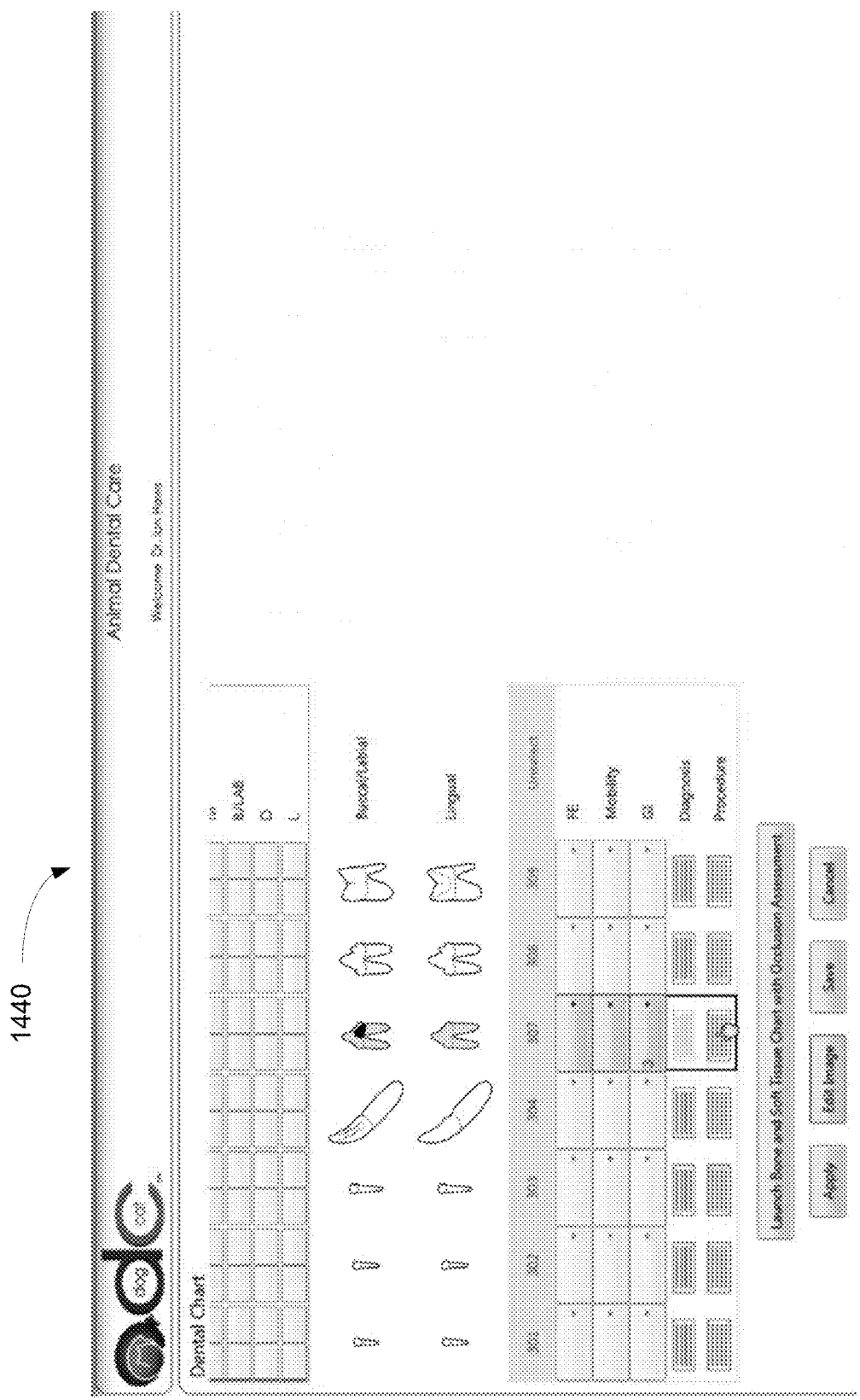
Figure 14F:
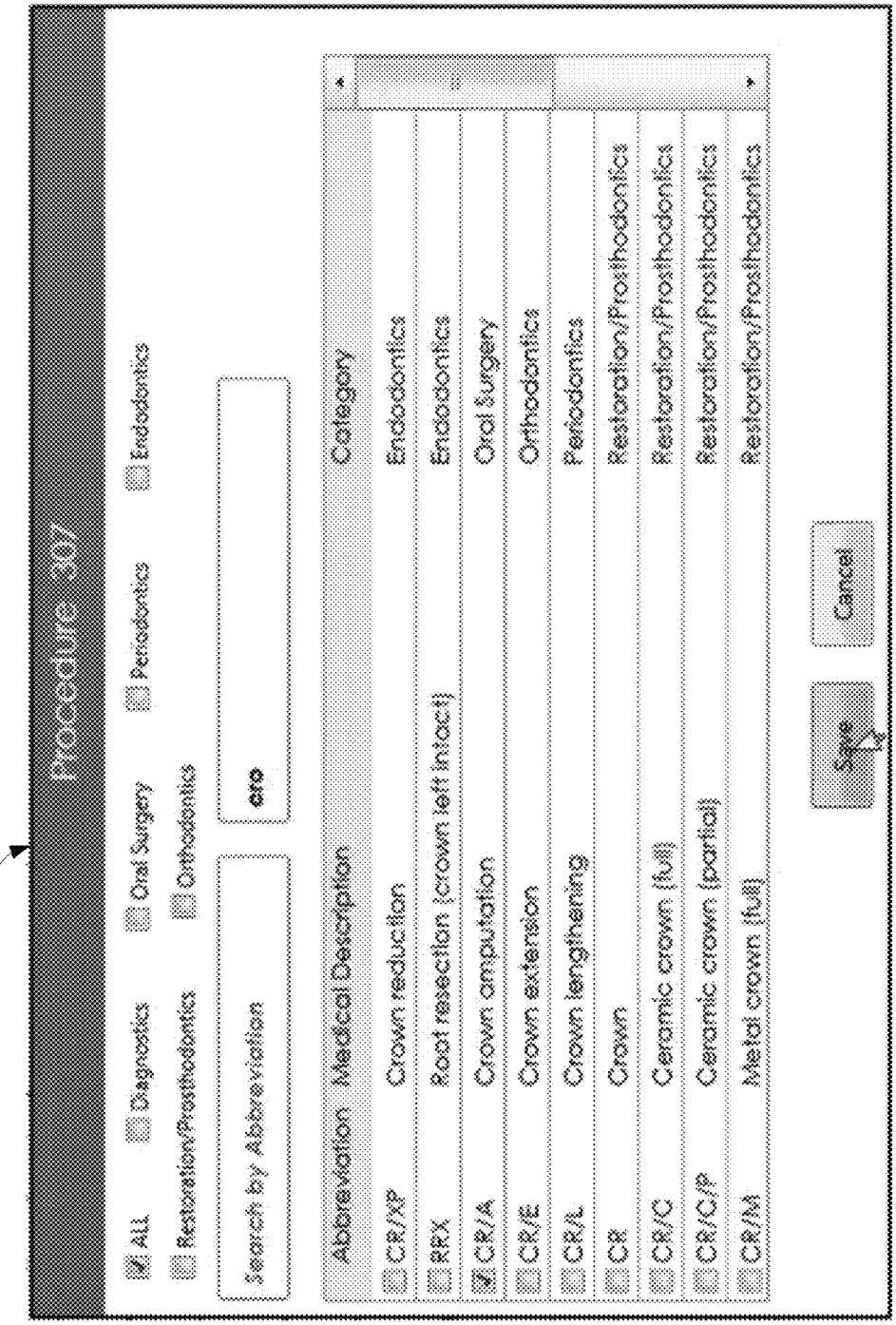
Figure 14G:
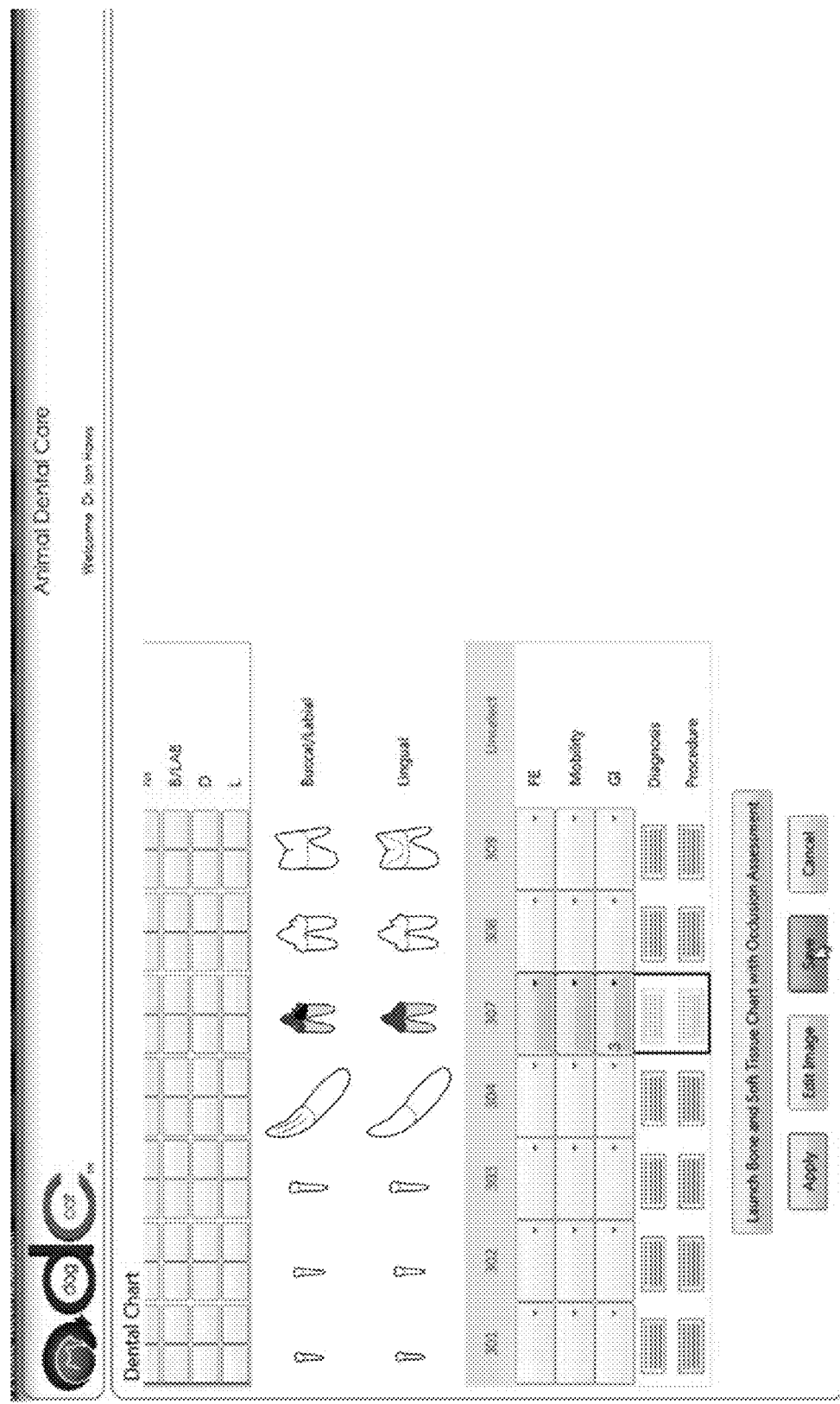

FIGS. 14A to 14G illustrate, in a sequence of screenshots, another example of operation of the dental charting system 100, 700, in accordance with some embodiments. This example involves a set of permanent feline teeth. FIG. 14A illustrates, in a screenshot, an example of a left mandible quadrant view 1400 of a set of permanent feline teeth. Tooth 307 is selected and receives a GI input value of "3". FIG. 14B illustrates, in a screenshot, another example of a diagnosis selection dialog box 1410. In this screenshot 1410, the diagnosis abbreviation "TR3" is selected as the diagnosis input value for tooth 307. FIG. 14C illustrates, in a screenshot 1420, the updated quadrant view showing the root for tooth 307 colored (e.g., in yellow) or shaded (corresponding to diagnosis input "TR3"). FIG. 14D illustrates, in a screenshot, another example of an image modification module 1430 that may be used to freehand edit tooth 307. FIG. 14E illustrates, in a screenshot 1440, the updated quadrant view showing a lesion overlaid on tooth 307. FIG. 14F illustrates, in a screenshot, another example of a procedure selection dialog box 1450. In this screenshot 1450, the procedure abbreviation "CR/A" (associated with oral surgery) is selected as the procedure input value for tooth 307. FIG. 14G illustrates, in a screenshot 1460, the updated quadrant view showing the crown of tooth 307 colored (e.g., in red) or shaded (corresponding to the crown amputation procedure input "CR/A").

Figure 15A:
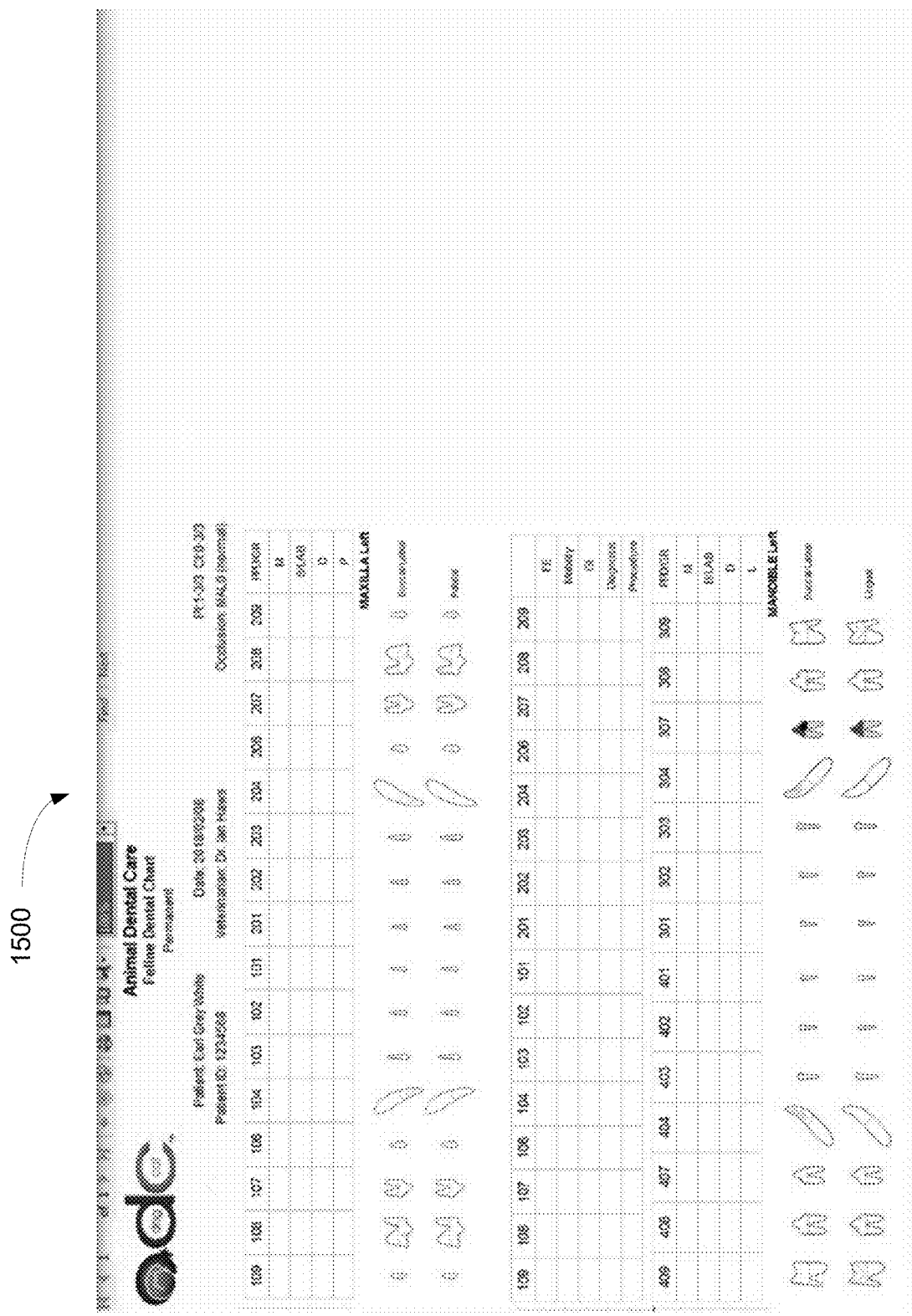
FIG. 15A illustrates, in a chart diagram, an example of an animal dental chart, in accordance with some embodiments.
Figure 15B:
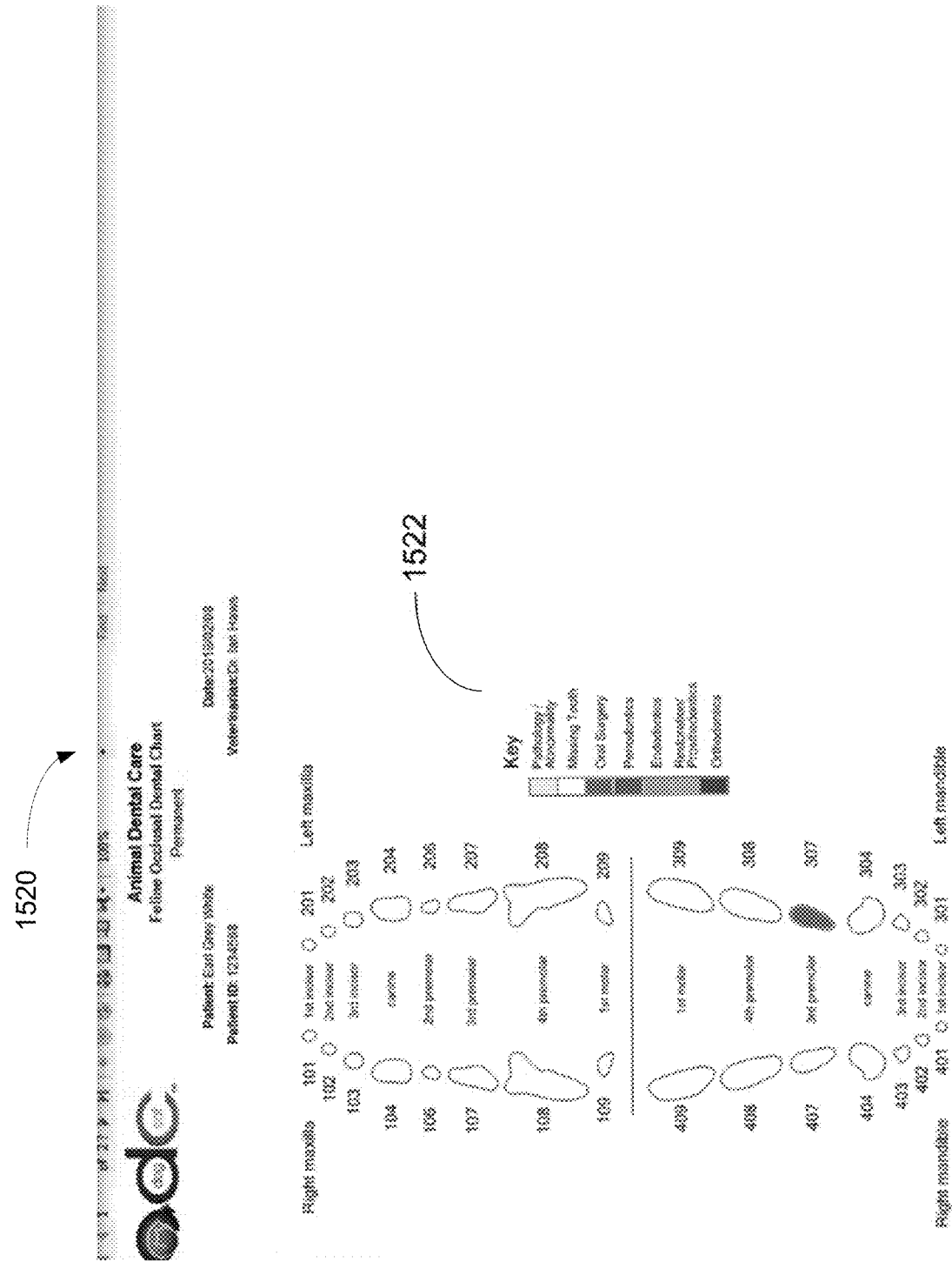
FIG. 15B illustrates, in a chart diagram, an example of an occlusal dental chart, in accordance with some embodiments.
Figure 15C:
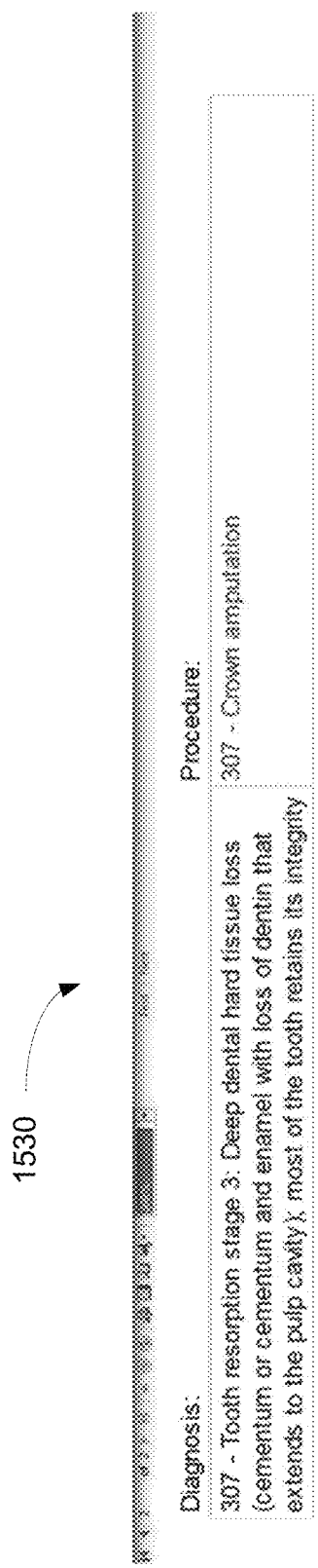
FIG. 15C illustrates, in a screenshot, another example of a technical description of a diagnosis and a procedure, in accordance with some embodiments.
Figure 15D:
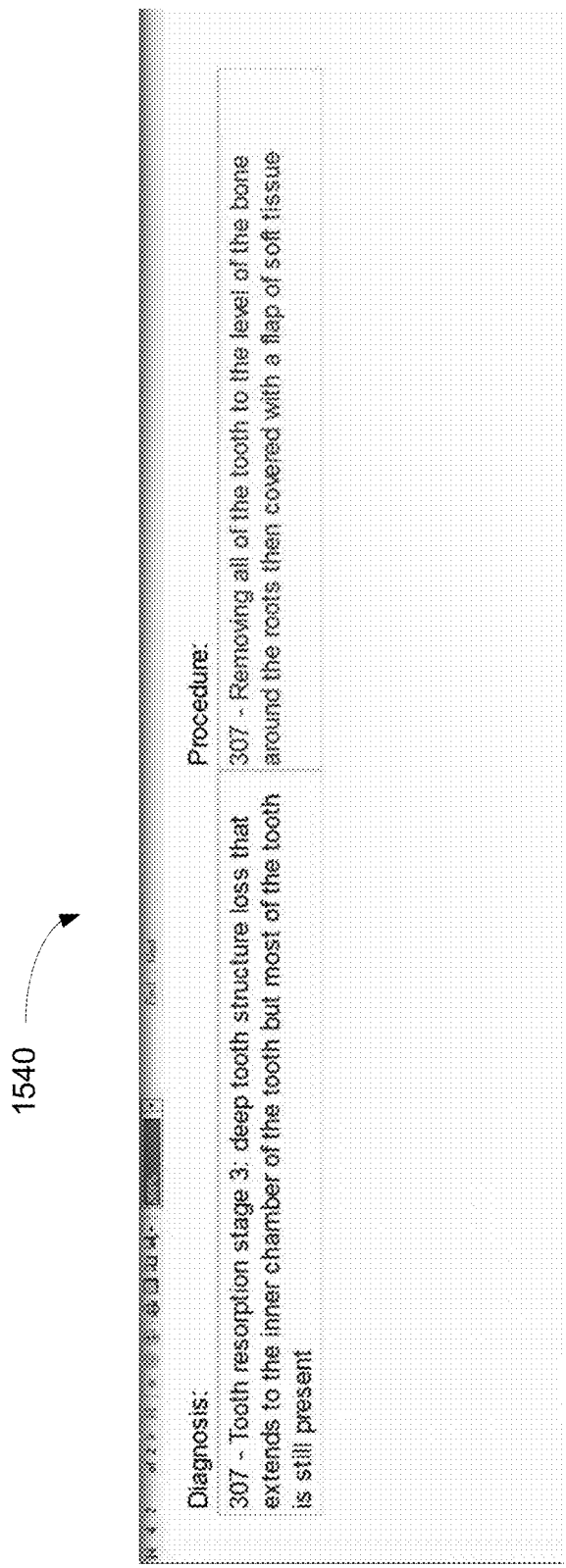
FIG. 15D illustrates, in a screenshot, another example of a lay person description of the diagnosis and the procedure, in accordance with some embodiments.

FIG. 15A illustrates, in a chart diagram, an example of an animal dental chart 1500, in accordance with some embodiments. The dental chart 1500 shows the changes to tooth 307 for the feline. FIG. 15B illustrates, in a chart diagram, an example of an occlusal dental chart 1520, in accordance with some embodiments. The occlusal dental chart may include a key 1522 identifying the meaning of color or shading on the teeth in the chart 1520. A second page may be added to the occlusal dental chart 1520 that includes the text for the diagnosis and procedure that have been applied to the teeth in the chart 1520. FIG. 15C illustrates, in a screenshot, an example of a technical description 1530 of the diagnosis and procedure that can be added as a second page or screen for an official report, in accordance with some embodiments. In this example, the diagnosis was "307—Tooth resorption stage 3; Deep dental hard tissue loss (cementum or cementum and enamel with loss of dentin that extends to the pulp cavity); most of the tooth retains its integrity." In this example, the procedure was "307—Crown amputation." FIG. 15D illustrates, in a screenshot, an example of a lay person description 1540 of the diagnosis and procedure that can be added as a second page or screen for a lay person or client report, in accordance with some embodiments. In this example, the diagnosis was "307—Tooth resorption stage 3; deep tooth structure loss that extends to the inner chamber of the tooth but most of the tooth is still present." In this example, the procedure was "307—Removing all of the tooth to the level of the bone around the roots then covered with a flap of soft tissue."

In some embodiments, when a patent's dental chart record is saved, all images related to all dental chart reports are regenerated and saved. This helps ensure that changes are immediately (and automatically) reflected in all dental chart reports.

In some embodiments, the dental charting system 100, 700, 780 may also include functionality to change root outline color and thickness when a "to be treated" or "TBT" diagnosis is assigned to a tooth (i.e., visual identification based upon a diagnosis). When this "TBT" diagnosis is entered in the system 100, 700, 780 and then either "Apply" 822 or "Save" functionality is selected, the outline color for the tooth image is changed (e.g., from black to red). Such a change in tooth outline color may be automatically performed for the dental charts, including the occlusal dental chart and dental summary chart with the occlusal views of teeth.

In some embodiments, when a permanent tooth is flagged as being deciduous, the tooth image and tooth number may be dynamically changed (i.e., unique flagging of a specific tooth).

Figure 16A:
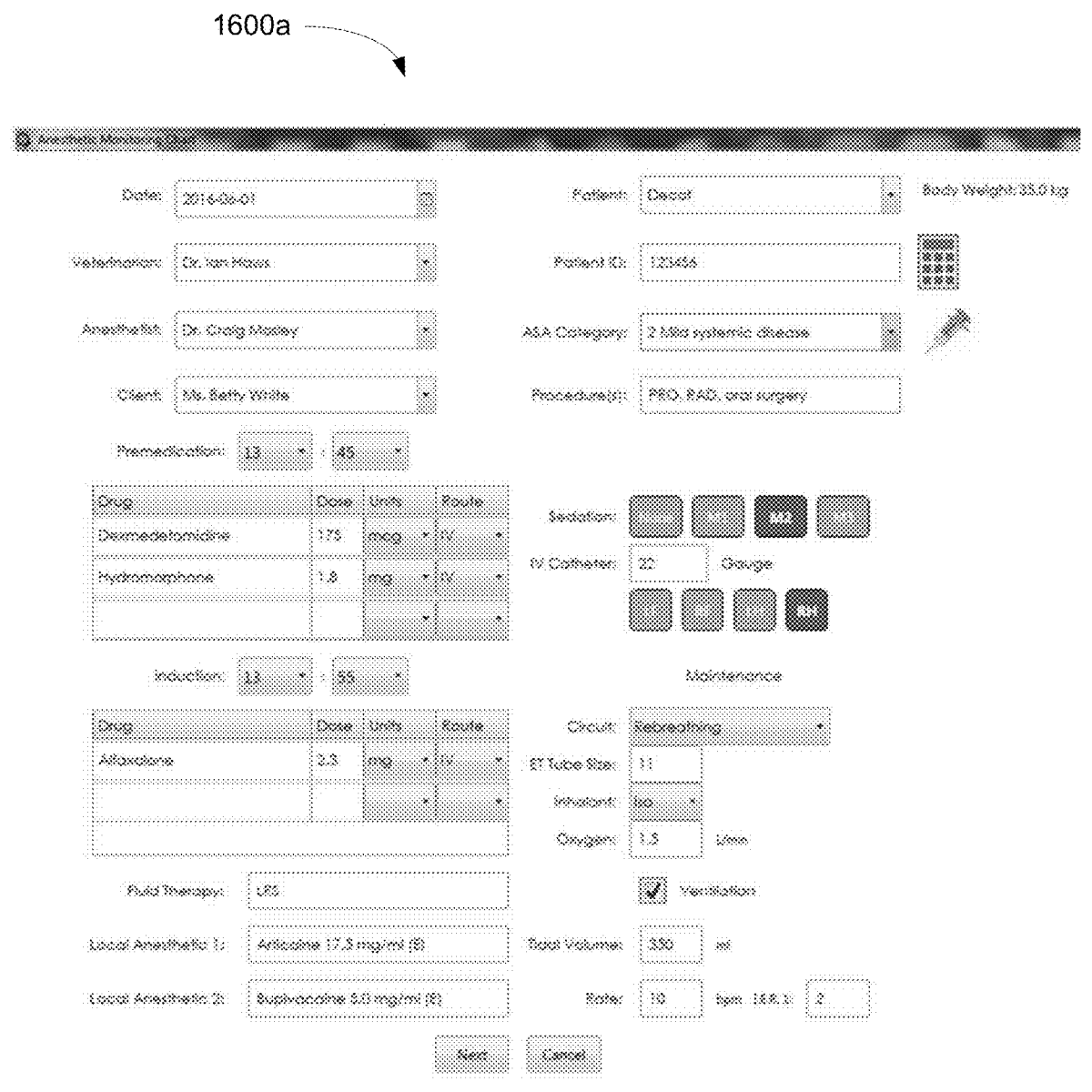
Figure 16B:
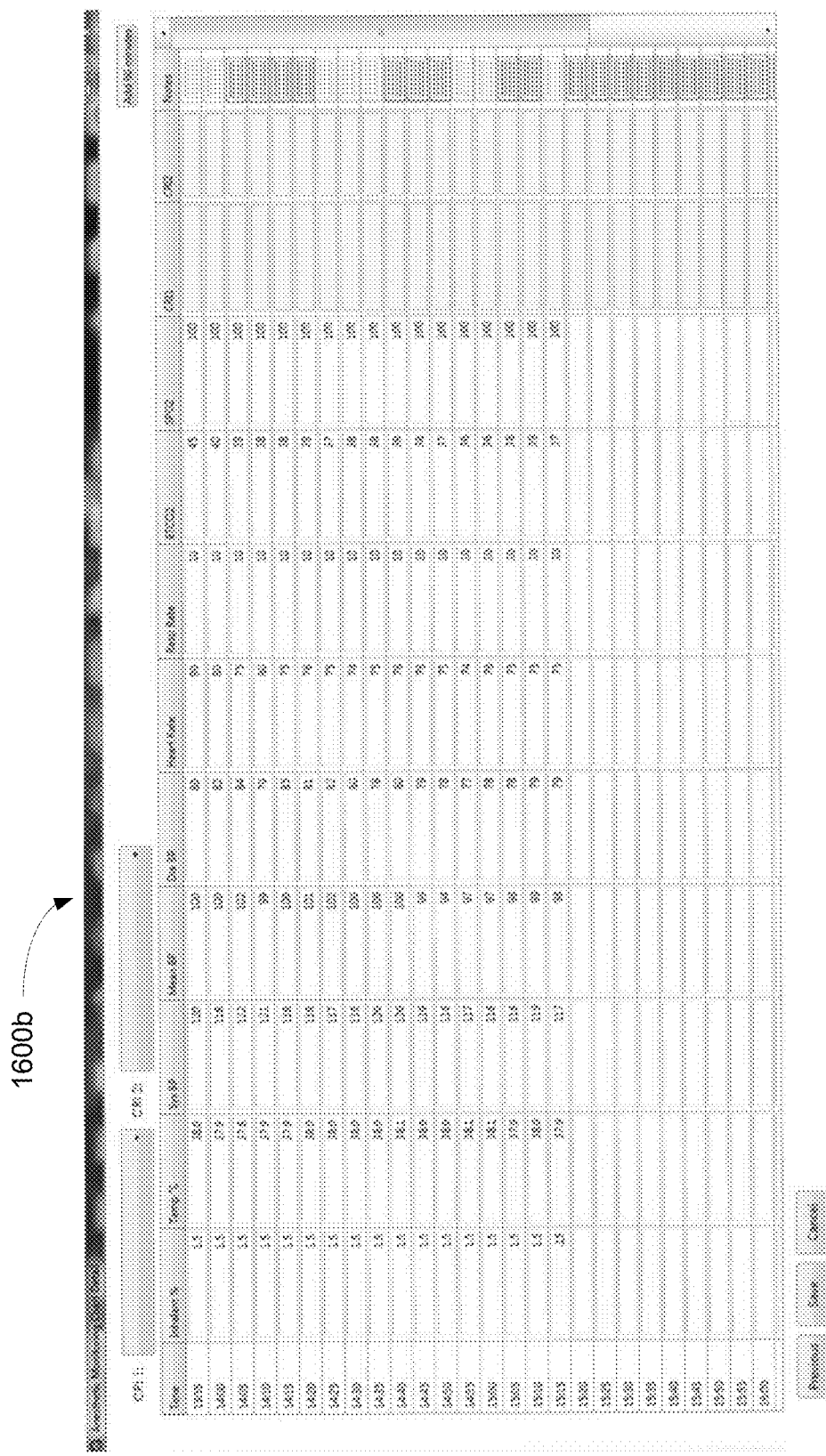
FIG. 16B illustrates, in a screenshot, an example of another anesthetic monitoring input field, in accordance with some embodiments.
Figure 17:
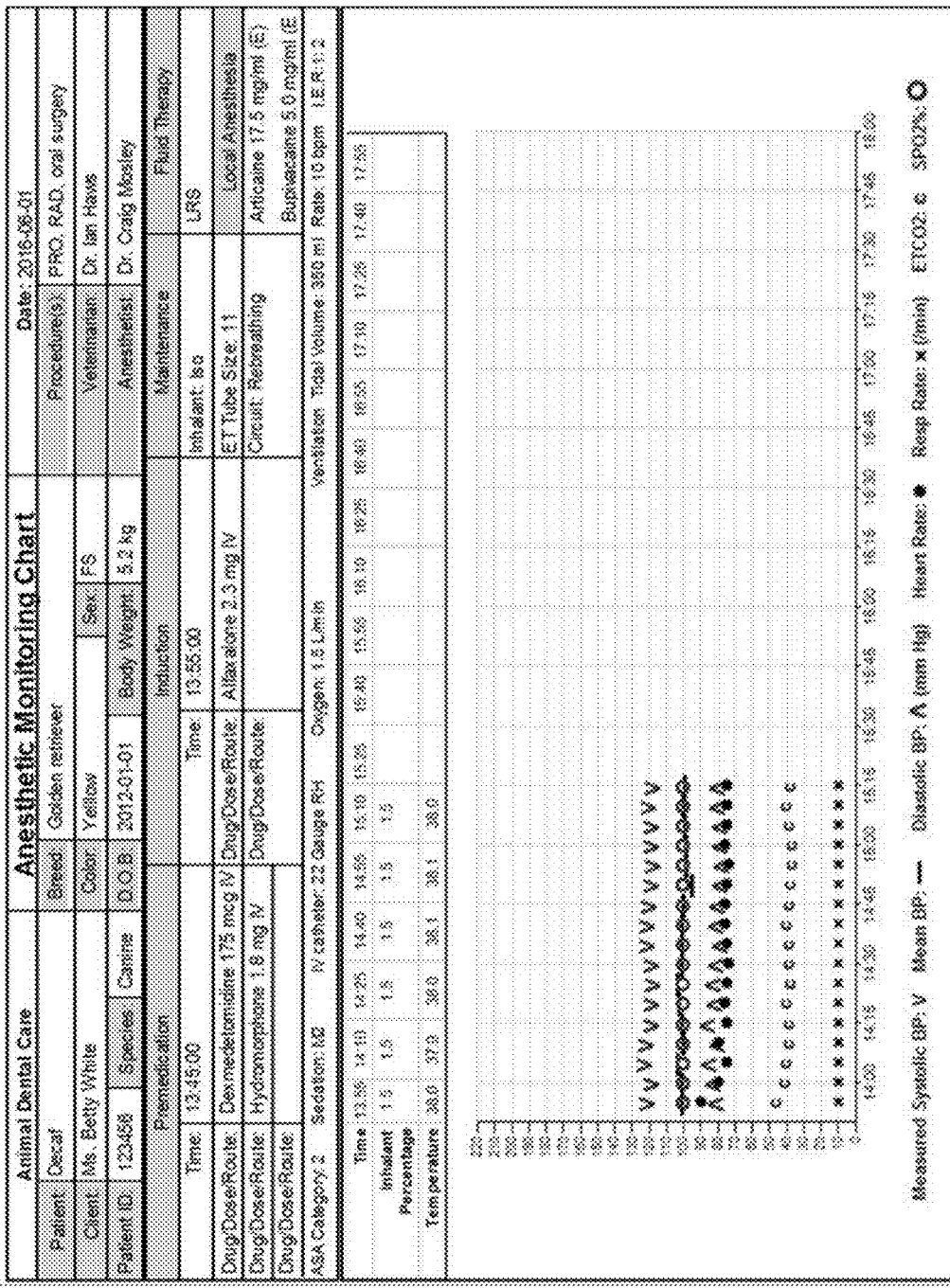
FIG. 17 illustrates, in a screenshot, an example of an anesthetic monitoring output, in accordance with some embodiments.

An anesthetic monitoring module may also be added to the dental charting system 100, 700, 780. The anesthetic monitoring module may be used to monitor a patient that is under an anesthetic during a dental diagnosis or procedure. FIG. 16A illustrates, in a screenshot, an example of an anesthetic monitoring input field 1600a, in accordance with some embodiments. FIG. 16B illustrates, in a screenshot, an example of another anesthetic monitoring input field 1600b, in accordance with some embodiments. FIG. 17 illustrates, in a screenshot, an example of an anesthetic monitoring output 1700, in accordance with some embodiments. The special characters shown in FIG. 17 allow for easier and faster readings while the animal is under an anesthetic.

Figure 18:
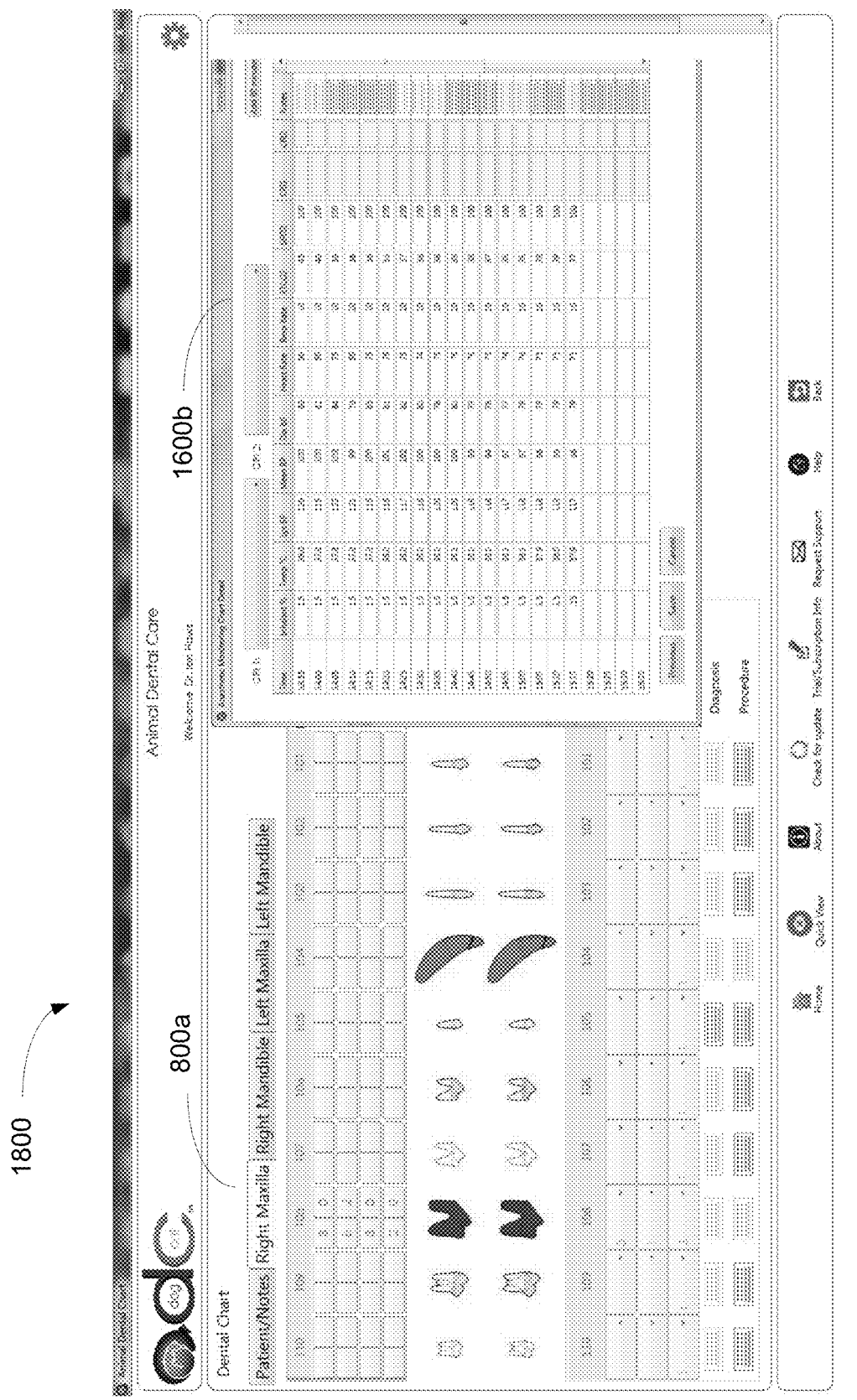
FIG. 18 illustrates, in a screenshot, an example of a quadrant view of the dental charting system together with an anesthetic monitoring input field, in accordance with some embodiments.

In some embodiments, the anesthetic monitoring module may be launched and displayed side-by-side with the dental charting system 100, 700, 780 display. FIG. 18 illustrates, in a screenshot, an example of a right maxilla quadrant view 800a of the dental charting system 100, 700, 780 together with an anesthetic monitoring input field 1600b, in accordance with some embodiments. Data may be periodically entered into the anaesthetic monitoring input field (for example, every five minutes).

In some embodiments, an auto-save feature may be included in the dental charting system 100, 700, 780 and/or anesthetic monitoring module. For example, the user interface may auto-save all field changes (i.e., record the changes) each minute to populate a data model or temporary record which can be subsequently sent to a server (e.g., after a session that an animal is under an anesthetic is completed) to update the permanent data stored at a central server. In this manner, an up-to-date version of the data may be saved frequently at a local level and less frequently at the central server level. Thus, an intermittent, connectionless, auto-save may be applied on a field-by-field basis to the data.

Figure 19:
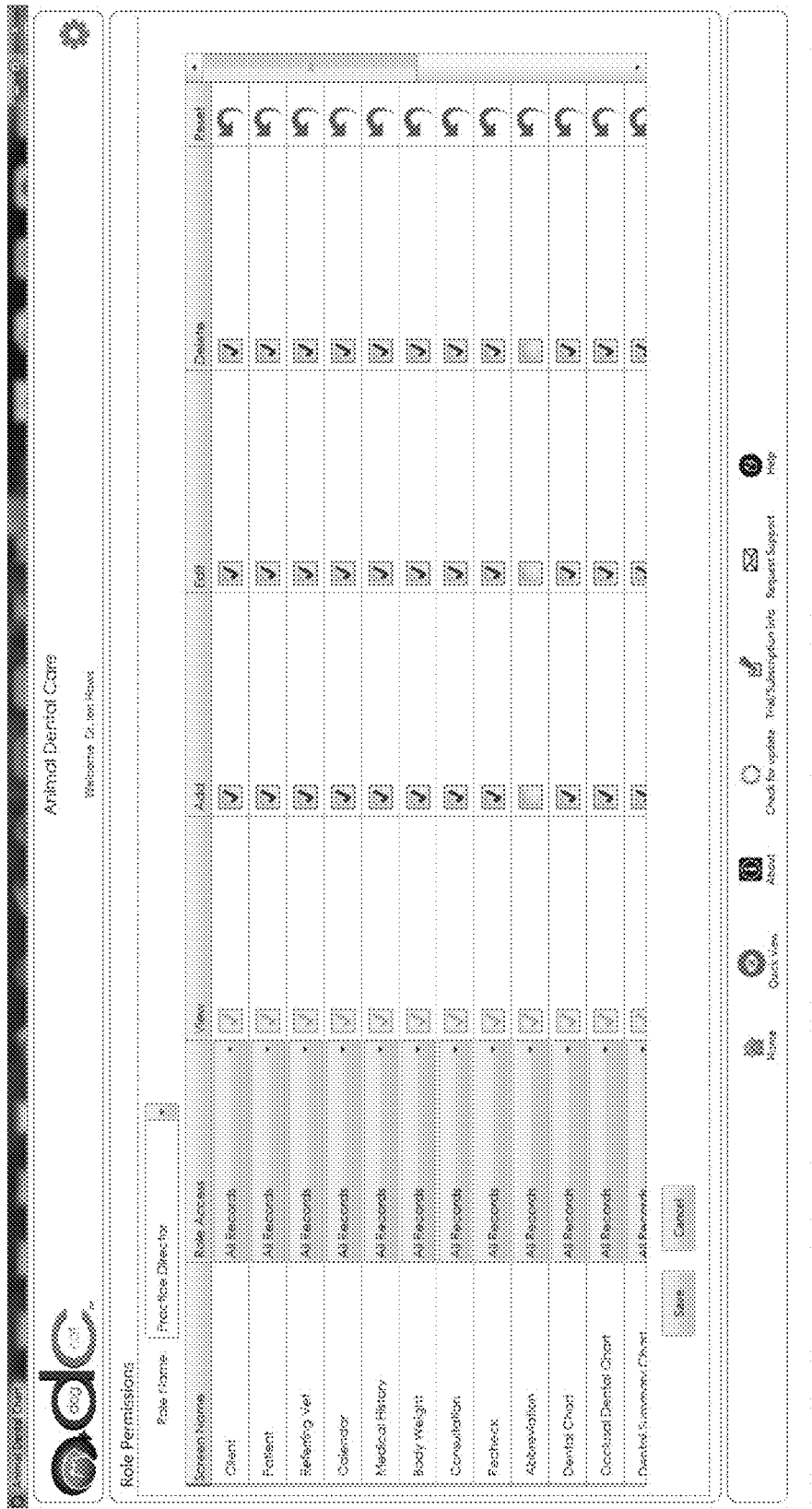
FIG. 19 illustrates, in a screenshot, an example of role permissions for the dental charting system, in accordance with some embodiments.

Some jurisdictions may have compliance rules for different roles in a veterinarian clinic. The dental charting system 100, 700, 780 may be include customizable permissions for each role to perform a view, add, edit, delete, etc., operation on the data. Thus, roles may be configured to be compliant with rules in the different jurisdictions. FIG. 19 illustrates, in a screenshot, an example of role permissions 1900 for the dental charting system 100, 700, 780, in accordance with some embodiments.

In some embodiments, an auto-locking function may be implemented. For example, a patient record may be set to read-only after a fixed number of days. The fixed number of days may be customized for each type of record.

Figure 20:
FIG. 20 illustrates, in a screenshot an example of an audit logging for the dental charting system, in accordance with some embodiments.

FIG. 20 illustrates, in a screenshot an example of an audit logging 2000 for the dental charting system 100, 700, 780, in accordance with some embodiments. For example, data that was deleted may be stored showing that it was deleted. In this manner, data relating to sessions with the patient may be created, added, changed, deleted, etc., with each type of data action date and time stamped. The date and time stamps allow for data from a past point in time to be regenerated, if needed.

In some jurisdictions, the local authority over veterinarians may mandate a digital audit transcript for medical management applications. In some embodiments, a digital document signature module may be implemented. For example, digital document signing may comprise a digital certificate, an secure socket layer (SSL) certificate, a data/time stamp, etc. and may be implemented in an automatic signature manner.

Figure 21:
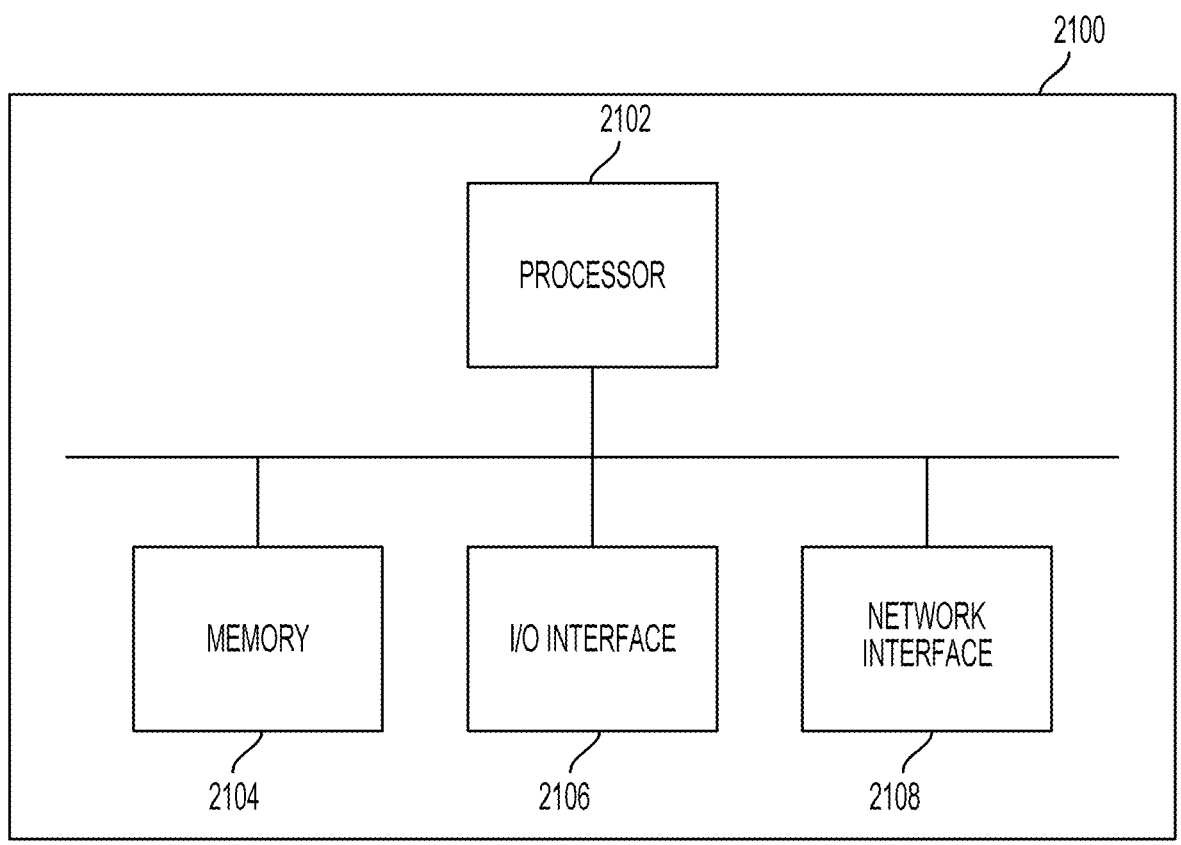
FIG. 21 illustrates, in a block schematic diagram, an example of a computing device, in accordance with some embodiments.

FIG. 21 illustrates, in a block schematic diagram, an example of a computing device 2100, according to some embodiments. There is provided a schematic diagram of computing device 2100, exemplary of an embodiment device that may implement the dental charting system 100, 700, 780. As depicted, computing device 2100 includes at least one processor 2102, memory 2104, at least one I/O interface 2106, and at least one network interface 2108.

Each processor 2102 may be a microprocessor or microcontroller, a digital signal processing (DSP) processor, an integrated circuit, a field programmable gate array (FPGA), a reconfigurable processor, a programmable read-only memory (PROM), or any combination thereof. The processor 2102 may be optimized for analyzing text or verbal responses to queries from clients, determining the optimal next query to transmit to users based on previous responses and the totality of information required, and transmitting the optimal next question to the user.

Memory 2104 may include a computer memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM).

Each I/O interface 2106 enables computing device 2100 to interconnect with one or more input devices, such as a keyboard, mouse, camera, touch screen and a microphone, or with one or more output devices such as a display screen and a speaker. I/O interface 2106 may also include application programming interfaces (APIs) which are configured to receive data sets in the form of information signals, including verbal communications recorded and digitized, and/or text input from users in response to queries posed to said users.

Each network interface 2108 enables computing device 2100 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., Wi-Fi, WiMAX), SS7 signaling network, fixed line, local area network, wide area network, and others. Network interface 808, for example, may be used to communicate audio files (e.g., MP3, WAV, etc.) containing recorded verbal responses from a user device to the system for processing via a speech-to-text engine.

The following discussion provides example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

The embodiments of the devices, systems and methods described herein may be implemented in a combination of both hardware and software. These embodiments may be implemented on programmable computers, each computer including at least one processor, a data storage system (including volatile memory or non-volatile memory or other data storage elements or a combination thereof), and at least one communication interface.

Program code is applied to input data to perform the functions described herein and to generate output information. The output information is applied to one or more output devices. In some embodiments, the communication interface may be a network communication interface. In embodiments in which elements may be combined, the communication interface may be a software communication interface, such as those for inter-process communication. In still other embodiments, there may be a combination of communication interfaces implemented as hardware, software, and combination thereof.

Throughout the foregoing discussion, references are made regarding servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, a server can include one or more computers operating as a web server, database server, or other type of computer server in a manner to fulfill described roles, responsibilities, or functions.

The technical solution of embodiments may be in the form of a software product. The software product may be stored in a non-volatile or non-transitory storage medium, which can be a compact disk read-only memory (CD-ROM), a USB flash disk, or a removable hard disk. The software product includes a number of instructions that enable a computer device (personal computer, server, or network device) to execute the methods provided by the embodiments.

The embodiments described herein are implemented by physical computer hardware, including computing devices, servers, receivers, transmitters, processors, memory, displays, and networks. The embodiments described herein provide useful physical machines and particularly configured computer hardware arrangements.

Although the embodiments have been described in detail, it should be understood that various changes, substitutions and alterations can be made herein.

Moreover, the scope of the present application is not intended to be limited to the particular embodiments of the process, machine, manufacture, composition of matter, means, methods and steps described in the specification.

As can be understood, the examples described above and illustrated are intended to be exemplary only.

What is claimed is:

1. A dental charting system comprising:
   at least one processor configured to execute instructions; and
   a memory storing a sequence of instructions which, when executed by the at least one processor, configure the at least one processor to:
   display a quadrant view of a set of teeth, the quadrant view comprising:
      a quadrant subset of the set of teeth, a primary image of each tooth in the quadrant subset displayed having a crown, a root and an outline; and
      at least one of a diagnosis field or a procedure field for each tooth in the quadrant subset;
   receive a selection input for at least one of the diagnosis field or the procedure field for a tooth in the quadrant set of teeth;
   update the primary image of the tooth in the quadrant set of teeth based on the selection input, wherein the tooth is displayed in the quadrant view in a color associated with the received selection input;
   display a secondary image of the tooth;
   receive an edit input of the tooth on the secondary image;
   merge the edit input with the updated primary image of the tooth, wherein the processor is configured to:
      produce a third image of the tooth from the edit input on the secondary image of the tooth;
      perform an XOR function between the third image and the second image to produce a fourth image comprising the edit input; and
      produce a fifth image comprising the updated primary image of the tooth with an overlay of the fourth image of the edit input; and
   generate a dental chart displaying the set of teeth, wherein the fifth image of the tooth is displayed in the dental chart.

2. The system as claimed in claim 1, wherein the primary image of the tooth comprises color associated with past selection inputs.

3. The system as claimed in claim 1, wherein to generate a dental chart, the at least one processor is configured to at least one of:
 display, for each tooth, the received input for the at least one of the diagnosis field or the procedure field; or
 generate a technical report based upon the received input for the at least one of the diagnosis field or the procedure field.

4. The system as claimed in claim 1, wherein the at least one processor is configured to:
 display at least one periodontal measurement field for each tooth in the quadrant set of teeth; and
 receive an input selecting a periodontal measurement field for at least one tooth in the quadrant set of teeth.

5. The system as claimed in claim 4, wherein:
 the at least one periodontal measurement field comprises at least one of a mesial view field, a buccal/labial view field, a distal view field and a palatal/lingual view field; and
 to receive an input selecting a periodontal measurement field, the at least one processor is configured to receive a value associated with the periodontal measurement for an associated view of the at least one tooth.

6. The system as claimed in 5, wherein the at least one periodontal measurement field comprises at least one of:
 a left periodontal measurement field for receiving a periodontal probing depth value associated with the associated view of the at least one tooth, and a right periodontal measurement field for receiving a gingival recession value associated with the associated view of the at least one tooth; or
 a left periodontal measurement field for receiving a periodontal attachment loss value associated with the associated view of the at least one tooth, and a right periodontal measurement field for receiving a periodontal probing depth value associated with the associated view of the at least one tooth.

7. The system as claimed in claim 1, wherein the at least one processor is configured to:
 display at least one diagnosis measurement field for each tooth in the quadrant set of teeth; and
 receive an input selecting a diagnosis measurement value for at least one tooth in the quadrant set of teeth.

8. The system as claimed in claim 7, wherein the diagnosis measurement field comprises one of a furcation exposure stage value, a mobility stage value and a gingivitis index value.

9. The system as claimed in claim 1, wherein the at least one processor is configured to:
 receive a plurality of selection input, for the at least one of the diagnosis field or the procedure field, for respective teeth in the quadrant set of teeth; and
 update respective primary images of the teeth in the quadrant set of teeth based on their respective selection input, wherein each tooth is displayed in the quadrant view in a color associated with its respective received selection input.

10. The system as claimed in claim 1, wherein the at least one processor is configured to:
 receive a plurality of selection inputs for the at least one of the diagnosis field or the procedure field for the tooth in a sequence;
 store the plurality of selection inputs in order of the sequence; and
 update the primary image of the tooth in the quadrant set of teeth based on the sequence of the plurality of selection inputs, wherein the tooth is displayed in the quadrant view in a color associated with a most recent selection input.

11. A computer-implemented method of generating a dental chart, the method comprising:
 displaying a quadrant view of a set of teeth, the quadrant view comprising:
  a quadrant subset of the set of teeth, a primary image of each tooth in the quadrant subset displayed having a crown, a root and an outline; and
  at least one of a diagnosis field or a procedure field for each tooth in the quadrant subset;
 receiving a selection input for at least one of the diagnosis field or the procedure field for the tooth;
 updating the primary image of the tooth in the quadrant set of teeth based on the selection input, wherein the tooth is displayed in the quadrant view in a color associated with the received selection input;
 displaying a secondary image of the tooth;
 receiving an edit input of the tooth on the secondary image;
 merging the edit input with the updated primary image of the tooth, comprising:
  producing a third image of the tooth from the edit input on the secondary image of the tooth;
  performing an XOR function between the third image and the second image to produce a fourth image comprising the edit input; and
  producing a fifth image comprising the updated primary image of the tooth with an overlay of the fourth image of the edit input; and
 generating a dental chart displaying the set of teeth, wherein the fifth image of the tooth is displayed in the dental chart.

12. The method as claimed in claim 11, wherein the primary image of the tooth comprises color associated with past selection inputs.

13. The method as claimed in claim 11, comprising at least one of:
 displaying on the generated dental chart, for each tooth, the received input for the at least one of the diagnosis field or the procedure field; or
 generating a technical report based upon the received input for the at least one of the diagnosis field or the procedure field.

14. The method as claimed in claim 11,
 wherein the quadrant view further comprises at least one periodontal measurement field for each tooth in the quadrant set of teeth; and
 the method comprising receiving an input selecting a periodontal measurement field for at least one tooth in the quadrant set of teeth.

15. The method as claimed in claim 14, wherein:
 the at least one periodontal measurement field comprises at least one of a mesial view field, a buccal/labial view field, a distal view field and a palatal/lingual view field; and
 the receiving an input selecting a periodontal measurement field comprises receiving a value associated with the periodontal measurement for an associated view of the at least one tooth.

16. The method as claimed in 17, wherein the at least one periodontal measurement field comprises at least one of:
 a left periodontal measurement field for receiving a periodontal probing depth value associated with the associated view of the at least one tooth, and a right periodontal measurement field for receiving a gingival recession value associated with the associated view of the at least one tooth; or a left periodontal measurement field for receiving a periodontal attachment loss value associated with the associated view of the at least one tooth, and a right periodontal measurement field for receiving a periodontal probing depth value associated with the associated view of the at least one tooth.

17. The method as claimed in claim 11, wherein the quadrant view further comprises at least one diagnosis measurement field for each tooth in the quadrant set of teeth; and further comprising receiving an input selecting a diagnosis measurement value for at least one tooth in the quadrant set of teeth.

18. The method as claimed in claim 17, wherein the diagnosis measurement field comprises one of a furcation exposure stage value, a mobility stage value and a gingivitis index value.

19. The method as claimed in claim 11, comprising:

receiving a plurality of selection input, for the at least one of the diagnosis field or the procedure field, for respective teeth in the quadrant set of teeth; and updating respective primary images of the teeth in the quadrant set of teeth based on their respective selection input, wherein each tooth is displayed in the quadrant view in a color associated with its respective received selection input.

20. The method as claimed in claim 11, comprising:

receiving a plurality of selection inputs for the at least one of the diagnosis field or the procedure field for the tooth in a sequence;

storing the plurality of selection inputs in order of the sequence; and updating the primary image of the tooth in the quadrant set of teeth based on the sequence of the plurality of selection inputs, wherein the tooth is displayed in the quadrant view in a color associated with a most recent selection input.

21. A non-transitory computer-readable medium having instructions thereon which, when executed by a processor, perform a method of generating a dental chart, the method comprising:

displaying a quadrant view of a set of teeth, the quadrant view comprising:

a quadrant subset of the set of teeth, each tooth in the quadrant subset displayed having a crown, a root and an outline; and at least one of a diagnosis field or a procedure field for each tooth in the quadrant subset;

receiving a selection input for at least one of the diagnosis field or the procedure field for at least one tooth in the quadrant set of teeth;

updating the primary image of the tooth in the quadrant set of teeth based on the selection input, wherein the tooth is displayed in the quadrant view in a color associated with the received selection input;

displaying a secondary image of the tooth;

receiving an edit input of the tooth on the secondary image;

merging the edit input with the primary image of the tooth, comprising:

producing a third image of the tooth from the edit input on the secondary image of the tooth;

performing an XOR function between the third image and the second image to produce a fourth image comprising the edit input; and producing a fifth image comprising the updated primary image of the tooth with an overlay of the fourth image of the edit input; and generating a dental chart displaying the set of teeth, wherein the fifth image of the tooth is displayed in the dental chart.

* * * * *